US011680296B2

(12) United States Patent
Shalek et al.

(10) Patent No.: US 11,680,296 B2
(45) Date of Patent: Jun. 20, 2023

(54) MYCOBACTERIUM TUBERCULOSIS HOST-PATHOGEN INTERACTION

(71) Applicant: Massachusetts Institute of Technology, Cambridge, MA (US)

(72) Inventors: Alexander K. Shalek, Cambridge, MA (US); Carly Ziegler, Cambridge, MA (US)

(73) Assignee: Massachusetts Institute of Technology, Cambridge, MA (US)

(*) Notice: Subject to any disclaimer, the term of this patent is extended or adjusted under 35 U.S.C. 154(b) by 0 days.

(21) Appl. No.: 16/756,655

(22) PCT Filed: Oct. 16, 2018

(86) PCT No.: PCT/US2018/056168
§ 371 (c)(1),
(2) Date: Apr. 16, 2020

(87) PCT Pub. No.: WO2019/079362
PCT Pub. Date: Apr. 25, 2019

(65) Prior Publication Data
US 2021/0139990 A1 May 13, 2021

Related U.S. Application Data

(60) Provisional application No. 62/573,049, filed on Oct. 16, 2017.

(51) Int. Cl.
*C12Q 1/6883* (2018.01)

(52) U.S. Cl.
CPC ..... *C12Q 1/6883* (2013.01); *C12Q 2600/106* (2013.01); *C12Q 2600/158* (2013.01)

(58) Field of Classification Search
CPC ........ A61K 39/00; A61K 39/02; A61K 39/04; C12Q 2600/106; C12Q 2600/158; C12Q 1/6883
USPC ...... 424/9.1, 9.2, 184.1, 234.1, 248.1, 278.1
See application file for complete search history.

(56) References Cited

U.S. PATENT DOCUMENTS

| | | | |
|---|---|---|---|
| 4,737,323 A | 4/1988 | Martin et al. | |
| 4,837,028 A | 6/1989 | Allen | |
| 5,030,015 A | 7/1991 | Baker et al. | |
| 5,641,870 A | 6/1997 | Rinderknecht et al. | |
| 5,811,097 A | 9/1998 | Allison et al. | |
| 8,697,359 B1 | 4/2014 | Zhang | |
| 8,771,945 B1 | 7/2014 | Zhang | |
| 8,795,965 B2 | 8/2014 | Zhang | |
| 8,865,406 B2 | 10/2014 | Zhang et al. | |
| 8,871,445 B2 | 10/2014 | Cong et al. | |
| 8,889,356 B2 | 11/2014 | Zhang | |
| 8,889,418 B2 | 11/2014 | Zhang et al. | |
| 8,895,308 B1 | 11/2014 | Zhang et al. | |
| 8,906,616 B2 | 12/2014 | Zhang et al. | |
| 8,932,814 B2 | 1/2015 | Cong et al. | |
| 8,945,839 B2 | 2/2015 | Zhang | |
| 8,993,233 B2 | 3/2015 | Zhang et al. | |
| 8,999,641 B2 | 4/2015 | Zhang et al. | |
| 2006/0013842 A1 | 1/2006 | Matkin et al. | |
| 2011/0265198 A1 | 10/2011 | Gregory et al. | |
| 2012/0017290 A1 | 1/2012 | Cui et al. | |
| 2013/0236946 A1 | 9/2013 | Gouble | |
| 2014/0170753 A1 | 6/2014 | Zhang | |
| 2014/0179006 A1 | 6/2014 | Zhang | |
| 2014/0179770 A1 | 6/2014 | Zhang et al. | |
| 2014/0186843 A1 | 7/2014 | Zhang et al. | |
| 2014/0186919 A1 | 7/2014 | Zhang et al. | |
| 2014/0186958 A1 | 7/2014 | Zhang et al. | |
| 2014/0189896 A1 | 7/2014 | Zhang et al. | |
| 2014/0227787 A1 | 8/2014 | Zhang | |
| 2014/0234972 A1 | 8/2014 | Zhang | |
| 2014/0242664 A1 | 8/2014 | Zhang et al. | |
| 2014/0242699 A1 | 8/2014 | Zhang | |
| 2014/0242700 A1 | 8/2014 | Zhang et al. | |
| 2014/0248702 A1 | 9/2014 | Zhang et al. | |
| 2014/0256046 A1 | 9/2014 | Zhang et al. | |
| 2014/0273231 A1 | 9/2014 | Zhang et al. | |
| 2014/0273232 A1 | 9/2014 | Zhang et al. | |
| 2014/0273234 A1 | 9/2014 | Zhang et al. | |
| 2014/0287938 A1 | 9/2014 | Zhang et al. | |
| 2014/0310830 A1 | 10/2014 | Zhang et al. | |
| 2015/0232883 A1 | 8/2015 | Dahlman et al. | |

(Continued)

FOREIGN PATENT DOCUMENTS

| | | |
|---|---|---|
| EP | 0 404 097 A2 | 12/1990 |
| EP | 2 771 468 B1 | 2/2015 |

(Continued)

OTHER PUBLICATIONS

Bowie et al. (Science, 1990, 247:1306-1310) (Year: 1990).*
Burgess et al. (J. Cell Biol. 111:2129-2138, 1990) (Year: 1990).*
Lazar et al. (Mol. Cell. Biol., 8:1247-1252, 1988) (Year: 1988).*
Bork (Genome Research, 2000; 10:398-400) (Year: 2000).*
Hoppner (Horm Re. 2002, 58 Suppl. 3:7-15) (Year: 2002).*
Aguirre et al., Cancer Discv, 2016; 6(8): 914-29 (Year: 2016).*
Massachusetts Institute of Technology, "Notification of Transmittal of the International Search Report and the Written Opinion of the International Searching Authority, or the Declaration", PCT/US2018/056168, dated Feb. 11, 2019, 17 pages.
Rajaram, et al., "M. tuberculosis-Initiated Human Mannose Receptor Signaling Regulates Macrophage Recognition and Vesicle Trafficking by FcRg-Chain, Grb2, and SHP-1", Cell Reports, vol. 21, Oct. 3, 2017, pp. 126-140.

(Continued)

*Primary Examiner* — Brian Gangle
*Assistant Examiner* — Lakia J Jackson-Tongue
(74) *Attorney, Agent, or Firm* — F. Brent Nix, Esq.; Johnson, Marcou, Isaacs & Nix, LLC

(57) ABSTRACT

Gene expression signatures and pathways associated with tuberculosis are identified. The invention provides for diagnostic assays based on gene markers and cell composition, as well as therapeutic targets for modulating tuberculosis infection. In addition, tuberculosis copy number contained in cells and methods of detecting high and low copy number are disclosed.

13 Claims, 29 Drawing Sheets
Specification includes a Sequence Listing.

(56) References Cited

U.S. PATENT DOCUMENTS

| | | | |
|---|---|---|---|
| 2016/0154005 A1* | 6/2016 | Paramithiotis | G01N 33/5695 506/9 |
| 2017/0082623 A1 | 3/2017 | Rengarajan et al. | |
| 2017/0166903 A1 | 6/2017 | Zhang et al. | |
| 2017/0306335 A1 | 10/2017 | Zhang et al. | |
| 2019/0032083 A1* | 1/2019 | Kotin | C12N 15/63 |

FOREIGN PATENT DOCUMENTS

| | | |
|---|---|---|
| EP | 2 784 162 B1 | 4/2015 |
| EP | 2 764 103 B1 | 8/2015 |
| WO | 93/11161 A1 | 6/1993 |
| WO | 96/40281 A2 | 12/1996 |
| WO | 2014/018423 A2 | 1/2014 |
| WO | 2014/093595 A1 | 6/2014 |
| WO | 2014/093622 A2 | 6/2014 |
| WO | 2014/093635 A1 | 6/2014 |
| WO | 2014/093655 A2 | 6/2014 |
| WO | 2014/093661 A2 | 6/2014 |
| WO | 2014/093694 A1 | 6/2014 |
| WO | 2014/093701 A1 | 6/2014 |
| WO | 2014/093709 A1 | 6/2014 |
| WO | 2014/093712 A1 | 6/2014 |
| WO | 2014/093718 A1 | 6/2014 |
| WO | 2014/204723 A1 | 12/2014 |
| WO | 2014/204724 A1 | 12/2014 |
| WO | 2014/204725 A1 | 12/2014 |
| WO | 2014/204726 A1 | 12/2014 |
| WO | 2014/204727 A1 | 12/2014 |
| WO | 2014/204728 A1 | 12/2014 |
| WO | 2014/204729 A1 | 12/2014 |
| WO | 2014/210353 A2 | 12/2014 |
| WO | 2015/065964 A1 | 5/2015 |
| WO | 2015/089351 A1 | 6/2015 |
| WO | 2015/089364 A1 | 6/2015 |
| WO | 2015/089465 A1 | 6/2015 |
| WO | 2016/040476 A1 | 3/2016 |
| WO | 2016/069591 A2 | 5/2016 |
| WO | 2016/168584 A1 | 10/2016 |
| WO | 2017/124101 A2 | 7/2017 |
| WO | 2018/035250 A1 | 2/2018 |
| WO | 2019/079362 A1 | 4/2019 |

OTHER PUBLICATIONS

Tailleux, et al., "Probing Host Pathogen Cross-Talk by Transcriptional Profiling of Both *Mycobacterium tuberculosis* and Infected Human Dendritic Cells and Macrophages", PLos One, vol. 3, No. 1, 2008, pp. 1-14.

Anti-LGALS12 (Galectin-12, Gal-12, Galectin-related Inhibitor of Proliferation, GRIP1), Biomol, US Biological Life Sciences, retrieved from the internet on Jun. 10, 2021, www.biomol.com/products/antibodies/primary-antibodies/general/anti-lgals12-galectin-12-gal-12-galectin-related-inhibitor-of-proliferation-grip1-129066.50, 1 page.

Askari et al., "Rosiglitazone Inhibits Acyl-CoA Synthetase Activity and Fatty Acid Partitioning to Diacylglycerol and Triacylglycerol via a Peroxisome Proliferator-Activated Receptor-γ-Independent Mechanism in Human Arterial Smooth Muscle Cells and Macrophages", Diabetes, 56(4), 2007, 19 pages.

Robinson et al., "Interleukin-12 and Interleukin-27 Regulate Macrophage Control of *Mycobacterium tuberculosis*", JID, 198, 2008, pp. 359-366.

Sun et al., "*Mycobacterium tuberculosis* Nucleoside Diphosphate Kinase Inactivates Small GTPases Leading to Evasion of Innate Immunity", PLOS Pathogens, 9(7), 2013, e1003499, 14 pages.

Torrado et al., "Interleukin 27R regulates CD4+ T cell phenotype and impacts protective immunity during *Mycobacterium tuberculosis* infection", J Exp Med 212 (9), 2015, pp. 1449-1463.

Boch et al., "Breaking the Code of DNA Binding Specificity of TAL-type III Effectors", Science, vol. 326, No. 5959, Dec. 11, 2009, 1509-1512.

Macosko et al., "Highly Parallel Genome-Wide Expression Profiling of Individual Cells Using Nanoliter Droplets", Cell, vol. 161, No. 5, May 21, 2015, 25 pages.

Moscou et al., "A Simple Cipher Governs DNA Recognition by TAL Effectors", Science, vol. 326, Issue 5959, Dec. 11, 2009, 1501 page.

Platt et al., "CRISPR-Cas9 Knockin Mice for Genome Editing and Cancer Modeling", Cell, vol. 159, No. 2, Oct. 9, 2014, 31 pages.

Zhang et al., "Efficient Construction of Sequence-Specific TAL Effectors for Modulating Mammalian Transcription", Nature Biotechnology, vol. 29, No. 2, Feb. 2011, 149-153.

\* cited by examiner

FIG. 3

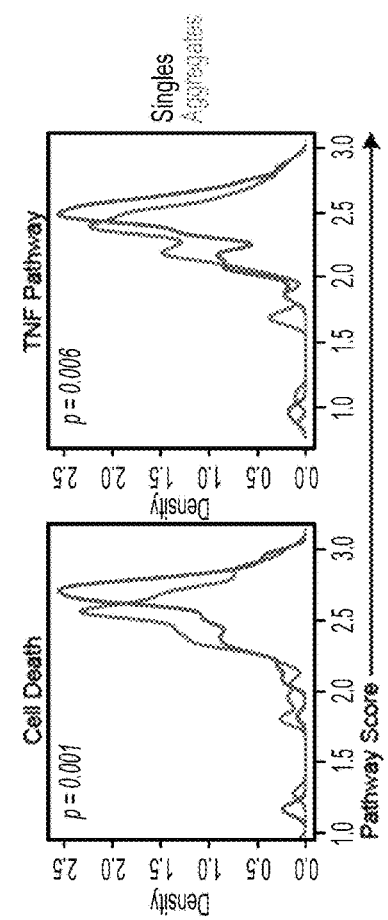
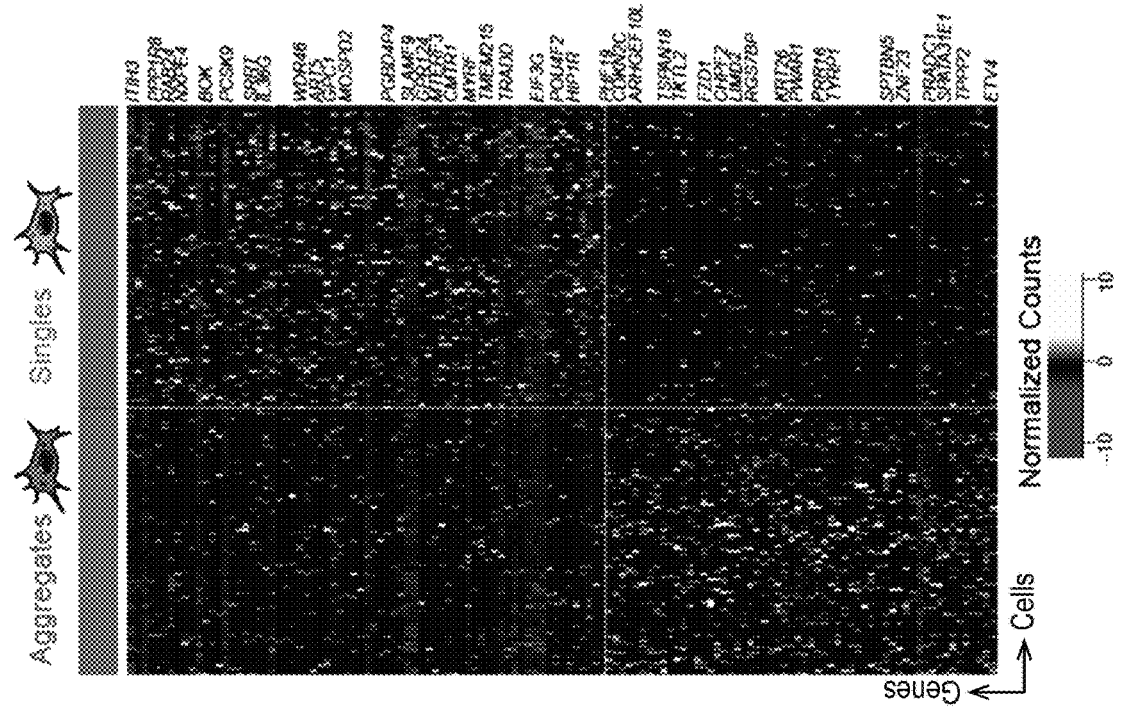
FIG. 4A
FIG. 4B

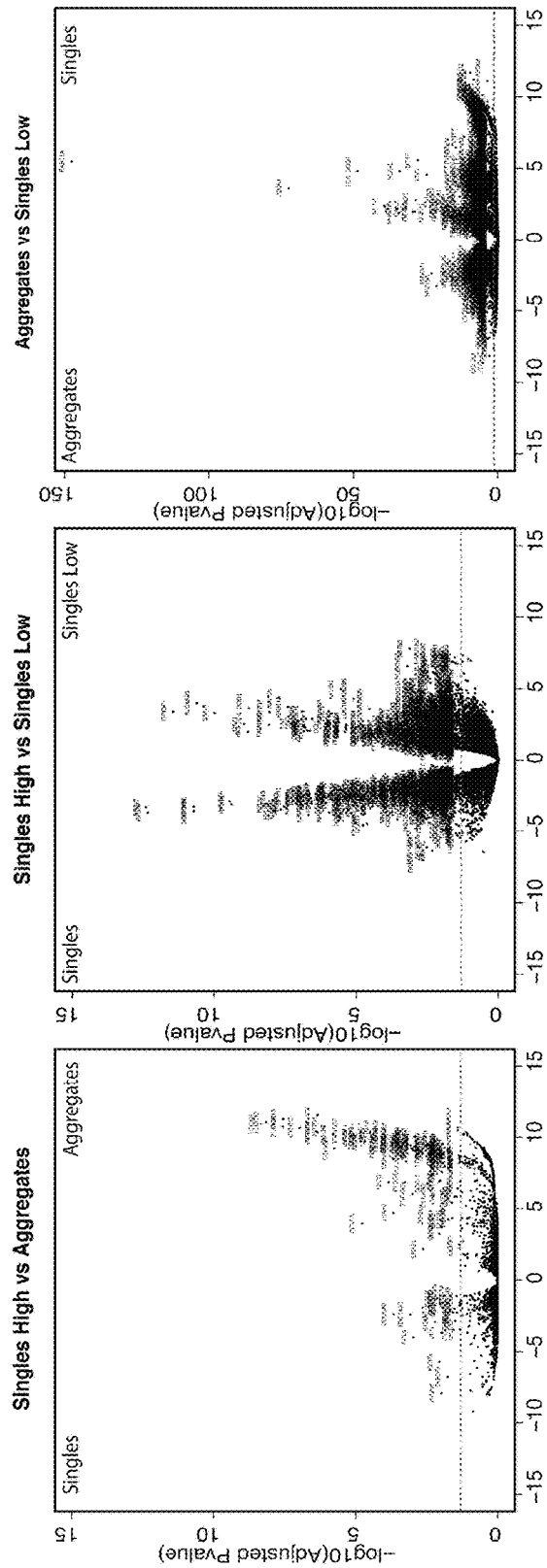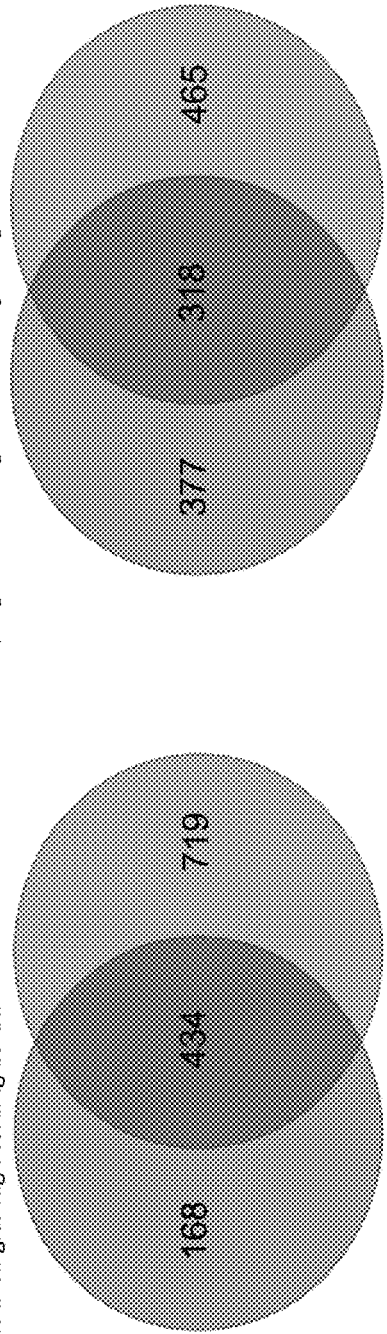
FIG. 24A  FIG. 24B  FIG. 24C  FIG. 24D  FIG. 24E

SEQUENCE LISTING

```
<160> NUMBER OF SEQ ID NOS: 18

<210> SEQ ID NO 1
<211> LENGTH: 7
<212> TYPE: PRT
<213> ORGANISM: Simian virus 40

<400> SEQUENCE: 1

Pro Lys Lys Lys Arg Lys Val
1               5

<210> SEQ ID NO 2
<211> LENGTH: 16
<212> TYPE: PRT
<213> ORGANISM: Artificial Sequence
<220> FEATURE:
<223> OTHER INFORMATION: Synthetic nucleoplasmin bipartite NLS

<400> SEQUENCE: 2

Lys Arg Pro Ala Ala Thr Lys Lys Ala Gly Gln Ala Lys Lys Lys Lys
1               5                   10                  15

<210> SEQ ID NO 3
<211> LENGTH: 9
<212> TYPE: PRT
<213> ORGANISM: Homo sapiens

<400> SEQUENCE: 3

Pro Ala Ala Lys Arg Val Lys Leu Asp
1               5

<210> SEQ ID NO 4
<211> LENGTH: 11
<212> TYPE: PRT
<213> ORGANISM: Homo sapiens

<400> SEQUENCE: 4

Arg Gln Arg Arg Asn Glu Leu Lys Arg Ser Pro
1               5                   10

<210> SEQ ID NO 5
<211> LENGTH: 38
<212> TYPE: PRT
<213> ORGANISM: Homo sapiens

<400> SEQUENCE: 5

Asn Gln Ser Ser Asn Phe Gly Pro Met Lys Gly Gly Asn Phe Gly Gly
1               5                   10                  15

Arg Ser Ser Gly Pro Tyr Gly Gly Gly Gly Gln Tyr Phe Ala Lys Pro
            20                  25                  30

Arg Asn Gln Gly Gly Tyr
        35

<210> SEQ ID NO 6
<211> LENGTH: 42
```

<212> TYPE: PRT
<213> ORGANISM: Homo sapiens

<400> SEQUENCE: 6

Arg Met Arg Ile Glx Phe Lys Asn Lys Gly Lys Asp Thr Ala Glu Leu
1               5                   10                  15

Arg Arg Arg Arg Val Glu Val Ser Val Glu Leu Arg Lys Ala Lys Lys
            20                  25                  30

Asp Glu Gln Ile Leu Lys Arg Arg Asn Val
        35                  40

<210> SEQ ID NO 7
<211> LENGTH: 8
<212> TYPE: PRT
<213> ORGANISM: Homo sapiens

<400> SEQUENCE: 7

Val Ser Arg Lys Arg Pro Arg Pro
1               5

<210> SEQ ID NO 8
<211> LENGTH: 8
<212> TYPE: PRT
<213> ORGANISM: Homo sapiens

<400> SEQUENCE: 8

Pro Pro Lys Lys Ala Arg Glu Asp
1               5

<210> SEQ ID NO 9
<211> LENGTH: 8
<212> TYPE: PRT
<213> ORGANISM: Homo sapiens

<400> SEQUENCE: 9

Pro Gln Pro Lys Lys Lys Pro Leu
1               5

<210> SEQ ID NO 10
<211> LENGTH: 12
<212> TYPE: PRT
<213> ORGANISM: Mus sp.

<400> SEQUENCE: 10

Ser Ala Leu Ile Lys Lys Lys Lys Lys Met Ala Pro
1               5                   10

<210> SEQ ID NO 11
<211> LENGTH: 5
<212> TYPE: PRT
<213> ORGANISM: Influenza virus

<400> SEQUENCE: 11

Asp Arg Leu Arg Arg
1               5

<210> SEQ ID NO 12
<211> LENGTH: 7
<212> TYPE: PRT
<213> ORGANISM: Influenza virus

<400> SEQUENCE: 12

Pro Lys Gln Lys Lys Arg Lys
1               5

<210> SEQ ID NO 13
<211> LENGTH: 10
<212> TYPE: PRT
<213> ORGANISM: Hepatitis D virus

<400> SEQUENCE: 13

Arg Lys Leu Lys Lys Lys Ile Lys Lys Leu
1               5                   10

<210> SEQ ID NO 14
<211> LENGTH: 10
<212> TYPE: PRT
<213> ORGANISM: Mus sp.

<400> SEQUENCE: 14

Arg Glu Lys Lys Lys Phe Leu Lys Arg Arg
1               5                   10

<210> SEQ ID NO 15
<211> LENGTH: 20
<212> TYPE: PRT
<213> ORGANISM: Homo sapiens

<400> SEQUENCE: 15

Lys Arg Lys Gly Asp Glu Val Asp Gly Val Asp Glu Val Ala Lys Lys
1               5                   10                  15

Lys Ser Lys Lys
            20

<210> SEQ ID NO 16
<211> LENGTH: 17
<212> TYPE: PRT
<213> ORGANISM: Homo sapiens

<400> SEQUENCE: 16

Arg Lys Cys Leu Gln Ala Gly Met Asn Leu Glu Ala Arg Lys Thr Lys
1               5                   10                  15

Lys

<210> SEQ ID NO 17
<211> LENGTH: 288
<212> TYPE: PRT
<213> ORGANISM: Artificial Sequence
<220> FEATURE:
<223> OTHER INFORMATION: Synthetic N-terminal capping region

<400> SEQUENCE: 17

Met Asp Pro Ile Arg Ser Arg Thr Pro Ser Pro Ala Arg Glu Leu Leu
1               5                   10                  15

Ser Gly Pro Gln Pro Asp Gly Val Gln Pro Thr Ala Asp Arg Gly Val
            20                  25                  30

Ser Pro Pro Ala Gly Gly Pro Leu Asp Gly Leu Pro Ala Arg Arg Thr
        35                  40                  45

Met Ser Arg Thr Arg Leu Pro Ser Pro Ala Pro Ser Pro Ala Phe
    50                  55                  60

Ser Ala Asp Ser Phe Ser Asp Leu Leu Arg Gln Phe Pro Ser Leu
65                  70                  75                  80

Phe Asn Thr Ser Leu Phe Asp Ser Leu Pro Pro Phe Gly Ala His His
                85                  90                  95

Thr Glu Ala Ala Thr Gly Glu Trp Asp Glu Val Gln Ser Gly Leu Arg

```
            100                 105                 110
Ala Ala Asp Ala Pro Pro Thr Met Arg Val Ala Val Thr Ala Ala
            115                 120                 125

Arg Pro Pro Arg Ala Lys Pro Ala Pro Arg Arg Ala Ala Gln Pro
        130                 135                 140

Ser Asp Ala Ser Pro Ala Ala Gln Val Asp Leu Arg Thr Leu Gly Tyr
145                 150                 155                 160

Ser Gln Gln Gln Gln Glu Lys Ile Lys Pro Lys Val Arg Ser Thr Val
                    165                 170                 175

Ala Gln His His Glu Ala Leu Val Gly His Gly Phe Thr His Ala His
                180                 185                 190

Ile Val Ala Leu Ser Gln His Pro Ala Ala Leu Gly Thr Val Ala Val
                195                 200                 205

Lys Tyr Gln Asp Met Ile Ala Ala Leu Pro Glu Ala Thr His Glu Ala
            210                 215                 220

Ile Val Gly Val Gly Lys Gln Trp Ser Gly Ala Arg Ala Leu Glu Ala
225                 230                 235                 240

Leu Leu Thr Val Ala Gly Glu Leu Arg Gly Pro Pro Leu Gln Leu Asp
                    245                 250                 255

Thr Gly Gln Leu Leu Lys Ile Ala Lys Arg Gly Gly Val Thr Ala Val
                260                 265                 270

Glu Ala Val His Ala Trp Arg Asn Ala Leu Thr Gly Ala Pro Leu Asn
                275                 280                 285

<210> SEQ ID NO 18
<211> LENGTH: 183
<212> TYPE: PRT
<213> ORGANISM: Artificial Sequence
<220> FEATURE:
<223> OTHER INFORMATION: Synthetic C-terminal capping region

<400> SEQUENCE: 18

Arg Pro Ala Leu Glu Ser Ile Val Ala Gln Leu Ser Arg Pro Asp Pro
1               5                   10                  15

Ala Leu Ala Ala Leu Thr Asn Asp His Leu Val Ala Leu Ala Cys Leu
            20                  25                  30

Gly Gly Arg Pro Ala Leu Asp Ala Val Lys Lys Gly Leu Pro His Ala
        35                  40                  45

Pro Ala Leu Ile Lys Arg Thr Asn Arg Arg Ile Pro Glu Arg Thr Ser
    50                  55                  60

His Arg Val Ala Asp His Ala Gln Val Val Arg Val Leu Gly Phe Phe
65                  70                  75                  80

Gln Cys His Ser His Pro Ala Gln Ala Phe Asp Asp Ala Met Thr Gln
                85                  90                  95

Phe Gly Met Ser Arg His Gly Leu Leu Gln Leu Phe Arg Arg Val Gly
            100                 105                 110

Val Thr Glu Leu Glu Ala Arg Ser Gly Thr Leu Pro Pro Ala Ser Gln
        115                 120                 125

Arg Trp Asp Arg Ile Leu Gln Ala Ser Gly Met Lys Arg Ala Lys Pro
    130                 135                 140

Ser Pro Thr Ser Thr Gln Thr Pro Asp Gln Ala Ser Leu His Ala Phe
145                 150                 155                 160
```

```
Ala Asp Ser Leu Glu Arg Asp Leu Asp Ala Pro Ser Pro Met His Glu
            165                 170                 175

Gly Asp Gln Thr Arg Ala Ser
            180
```

MYCOBACTERIUM TUBERCULOSIS HOST-PATHOGEN INTERACTION

CROSS REFERENCE TO RELATED APPLICATIONS

This application is a National Stage application of International Application No. PCT/US2018/056168, filed Oct. 16, 2018, which claims the benefit of U.S. Provisional Application No. 62/573,049 filed Oct. 16, 2017. The entire contents of the above-identified application is hereby fully incorporated herein by reference.

REFERENCE TO AN ELECTRONIC SEQUENCE LISTING

The contents of the electronic sequence listing (BROD-2930US.ST25.txt"; Size is 7,843 bytes and it was created on Jan. 6, 2021) is herein incorporated by reference in its entirety.

TECHNICAL FIELD

The subject matter disclosed herein is generally directed to a cell atlas of different cell types in healthy and disease states. The subject matter further relates to novel cell specific and disease specific markers, and to compositions and methods identifying and exploiting target genes or target gene products that modulate, control or otherwise influence cell-cell communication, differential expression, immune response in a variety of therapeutic and/or diagnostic indications, particularly *Mycobacterium tuberculosis*.

BACKGROUND

Immune systems play an essential role in ensuring our health. From decades of laboratory and clinical work, there has been a basic understanding of immune balance and its importance for a healthy immune system. For example, hyperactivity can lead to allergy, inflammation, tissue damage, autoimmune disease and excessive cellular death. On the other hand, immunodeficiency can lead to outgrowth of cancers and the inability to kill or suppress external invaders. The immune system has evolved multiple modalities and redundancies that balance the system, including but not limited to memory, exhaustion, anergy, and senescence. Despite this basic understanding, a comprehensive landscape of immune regulations remains missing. Given the importance of the immune system, a systematic understanding of immune regulations on cell, tissue, and organism levels is crucial for clinicians and researchers to efficiently diagnose and develop treatments for immune system related disease.

Different cells and tissues in a diseased organism are often not impacted at the same level. Analyzing immune regulations with a comprehensive approach allows for identification of cells and tissues that are impacted and that are representative of the disease, interaction between cells, as well as pathways that can be specifically targeted to restore diseased cell or tissues to a normal state. In practice, certain tissues or specimens, for example blood or body fluids, are more easily obtainable than others from a patient. A systematic understanding of immune responses allows clinicians to use easily obtainable tissues as a proxy to diagnose disease and monitor disease state through easily obtainable tissues, and may further allow for treatment or amelioration of symptoms by restoring the state of suppressed immune cells or eliminating severely infected cells, for example, cells impacted with a chronic infection such as *Mycobacterium tuberculosis* (MTB) infected cells.

Tuberculosis is caused by the bacterium *Mycobacterium tuberculosis* (MTB) that preferably affects lungs, but potentially other organs and tissues, especially in immune-suppressed individuals such as young children or people infected with HIV. MTB replicate within macrophages of host tissues, induces cytokines that initiate inflammatory responses and results in granuloma. While some responses are acute, most MTB infections are latent, where the MTB remains in host cells without causing symptoms, which is a crucial barrier to world control of the disease.

However, despite years of clinical work, essential information including location and identity of the pathogen hosting cells or tissues, immunologic response and pathways involved in the infection and response status of such disease-causing infections as HIV/MTB infection remain unclear. A comprehensive understanding focusing on diseased as well as healthy organisms will be able to locates key cells and tissues that represent the disease, location, identity, and phenotype of the disease harboring cells, pathways and mechanisms involved in disease response and pathogen replication, thus help developing diagnosis as well as treatment methods.

Reliable diagnosing of disease states and evaluation of therapies remains problematic. In human subjects, many cell type and tissues are inaccessible to non-invasive methods and further may be difficult to locate and test even where, for example, biopsy procedures are available. Such difficulties extend to non-human animals, including but not limited to non-human primates. For example, animal tissues may be available from animals that cannot be obtained from living human subjects, but such tissues may be inaccessible for other reasons, frequently expense.

SUMMARY

In certain example embodiments, novel markers and networks correlated with *M. tuberculosis* (MTB) copy number in MTB-infected cells are utilized in methods disclosed herein. In some example embodiments, a method of modulating a cell or tissue infected with *Mycobacterium tuberculosis* is provided, comprising contacting the cell or tissue with a modulating agent in an amount sufficient to modify the *Mycobacterium tuberculosis* infection of the cell or tissue as compared to the infection in the absence of the modulating agent.

In an embodiment, the modulating of a cell or tissue comprises modulating a host gene or product of one or more host genes whose expression is increased in a cell infected with *Mycobacterium tuberculosis*. In an embodiment, the one or more host genes encodes a transcription factor, a growth factor, a telomere maintenance factor, or a component of a metabolic pathway. In certain embodiments, the one or more host genes is selected from the genes of Table 1.

In some embodiments, the methods are performed on a cell, in some embodiments, the cell is an immune cell, in a preferred embodiment, the immune cell is a macrophage.

In another embodiment, the modulating of a cell or tissue comprises modulating a host gene or product of one or more host genes whose expression is decreased in a cell infected with *Mycobacterium tuberculosis*. In one embodiment, the one or more host genes encodes a component of apoptosis, vesicle transport, an immune response or a metabolic pathway. In certain embodiments, the one or more host genes is selected from the genes of Table 2

In an embodiment of the invention, the host gene expression is correlated with the copy number of M. tuberculosis in the cell. In some instances, the host gene expression is correlated with the aggregation state and/or copy number.

In an embodiment of the invention, the gene function or gene pathway of the host gene comprises sugar binding, RIG-I-like receptor signaling pathway, cell surface protein, SODD/TNFR1 signaling pathway, interferon-alpha/beta receptor binding, Il-10 signaling, cytosolic DNA-sensing pathway, cytokines, or cyclins and cell cycle regulators. In an embodiment, the host gene comprises REGIP, CD69, CD22, SFTAP1, CD72, IFNA1, IFNA13, DHX58, TRADD, FCER1A, SDC1, CD276, PCSK9, TP53I13, GPC1, BAG4, IL36G, ARG2, IL1F10, MAP4K4, IFNB1, TREX1, CXCL10, IFNA17, HDAC9, CDKN2C, or CCND1. In an embodiment, the host gene is associated with endocytosis or intracellular transport. In an embodiment, the host gene comprises RAB3C, RAC1, APOC1, or NR1H3. In an embodiment of the invention, the host gene is associated with macromolecular complex assembly. In an embodiment of the invention, the host gene comprises TARBP2, TSPYL2, MED27, RAC1, APOC1, H2AFY, NAP1L3, ZW10, or RNF20. In an embodiment, the host gene is associated with chemotaxis, inflammatory response, metabolism, or cell death when infected with aggregates. In some embodiments, the upregulation of genes is indicative of early MTB infection, or in response to aggregates, in some instances, the host genes are CCL4, and/or IL8. In an embodiment genes KCNA2 and CXCL2 significantly upregulated when aggregates are present in a mycobacteria infection.

Methods of diagnosing a cell or tissue in a subject comprising a M. tuberculosis infection comprising detecting a gene expression profile in one or more cells or tissues associated with M. tuberculosis infection, optionally wherein the cell or tissue in the subject and the cell or tissue that is not infected is of the same cell type or tissue type. In some instances, the methods of diagnosing comprise detecting in a subject, and measuring levels of a gene or gene product at one or more time intervals. In some instances, the gene expression profile comprises one or more genes from Table 1, and the method comprises detecting whether the gene expression profile is overexpressed compared to a cell or tissue that is not infected. In some embodiments, the gene expression profile comprises one or more genes from Table 2, and the method comprises detecting whether the gene expression profile is underexpressed compared to a cell or tissue that is not infected. In some instances, the gene expression profile is correlated with the copy number of the M. tuberculosis in the cell. In some embodiments, the methods further comprise treating the infected cell or tissue comprising administering one or more modulating agents as disclosed herein.

Methods of monitoring treatment of a M. tuberculosis infection in a subject is also provided, the method comprising detecting whether one or more genes from Table 2 is underexpressed compared to a subject without infection. In certain embodiments, methods of monitoring treatment of a M. tuberculosis infection in a subject is provided, comprising detecting whether one or more genes from Table 1 is overexpressed compared to a subject without infection. In some instances, the methods of monitoring comprise monitoring in a subject receiving treatment, and measuring levels of a gene or gene product at one or more time intervals. In some instances, the gene expression profile comprises one or more genes from Table 1, and the method comprises detecting whether the gene expression profile is overexpressed compared to a cell or tissue that is not infected. In some embodiments, the gene expression profile comprises one or more genes from Table 2, and the method comprises detecting whether the gene expression profile is underexpressed compared to a cell or tissue that is not infected. In some instances, the gene expression profile is correlated with the copy number of the M. tuberculosis in the cell. Method of monitoring can include a step of administering a modulating agent that modulates the one or more genes from Table 1, the one or more genes from Table 2, or the combination thereof; and subsequently detecting whether the one or more genes from Table 1 is overexpressed compared to a cell that is not infected, detecting whether one or more genes from Table 2 is underexpressed compared to a cell that is not infected, or a combination thereof, wherein the monitoring treatment of the infection is based on changes in expression levels between the initial step of detecting and the subsequent step of detecting.

These and other aspects, objects, features, and advantages of the example embodiments will become apparent to those having ordinary skill in the art upon consideration of the following detailed description of illustrated example embodiments.

BRIEF DESCRIPTION OF THE DRAWINGS

An understanding of the features and advantages of the present invention will be obtained by reference to the following detailed description that sets forth illustrative embodiments, in which the principles of the invention may be utilized, and the accompanying drawings of which:

FIG. 2A Macrophage transcript mapping by macrophage/MTB ratio. FIG. 2B Examples of pathway expression correlated with MTB MOI. FIG. 2C Cellular response to variable copy number of internalized TB indicated by single cells, individually correlated with MTB/cell. FIG. 2D Spearman correlation between MTB/cell and gene expression. FIG. 2E Correlation between MTB/cell and pathway components at low MOI (top) and high MOI (bottom). Gene Set Enrichment Analysis (GSEA) Enrichment P-Value is the statistical significance of the correlation.

FIG. 3—Genes and pathways associated with TB abundance.

FIG. 4A-4B—Expression of macrophage genes and pathways enriched in cells infected with TP singly or as aggregates. FIG. 4A Genes and pathways enriched in cells infected with aggregates (left) or singles (right). FIG. 4B Differential enrichment of cell death (left) and TNF (right) pathways in cells infected as aggregates or singles.

FIG. 19B Certain subsets have equal representation between healthy and SHIV, such as CD8 T cells or macrophages, while CD4 T cells and B cells, show major deviations due to prior SHIV infection, shown in t-SNE plots. FIG. 19C Differential expression of genes in healthy and SHIV-infected CD4 T cells. As in humans, animals with suppressed viral replication as detected in blood show signatures in lymphoid resident T cells associated with ongoing viral replication and response to virus.

FIG. 21A Single cell genomics of cells from lymphoid tissue and ileum compared.

FIG. 21B In the mesenteric LN, T cells are affected by prior HIV infection, but in the ileum, a significant effect is not observed. FIG. 21C In the small intestine, T cells are more similar, but largest differential expression occurs among the epithelial enterocytes. FIG. 21D Identification of cell subsets altered by SHIV infection.

FIG. 23B The most significantly up-regulated genes in aggregates versus uninfected, singles low, and singles high. FIG. 23C charts CCL4 (upper panel) and IL8 (lower panel) were significantly up-regulated in aggregates compared to the other populations indicating an amplified transcriptional response to aggregates.

FIG. 24A-24E MTB Number and Aggregation state determine transcriptional pattern. Differential gene expression between populations of MDMs infected with single Mtb bacilli, many (high) single Mtb bacilli, or Mtb aggregates. FIG. 24A singles high vs. aggregates; FIG. 25C aggregates vs. singles low; FIGS. 25D & 25E Analysis of significant differentially expressed genes in each pairwise comparison reveals genetic programs driven by number of intracellular bacilli only, or driven by aggregation state. FIG. 25D diagrams upregulated genes in singles high vs. singles low and upregulated in high aggregated vs. singles low; FIG. 25E diagrams upregulated genes in singles low vs. singles high and upregulated in singles low vs. high aggregates.

FIG. 25A-25B Genes upregulated by aggregated include key players in the inflammatory response. FIG. 25A charts genes, including those related to cell death regulation and inflammatory response, are upregulated in MDMs infected with aggregates. FIG. 25B Examples of the two patterns observed in differential gene expression: gradual increase in gene expression or strong up regulation in aggregate-infected MDMs.: CXCL1 (upper left panel) KCNA2 (upper right panel), LY9 (lower left panel) and CXCL2 (lower right panel).

Figure 1:
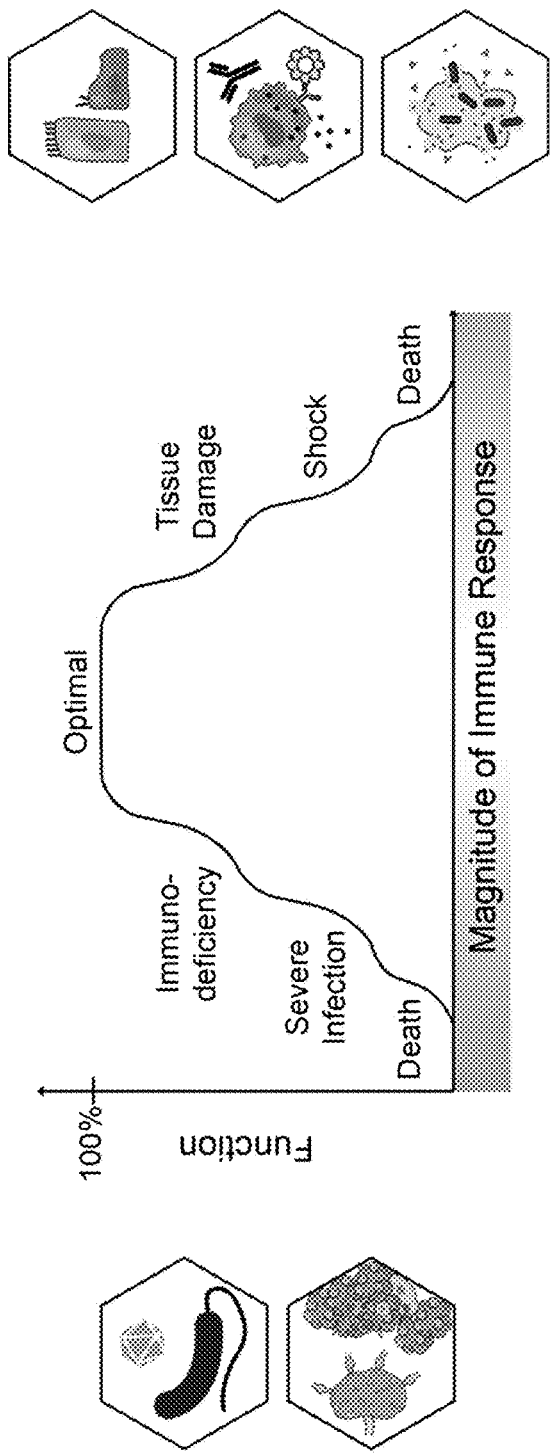
FIG. 1—Balance in the immune system determines health vs. disease. Hyperactivity can lead to tissue damage, allergy, inflammation, and cell death. Immunodeficiency can lead to outgrowth of cancers or external pathogens.

The figures herein are for illustrative purposes only and are not necessarily drawn to scale.

DETAILED DESCRIPTION OF THE EXAMPLE EMBODIMENTS

General Definitions

Unless defined otherwise, technical and scientific terms used herein have the same meaning as commonly understood by one of ordinary skill in the art to which this disclosure pertains. Definitions of common terms and techniques in molecular biology may be found in Molecular Cloning: A Laboratory Manual, $2^{nd}$ edition (1989) (Sambrook, Fritsch, and Maniatis); Molecular Cloning: A Laboratory Manual, $4^{th}$ edition (2012) (Green and Sambrook); Current Protocols in Molecular Biology (1987) (F. M. Ausubel et al. eds.); the series Methods in Enzymology (Academic Press, Inc.): PCR 2: A Practical Approach (1995) (M. J. MacPherson, B. D. Hames, and G. R. Taylor eds.): Antibodies, A Laboratory Manual (1988) (Harlow and Lane, eds.): Antibodies A Laboratory Manual, 2nd edition 2013 (E. A. Greenfield ed.); Animal Cell Culture (1987) (R. I. Freshney, ed.); Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); Robert A. Meyers (ed.), Molecular Biology and Biotechnology: a Comprehensive Desk Reference, published by VCH Publishers, Inc., 1995 (ISBN 9780471185710); Singleton et al., Dictionary of Microbiology and Molecular Biology 2nd ed., J. Wiley & Sons (New York, N.Y. 1994), March, Advanced Organic Chemistry Reactions, Mechanisms and Structure 4th ed., John Wiley & Sons (New York, N.Y. 1992); and Marten H. Hofker and Jan van Deursen, Transgenic Mouse Methods and Protocols, $2^{nd}$ edition (2011).

As used herein, the singular forms "a", "an", and "the" include both singular and plural referents unless the context clearly dictates otherwise.

The term "optional" or "optionally" means that the subsequent described event, circumstance or substituent may or may not occur, and that the description includes instances where the event or circumstance occurs and instances where it does not.

The recitation of numerical ranges by endpoints includes all numbers and fractions subsumed within the respective ranges, as well as the recited endpoints.

The terms "about" or "approximately" as used herein when referring to a measurable value such as a parameter, an amount, a temporal duration, and the like, are meant to encompass variations of and from the specified value, such as variations of +1-10% or less, +/−5% or less, +/−1% or less, and +/−0.1% or less of and from the specified value, insofar such variations are appropriate to perform in the disclosed invention. It is to be understood that the value to which the modifier "about" or "approximately" refers is itself also specifically, and preferably, disclosed.

As used herein, a "biological sample" may contain whole cells and/or live cells and/or cell debris, and can include surgical resections. The biological sample may contain (or be derived from) a "bodily fluid". The present invention encompasses embodiments wherein the bodily fluid is selected from amniotic fluid, aqueous humour, vitreous humour, bile, blood serum, breast milk, cerebrospinal fluid, cerumen (earwax), chyle, chyme, endolymph, perilymph, exudates, feces, female ejaculate, gastric acid, gastric juice, lymph, mucus (including nasal drainage and phlegm), pericardial fluid, peritoneal fluid, pleural fluid, pus, rheum, saliva, sebum (skin oil), semen, sputum, synovial fluid, sweat, tears, urine, vaginal secretion, vomit and mixtures of one or more thereof. Biological samples include cell cultures, bodily fluids, cell cultures from bodily fluids. Bodily fluids may be obtained from a mammal organism, for example by puncture, or other collecting or sampling procedures.

The terms "subject," "individual," and "patient" are used interchangeably herein to refer to a vertebrate, preferably a mammal, more preferably a human. Mammals include, but are not limited to, murines, simians, humans, farm animals, sport animals, and pets. Tissues, cells and their progeny of a biological entity obtained in vivo or cultured in vitro are also encompassed.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s). Reference throughout this specification to "one embodiment", "an embodiment," "an example embodiment," means that a particular feature, structure or characteristic described in connection with the embodiment is included in at least one embodiment of the present invention. Thus, appearances of the phrases "in one embodiment," "in an embodiment," or "an example embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention. For example, in the appended claims, any of the claimed embodiments can be used in any combination.

Reference is made to U.S. provisional application 62/279,500, filed Jan. 15, 2016; and International Patent Application PCT/US2017/013791, filed Jan. 17, 2017.

All publications, published patent documents, and patent applications cited herein are hereby incorporated by reference to the same extent as though each individual publication, published patent document, or patent application was specifically and individually indicated as being incorporated by reference.

Overview

Embodiments disclosed herein provide a pan-tissue cell from healthy and diseased subject. The atlas was obtained by single cell sequencing. The present invention discloses novel markers for cell types. Moreover, genes associated with chronic infection and disease, including tuberculosis (TB) are identified. The invention provides for diagnostic assays based on gene markers and cell composition, as well as therapeutic targets for controlling differentiation, proliferation, maintenance and/or function of the cell types disclosed herein. In addition, novel cell types and methods of quantitating, detecting and isolating the cell types are disclosed.

In certain example embodiment, using Seq-Well (Macosko, E. Z., Basu, A., Satija, R., Nemesh, J., Shekar, K., Goldman, M., Tirosh, L, Bialas, A. R., Kamitaki, N., Marterstock, E. M., Trombetta, J. J., Weitz, D. A., Sanes, J. A., Shalek, A. K., Regev, A., McCarroll, S. A. "Highly Parallel Genome-wide Expression Profiling of Individual Cells Using Nanoliter Droplets" Cell, 161, 1202-1214) for massively parallel scRNA-seq of surgical resections from individuals infected by *Mycobacterium tuberculosis* (MTB+) and healthy individuals (MTB−), cells and tissues representative of infection states were located, and biomarkers related to infection, including indicators of copy number of MTB in specific cells were identified. The methods of detecting gene signatures allow for development of less invasive testing for both acute infection and latent infection.

Method of Modulating

Methods as disclosed herein are directed to modulating a cell or tissue infected with a mycobacteria. The methods comprise contacting a cell or tissue infected with a mycobacteria infection with a modulating agent in an amount sufficient to modify the *mycobacterium* infection of the cell or tissue as compared to the infection in the absence of the modulating agent. The methods of modulating may include modulating one or more host genes, or product of one or more host genes, which may include increasing or decreasing expression of particular host genes or gene products. Modulating may be based on the gene expression detected, and may be additionally be determined by the particular genes, gene products or associated pathways detected. The order of steps provided herein is exemplary, certain steps may be carried out simultaneously or in a different order.

Delivery of Modulating Agents

The contacting may take place in vitro, ex vivo, in vivo. In some instances, contacting can be performed by exposing a cell or tissue to a modulating agent. Administration and delivery of modulating agents in vivo are also contemplated within the step of contacting. The method of contacting will be based on factors such as whether the contacting is performed in vivo, ex vivo, or in vitro, and the gene or gene product to be modulated. Further, methods of contacting may depend on whether the contacting is to be performed over a period of time, for example, continuously via exposure in cell culture or via a multi-dose regiment in vivo, or in one discrete contacting, which may occur with a bolus injection or a discrete exposure to a modulating agent.

Dosage, route of entry, level of infection or copy number of TB per cell may also be factors in the mode of contacting.

Modulating Agent

The modulating agent can be any composition that induces, represses, or otherwise affects a gene or gene product. Modulating agents may be selected in some instances, based on a particular pathway, degree of infection, and/or a gene expression signature that may have been detected.

As used herein, modulating, or to modulate, generally means either reducing or inhibiting the expression or activity of, or alternatively increasing the expression or activity of a target gene. In particular, modulating can mean either reducing or inhibiting the activity of, or alternatively increasing a (relevant or intended) biological activity of, a target or antigen as measured using a suitable in vitro, cellular or in vivo assay (which will usually depend on the target involved), by at least 5%, at least 10%, at least 25%, at least 50%, at least 60%, at least 70%, at least 80%, at least 90%, or more, compared to activity of the target in the same assay under the same conditions but without the presence of an agent. An increase or decrease refers to a statistically significant increase or decrease respectively. For the avoidance of doubt, an increase or decrease will be at least 10% relative to a reference, such as at least 10%, at least 20%, at least 30%, at least 40%, at least 50%, at least 60%, at least 70%, at least 80%, at least 90%, at least 95%, at least 97%, at least 98%, or more, up to and including at least 100% or more, in the case of an increase, for example, at least 2-fold, at least 3-fold, at least 4-fold, at least 5-fold, at least 6-fold, at least 7-fold, at least 8-fold, at least 9-fold, at least 10-fold, at least 50-fold, at least 100-fold, or more. Modulating can also involve effecting a change (which can either be an increase or a decrease) in affinity, avidity, specificity and/or selectivity of a target or antigen, such as a receptor and ligand. Modulating can also mean effecting a change with respect to one or more biological or physiological mechanisms, effects, responses, functions, pathways or activities in which the target or antigen (or in which its substrate(s), ligand(s) or pathway(s) are involved, such as its signaling pathway or metabolic pathway and their associated biological or physiological effects) is involved. Again, as will be clear to the skilled person, such an action as an agonist or an antagonist can be determined in any suitable manner and/or using any suitable assay known or described herein (e.g., in vitro or cellular assay), depending on the target or antigen involved. Accordingly, a modulating agent in an amount sufficient to modify a mycobacteria infection in a cell or tissue would provide the agent in an amount to effect a change in the amount of infection compared to the amount of infection in the cell or tissue in the absence of modulating agent, or untreated. The amount of modulating agent will vary according to the pathway, gene, or gene product targeted, the host, the tissue or cell, and the amount or copy number of the mycobacteria infection.

In certain example embodiments, the agent modulates MTB-infected cells by modulating one or more of the genes listed in Table 1. The genes identified in Table 1 and subsequent tables were determined using scRNA-seq analysis of a combination of healthy control, infected with MTB.

In certain example embodiments, the agent modulates MTB-infected cells by modulating one or more of the genes listed in Table 2. In another example embodiment, the agent modulates MTB-infected cells by modulating one or more of the genes listed in Table 1 (expression induced/increased in MTB+ cells) and/or Table 2 (expression suppressed/decreased in MTB+ cells). Modulating can also depend on copy number in infected cell or tissue, as well as if there is the presence of aggregates. In an embodiment, the host gene is associated with chemotaxis, inflammatory response, metabolism, or cell death when infected with aggregates. In some embodiments, the upregulation of genes is indicative of early MTB infection, or in response to aggregates, in some instances, the host genes are CCL4, and/or IL8. In an embodiment genes KCNA2 and CXCL2 significantly upregulated when aggregates are present in a mycobacteria infection.

Modulating can, for example, also involve allosteric modulation of the target and/or reducing or inhibiting the binding of the target to one of its substrates or ligands and/or competing with a natural ligand, substrate for binding to the target. Modulating can also involve activating the target or the mechanism or pathway in which it is involved. Modulating can for example also involve effecting a change in respect of the folding or confirmation of the target, or in respect of the ability of the target to fold, to change its conformation (for example, upon binding of a ligand), to associate with other (sub)units, or to disassociate. Modulating can for example also involve effecting a change in the ability of the target to signal, phosphorylate, dephosphorylate, and the like.

Protein Binding Agents

As used herein, an agent can refer to a protein-binding agent that permits modulation of activity of proteins or disrupts interactions of proteins and other biomolecules, such as but not limited to disrupting protein-protein interaction, ligand-receptor interaction, or protein-nucleic acid interaction. Agents can also refer to DNA targeting or RNA targeting agents. Agents may include a fragment, derivative and analog of an active agent. The terms "fragment," "derivative" and "analog" when referring to polypeptides as used herein refers to polypeptides which either retain substantially the same biological function or activity as such polypeptides. An analog includes a proprotein which can be activated by cleavage of the proprotein portion to produce an active mature polypeptide. Such agents include, but are not limited to, antibodies ("antibodies" includes antigen-binding portions of antibodies such as epitope- or antigen-binding peptides, paratopes, functional CDRs; recombinant antibodies; chimeric antibodies; humanized antibodies; nanobodies; tribodies; midibodies; or antigen-binding derivatives, analogs, variants, portions, or fragments thereof), protein-binding agents, nucleic acid molecules, small molecules, recombinant protein, peptides, aptamers, avimers and protein-binding derivatives, portions or fragments thereof. An "agent" as used herein, may also refer to an agent that inhibits expression of a gene, such as but not limited to a DNA targeting agent (e.g., CRISPR system, TALE, Zinc finger protein) or RNA targeting agent (e.g., inhibitory nucleic acid molecules such as RNAi, miRNA, ribozyme).

The agents of the present invention may be modified, such that they acquire advantageous properties for therapeutic use (e.g., stability and specificity), but maintain their biological activity.

It is well known that the properties of certain proteins can be modulated by attachment of polyethylene glycol (PEG) polymers, which increases the hydrodynamic volume of the protein and thereby slows its clearance by kidney filtration. (See, e.g., Clark et al., J. Biol. Chem. 271: 21969-21977 (1996)). Therefore, it is envisioned that certain agents can be PEGylated (e.g., on peptide residues) to provide enhanced therapeutic benefits such as, for example, increased efficacy by extending half-life in vivo. In certain embodiments, PEGylation of the agents may be used to extend the serum half-life of the agents and allow for particular agents to be capable of crossing the blood-brain barrier.

In regards to peptide PEGylation methods, reference is made to Lu et al., Int. J. Pept. Protein Res. 43: 127-38 (1994); Lu et al., Pept. Res. 6: 140-6 (1993); Felix et al., Int. J. Pept. Protein Res. 46: 253-64 (1995); Gaertner et al., Bioconjug. Chem. 7: 38-44 (1996); Tsutsumi et al., Thromb. Haemost. 77: 168-73 (1997); Francis et al., hit. J. Hematol. 68: 1-18 (1998); Roberts et al., J. Pharm. Sci. 87: 1440-45 (1998); and Tan et al., Protein Expr. Purif. 12: 45-52 (1998). Polyethylene glycol or PEG is meant to encompass any of the forms of PEG that have been used to derivatize other proteins, including, but not limited to, mono-(C1-10) alkoxy or aryloxy-polyethylene glycol. Suitable PEG moieties include, for example, 40 kDa methoxy poly(ethylene glycol) propionaldehyde (Dow, Midland, Mich.); 60 kDa methoxy poly(ethylene glycol) propionaldehyde (Dow, Midland, Mich.); 40 kDa methoxy poly(ethylene glycol) maleimido-propionamide (Dow, Midland, Mich.); 31 kDa alpha-methyl-w-(3-oxopropoxy), polyoxyethylene (NOF Corporation, Tokyo); mPEG2-NHS-40k (Nektar); mPEG2-MAL-40k (Nektar), SUNBRIGHT GL2-400MA ((PEG)240 kDa) (NOF Corporation, Tokyo), SUNBRIGHT ME-200MA (PEG20 kDa) (NOF Corporation, Tokyo). The PEG groups are generally attached to the peptide (e.g., neuromedin U receptor agonists or antagonists) via acylation or alkylation through a reactive group on the PEG moiety (for example, a maleimide, an aldehyde, amino, thiol, or ester group) to a reactive group on the peptide (for example, an aldehyde, amino, thiol, a maleimide, or ester group).

The PEG molecule(s) may be covalently attached to any Lys, Cys, or K(CO(CH2)2SH) residues at any position in a peptide. In certain embodiments, the neuromedin U receptor agonists described herein can be PEGylated directly to any amino acid at the N-terminus by way of the N-terminal amino group. A "linker arm" may be added to a peptide to facilitate PEGylation. PEGylation at the thiol side-chain of cysteine has been widely reported (see, e.g., Caliceti & Veronese, Adv. Drug Deliv. Rev. 55: 1261-77 (2003)). If there is no cysteine residue in the peptide, a cysteine residue can be introduced through substitution or by adding a cysteine to the N-terminal amino acid.

Substitutions of amino acids may be used to modify an agent of the present invention. The phrase "substitution of amino acids" as used herein encompasses substitution of amino acids that are the result of both conservative and non-conservative substitutions. Conservative substitutions are the replacement of an amino acid residue by another similar residue in a polypeptide. Typical but not limiting conservative substitutions are the replacements, for one another, among the aliphatic amino acids Ala, Val, Leu and Ile; interchange of Ser and Thr containing hydroxy residues, interchange of the acidic residues Asp and Glu, interchange between the amide-containing residues Asn and Gln, interchange of the basic residues Lys and Arg, interchange of the aromatic residues Phe and Tyr, and interchange of the small-sized amino acids Ala, Ser, Thr, Met, and Gly. Non-conservative substitutions are the replacement, in a polypeptide, of an amino acid residue by another residue which is not biologically similar. For example, the replacement of an amino acid residue with another residue that has a substantially different charge, a substantially different hydrophobicity, or a substantially different spatial configuration.

Antibody is used interchangeably with the term immunoglobulin herein, and includes intact antibodies, fragments of antibodies, e.g., Fab, F(ab')2 fragments, and intact antibodies and fragments that have been mutated either in their constant and/or variable region (e.g., mutations to produce chimeric, partially humanized, or fully humanized antibodies, as well as to produce antibodies with a desired trait, e.g., enhanced binding and/or reduced FcR binding). The term "fragment" refers to a part or portion of an antibody or antibody chain comprising fewer amino acid residues than an intact or complete antibody or antibody chain. Fragments can be obtained via chemical or enzymatic treatment of an intact or complete antibody or antibody chain. Fragments can also be obtained by recombinant means. Exemplary fragments include Fab, Fab', F(ab')2, Fabc, Fd, dAb, VHH and scFv and/or Fv fragments.

As used herein, a preparation of antibody protein having less than about 50% of non-antibody protein (also referred to herein as a "contaminating protein"), or of chemical precursors, is considered to be "substantially free." 40%, 30%, 20%, 10% and more preferably 5% (by dry weight), of non-antibody protein, or of chemical precursors is considered to be substantially free. When the antibody protein or biologically active portion thereof is recombinantly produced, it is also preferably substantially free of culture medium, i.e., culture medium represents less than about 30%, preferably less than about 20%, more preferably less than about 10%, and most preferably less than about 5% of the volume or mass of the protein preparation.

An antigen-binding fragment refers to a polypeptide fragment of an immunoglobulin or antibody that binds antigen or competes with intact antibody (i.e., with the intact antibody from which they were derived) for antigen binding (i.e., specific binding). As such these antibodies or fragments thereof are included in the scope of the invention, provided that the antibody or fragment binds specifically to a target molecule.

It is intended that the term antibody encompass any Ig class or any Ig subclass (e.g. the IgG1, IgG2, IgG3, and IgG4 subclasses of IgG) obtained from any source (e.g., humans and non-human primates, and in rodents, lagomorphs, caprines, bovines, equines, ovines, etc.).

The term "Ig class" or immunoglobulin class, as used herein, refers to the five classes of immunoglobulin that have been identified in humans and higher mammals, IgG, IgM, IgA, IgD, and IgE. The term "Ig subclass" refers to the two subclasses of IgM (H and L), three subclasses of IgA (IgA1, IgA2, and secretory IgA), and four subclasses of IgG (IgG1, IgG2, IgG3, and IgG4) that have been identified in humans and higher mammals. The antibodies can exist in monomeric or polymeric form; for example, lgM antibodies exist in pentameric form, and IgA antibodies exist in monomeric, dimeric or multimeric form.

IgG subclass refers to the four subclasses of immunoglobulin class IgG—IgG1, IgG2, IgG3, and IgG4 that have been identified in humans and higher mammals by the heavy chains of the immunoglobulins, V1-γ4, respectively. The term single-chain immunoglobulin or single-chain antibody (used interchangeably herein) refers to a protein having a two-polypeptide chain structure consisting of a heavy and a light chain, said chains being stabilized, for example, by interchain peptide linkers, which has the ability to specifically bind antigen. The term domain refers to a globular region of a heavy or light chain polypeptide comprising peptide loops (e.g., comprising 3 to 4 peptide loops) stabilized, for example, by β pleated sheet and/or intrachain disulfide bond. Domains are further referred to herein as "constant" or "variable", based on the relative lack of sequence variation within the domains of various class members in the case of a "constant" domain, or the significant variation within the domains of various class members in the case of a "variable" domain. Antibody or polypeptide "domains" are often referred to interchangeably in the art as antibody or polypeptide "regions". The "constant" domains of an antibody light chain are referred to interchangeably as "light chain constant regions", "light chain constant domains", "CL" regions or "CL" domains. The "constant" domains of an antibody heavy chain are referred to interchangeably as "heavy chain constant regions", "heavy chain constant domains", "CH" regions or "CH" domains). The "variable" domains of an antibody light chain are referred to interchangeably as "light chain variable regions", "light chain variable domains", "VL" regions or "VL" domains). The variable domains of an antibody heavy chain are referred to interchangeably as heavy chain constant regions, heavy chain constant domains, "VH" regions or "VH" domains).

A region can also refer to a part or portion of an antibody chain or antibody chain domain (e.g., a part or portion of a heavy or light chain or a part or portion of a constant or variable domain, as defined herein), as well as more discrete parts or portions of said chains or domains. For example, light and heavy chains or light and heavy chain variable domains include "complementarity determining regions" or "CDRs" interspersed among "framework regions" or "FRs", as defined herein.

Conformation refers to the tertiary structure of a protein or polypeptide (e.g., an antibody, antibody chain, domain or region thereof). For example, light (or heavy) chain conformation can refer to the tertiary structure of a light (or heavy) chain variable region, and the antibody conformation or antibody fragment conformation refers to the tertiary structure of an antibody or fragment thereof.

The term "antibody-like protein scaffolds" or "engineered protein scaffolds" broadly encompasses proteinaceous non-immunoglobulin specific-binding agents, typically obtained by combinatorial engineering (such as site-directed random mutagenesis in combination with phage display or other molecular selection techniques). Usually, such scaffolds are derived from robust and small soluble monomeric proteins (such as Kunitz inhibitors or lipocalins) or from a stably folded extra-membrane domain of a cell surface receptor (such as protein A, fibronectin or the ankyrin repeat).

Such scaffolds have been extensively reviewed in Binz et al. (Engineering novel binding proteins from nonimmunoglobulin domains. Nat Biotechnol 2005, 23:1257-1268), Gebauer and Skerra (Engineered protein scaffolds as next-generation antibody therapeutics. Curr Opin Chem Biol. 2009, 13:245-55), Gill and Damle (Biopharmaceutical drug discovery using novel protein scaffolds. Curr Opin Biotechnol 2006, 17:653-658), Skerra (Engineered protein scaffolds for molecular recognition. J Mol Recognit 2000, 13:167-187), and Skerra (Alternative non-antibody scaffolds for molecular recognition. Curr Opin Biotechnol 2007, 18:295-304), and include without limitation affibodies, based on the Z-domain of staphylococcal protein A, a three-helix bundle of 58 residues providing an interface on two of its alpha-helices (Nygren, Alternative binding proteins: Affibody binding proteins developed from a small three-helix bundle scaffold. FEBS J 2008, 275:2668-2676); engineered Kunitz domains based on a small (ca. 58 residues) and robust, disulphide-crosslinked serine protease inhibitor, typically of human origin (e.g. LACI-D1), which can be engineered for different protease specificities (Nixon and Wood, Engineered protein inhibitors of proteases. Curr Opin Drug Discov Dev 2006, 9:261-268); monobodies or adnectins based on the 10th extracellular domain of human fibronectin III (10Fn3), which adopts an Ig-like beta-sandwich fold (94 residues) with 2-3 exposed loops, but lacks the central disulphide bridge (Koide and Koide, Monobodies: antibody mimics based on the scaffold of the fibronectin type III domain. Methods Mol Biol 2007, 352:95-109); anticalins derived from the lipocalins, a diverse family of eight-stranded beta-barrel proteins (ca. 180 residues) that naturally form binding sites for small ligands by means of four structurally variable loops at the open end, which are abundant in humans, insects, and many other organisms (Skerra, Alternative binding proteins: Anticalins—harnessing the structural plasticity of the lipocalin ligand pocket to engineer novel binding activities. FEBS J 2008, 275:2677-2683); DARPins, designed ankyrin repeat domains (166 residues), which provide a rigid interface arising from typically three repeated beta-turns (Stumpp et al., DARPins: a new generation of protein therapeutics. Drug Discov Today 2008, 13:695-701); avimers (multimerized LDLR-A module) (Silverman et al., Multivalent avimer proteins evolved by exon shuffling of a family of human receptor domains. Nat Biotechnol 2005, 23:1556-1561); and cysteine-rich knottin peptides (Kolmar, Alternative binding proteins: biological activity and therapeutic potential of cystine-knot miniproteins. FEBS J 2008, 275:2684-2690).

"Specific binding" of an antibody means that the antibody exhibits appreciable affinity for a particular antigen or epitope and, generally, does not exhibit significant cross reactivity. "Appreciable" binding includes binding with an affinity of at least 25 µM. Antibodies with affinities greater than $1\times10^7$ $M^{-1}$ (or a dissociation coefficient of 1 µM or less or a dissociation coefficient of 1 nm or less) typically bind with correspondingly greater specificity. Values intermediate of those set forth herein are also intended to be within the scope of the present invention and antibodies of the invention bind with a range of affinities, for example, 100 nM or less, 75 nM or less, 50 nM or less, 25 nM or less, for example 10 nM or less, 5 nM or less, 1 nM or less, or in embodiments 500 pM or less, 100 pM or less, 50 pM or less or 25 pM or less. An antibody that "does not exhibit significant crossreactivity" is one that will not appreciably bind to an entity other than its target (e.g., a different epitope or a different molecule). For example, an antibody that specifically binds to a target molecule will appreciably bind the target molecule but will not significantly react with non-target molecules or peptides. An antibody specific for a particular epitope will, for example, not significantly cross-react with remote epitopes on the same protein or peptide. Specific binding can be determined according to any art-recognized means for determining such binding. Preferably, specific binding is determined according to Scatchard analysis and/or competitive binding assays.

As used herein, the term "affinity" refers to the strength of the binding of a single antigen-combining site with an antigenic determinant. Affinity depends on the closeness of stereochemical fit between antibody combining sites and antigen determinants, on the size of the area of contact between them, on the distribution of charged and hydrophobic groups, etc. Antibody affinity can be measured by equilibrium dialysis or by the kinetic BIACORE™ method. The dissociation constant, Kd, and the association constant, Ka, are quantitative measures of affinity.

As used herein, the term "monoclonal antibody" refers to an antibody derived from a clonal population of antibody-producing cells (e.g., B lymphocytes or B cells) which is homogeneous in structure and antigen specificity. The term "polyclonal antibody" refers to a plurality of antibodies originating from different clonal populations of antibody-producing cells which are heterogeneous in their structure and epitope specificity but which recognize a common antigen. Monoclonal and polyclonal antibodies may exist within bodily fluids, as crude preparations, or may be purified, as described herein.

The term "binding portion" of an antibody (or "antibody portion") includes one or more complete domains, e.g., a pair of complete domains, as well as fragments of an antibody that retain the ability to specifically bind to a target molecule. It has been shown that the binding function of an antibody can be performed by fragments of a full-length antibody. Binding fragments are produced by recombinant DNA techniques, or by enzymatic or chemical cleavage of intact immunoglobulins. Binding fragments include Fab, Fab', F(ab')2, Fabc, Fd, dAb, Fv, single chains, single-chain antibodies, e.g., scFv, and single domain antibodies.

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, FR residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable regions correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin.

Examples of portions of antibodies or epitope-binding proteins encompassed by the present definition include: (i) the Fab fragment, having $V_L$, $C_L$, $V_H$ and $C_H1$ domains; (ii) the Fab' fragment, which is a Fab fragment having one or more cysteine residues at the C-terminus of the $C_H1$ domain; (iii) the Fd fragment having $V_H$ and $C_H1$ domains; (iv) the Fd' fragment having $V_H$ and $C_H1$ domains and one or more cysteine residues at the C-terminus of the CHI domain; (v) the Fv fragment having the $V_L$ and $V_H$ domains of a single arm of an antibody; (vi) the dAb fragment (Ward et al., 341 Nature 544 (1989)) which consists of a $V_H$ domain or a $V_L$ domain that binds antigen; (vii) isolated CDR regions or isolated CDR regions presented in a functional framework; (viii) F(ab')2 fragments which are bivalent fragments including two Fab' fragments linked by a disulphide bridge at the hinge region; (ix) single chain antibody molecules (e.g., single chain Fv; scFv) (Bird et al., 242 Science 423 (1988); and Huston et al., 85 PNAS 5879 (1988)); (x) "diabodies" with two antigen binding sites, comprising a heavy chain variable domain ($V_H$) connected to a light chain variable domain ($V_L$) in the same polypeptide chain (see, e.g., EP 404,097; WO 93/11161; Hollinger et al., 90 PNAS 6444 (1993)); (xi) "linear antibodies" comprising a pair of tandem Fd segments ($V_H$-$C_h1$-$V_H$-$C_h1$) which, together with complementary light chain polypeptides, form a pair of antigen binding regions (Zapata et al., Protein Eng. 8(10): 1057-62 (1995); and U.S. Pat. No. 5,641,870).

As used herein, a blocking antibody or an antibody antagonist is one which inhibits or reduces biological activity of the antigen(s) it binds. In certain embodiments, the blocking antibodies or antagonist antibodies or portions thereof described herein completely inhibit the biological activity of the antigen(s).

Antibodies may act as agonists or antagonists of the recognized polypeptides. For example, the present invention includes antibodies which disrupt receptor/ligand interactions either partially or fully. The invention features both receptor-specific antibodies and ligand-specific antibodies. The invention also features receptor-specific antibodies which do not prevent ligand binding but prevent receptor activation. Receptor activation (i.e., signaling) may be determined by techniques described herein or otherwise known in the art. For example, receptor activation can be determined by detecting the phosphorylation (e.g., tyrosine or serine/threonine) of the receptor or of one of its down-stream substrates by immunoprecipitation followed by western blot analysis. In specific embodiments, antibodies are provided that inhibit ligand activity or receptor activity by at least 95%, at least 90%, at least 85%, at least 80%, at least 75%, at least 70%, at least 60%, or at least 50% of the activity in absence of the antibody.

The invention also features receptor-specific antibodies which both prevent ligand binding and receptor activation as well as antibodies that recognize the receptor-ligand complex. Likewise, encompassed by the invention are neutralizing antibodies which bind the ligand and prevent binding of the ligand to the receptor, as well as antibodies which bind the ligand, thereby preventing receptor activation, but do not prevent the ligand from binding the receptor. Further included in the invention are antibodies which activate the receptor. These antibodies may act as receptor agonists, i.e., potentiate or activate either all or a subset of the biological activities of the ligand-mediated receptor activation, for example, by inducing dimerization of the receptor. The antibodies may be specified as agonists, antagonists or inverse agonists for biological activities comprising the specific biological activities of the peptides disclosed herein. The antibody agonists and antagonists can be made using methods known in the art. See, e.g., PCT publication WO 96/40281; U.S. Pat. No. 5,811,097; Deng et al., Blood 92(6):1981-1988 (1998); Chen et al., Cancer Res. 58(16): 3668-3678 (1998); Harrop et al., J. Immunol. 161(4):1786-1794 (1998); Zhu et al., Cancer Res. 58(15):3209-3214 (1998); Yoon et al., J. Immunol. 160(7):3170-3179 (1998); Prat et al., J. Cell. Sci. III (Pt2):237-247 (1998); Pitard et al., J. Immunol. Methods 205(2):177-190 (1997); Liautard et al., Cytokine 9(4):233-241 (1997); Carlson et al., J. Biol. Chem. 272(17):11295-11301 (1997); Taryman et al., Neuron 14(4): 755-762 (1995); Muller et al., Structure 6(9):1153-1167 (1998); Bartunek et al., Cytokine 8(1):14-20 (1996).

The antibodies as defined for the present invention include derivatives that are modified, i.e., by the covalent attachment of any type of molecule to the antibody such that covalent attachment does not prevent the antibody from generating an anti-idiotypic response. For example, but not by way of limitation, the antibody derivatives include antibodies that have been modified, e.g., by glycosylation, acetylation, pegylation, phosphylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

Simple binding assays can be used to screen for or detect agents that bind to a target protein, or disrupt the interaction between proteins (e.g., a receptor and a ligand). Because certain targets of the present invention are transmembrane proteins, assays that use the soluble forms of these proteins rather than full-length protein can be used, in some embodiments. Soluble forms include, for example, those lacking the transmembrane domain and/or those comprising the IgV domain or fragments thereof which retain their ability to bind their cognate binding partners. Further, agents that inhibit or enhance protein interactions for use in the compositions and methods described herein, can include recombinant peptido-mimetics.

Detection methods useful in screening assays include antibody-based methods, detection of a reporter moiety, detection of cytokines as described herein, and detection of a gene signature as described herein.

Another variation of assays to determine binding of a receptor protein to a ligand protein is through the use of affinity biosensor methods. Such methods may be based on the piezoelectric effect, electrochemistry, or optical methods, such as ellipsometry, optical wave guidance, and surface plasmon resonance (SPR).

Nucleic Acid Molecules

The disclosure also encompasses nucleic acid molecules, in particular those that inhibit a signature gene. Exemplary nucleic acid molecules include aptamers, siRNA, artificial microRNA, interfering RNA or RNAi, dsRNA, ribozymes, antisense oligonucleotides, and DNA expression cassettes encoding said nucleic acid molecules. Preferably, the nucleic acid molecule is an antisense oligonucleotide. Antisense oligonucleotides (ASO) generally inhibit their target by binding target mRNA and sterically blocking expression by obstructing the ribosome. ASOs can also inhibit their target by binding target mRNA thus forming a DNA-RNA hybrid that can be a substance for RNase H. Preferred ASOs include Locked Nucleic Acid (LNA), Peptide Nucleic Acid (PNA), and morpholinos Preferably, the nucleic acid molecule is an RNAi molecule, i.e., RNA interference molecule. Preferred RNAi molecules include siRNA, shRNA, and artificial miRNA. The design and production of siRNA molecules is well known to one of skill in the art (e.g., Hajeri P B, Singh S K. Drug Discov Today. 2009 14(17-18):851-8). The nucleic acid molecule inhibitors may be chemically synthesized and provided directly to cells of interest. The nucleic acid compound may be provided to a cell as part of a gene delivery vehicle. Such a vehicle is preferably a liposome or a viral gene delivery vehicle.

Small Molecule

In certain embodiments, the one or more agents is a small molecule. The term "small molecule" refers to compounds, preferably organic compounds, with a size comparable to those organic molecules generally used in pharmaceuticals. The term excludes biological macromolecules (e.g., proteins, peptides, nucleic acids, etc.). Preferred small organic molecules range in size up to about 5000 Da, e.g., up to about 4000, preferably up to 3000 Da, more preferably up to 2000 Da, even more preferably up to about 1000 Da, e.g., up to about 900, 800, 700, 600 or up to about 500 Da. In certain embodiments, the small molecule may act as an antagonist or agonist (e.g., blocking an enzyme active site or activating a receptor by binding to a ligand binding site).

One type of small molecule applicable to the present invention is a degrader molecule. Proteolysis Targeting Chimera (PROTAC) technology is a rapidly emerging alternative therapeutic strategy with the potential to address many of the challenges currently faced in modern drug development programs. PROTAC technology employs small molecules that recruit target proteins for ubiquitination and removal by the proteasome (see, e.g., Bondeson and Crews, Targeted Protein Degradation by Small Molecules, Annu Rev Pharmacol Toxicol. 2017 Jan. 6; 57: 107-123; and Lai et al., Modular PROTAC Design for the Degradation of Oncogenic BCR-ABL Angew Chem Int Ed Engl. 2016 Jan. 11; 55(2): 807-810). Accordingly, in certain embodiments, the one or more agents comprises a small molecule inhibitor, small molecule degrader (e.g., PROTAC), genetic modifying agent, antibody, antibody fragment, antibody-like protein scaffold, aptamer, protein, or any combination thereof.

As described herein, small molecules targeting epigenetic proteins are currently being developed and/or used in the clinic to treat disease (see, e.g., Qi et al., HEDD: the human epigenetic drug database. Database, 2016, 1-10; and Ackloo et al., Chemical probes targeting epigenetic proteins: Applications beyond oncology. Epigenetics 2017, VOL. 12, NO. 5, 378-400). In certain embodiments, the one or more agents comprise a histone acetylation inhibitor, histone deacetylase (HDAC) inhibitor, histone lysine methylation inhibitor, histone lysine demethylation inhibitor, DNA methyltransferase (DNMT) inhibitor, inhibitor of acetylated histone binding proteins, inhibitor of methylated histone binding proteins, sirtuin inhibitor, protein arginine methyltransferase inhibitor or kinase inhibitor. In certain embodiments, any small molecule exhibiting the functional activity described above may be used in the present invention. In certain embodiments, the DNA methyltransferase (DNMT) inhibitor is selected from the group consisting of azacitidine (5-azacytidine), decitabine (5-aza-2'-deoxycytidine), EGCG (epigallocatechin gallate), zebularine, hydralazine, and procainamide. In certain embodiments, the histone acetylation inhibitor is C646. In certain embodiments, the histone deacetylase (HDAC) inhibitor is selected from the group consisting of vorinostat, givinostat, panobinostat, belinostat, entinostat, CG-1521, romidepsin, ITF-A, ITF-B, valproic acid, OSU-HDAC-44, HC-toxin, magnesium valproate, plitidepsin, tasquinimod, sodium butyrate, mocetinostat, carbamazepine, SB939, CHR-2845, CHR-3996, JNJ-26481585, sodium phenylbutyrate, pivanex, abexinostat, resminostat, dacinostat, droxinostat, and trichostatin A (TSA). In certain embodiments, the histone lysine demethylation inhibitor is selected from the group consisting of pargyline, clorgyline, bizine, GSK2879552, GSK-J4, KDMS-C70, JIB-04, and tranylcypromine. In certain embodiments, the histone lysine methylation inhibitor is selected from the group consisting of EPZ-6438, GSK126, CPI-360, CPI-1205, CPI-0209, DZNep, GSK343, EI1, BIX-01294, UNC0638, EPZ004777, GSK343, UNC1999 and UNCO224. In certain embodiments, the inhibitor of acetylated histone binding proteins is selected from the group consisting of AZD5153 (see e.g., Rhyasen et al., AZD5153: A Novel Bivalent BET Bromodomain Inhibitor Highly Active against Hematologic Malignancies, Mol Cancer Ther. 2016 November; 15(11):2563-2574. Epub 2016 Aug. 29), PFI-1, CPI-203, CPI-0610, RVX-208, OTX015, I-BET151, I-BET762, I-BET-726, dBET1, ARV-771, ARV-825, BETd-260/ZBC260 and MZ1. In certain embodiments, the inhibitor of methylated histone binding proteins is selected from the group consisting of UNC669 and UNC1215. In certain embodiments, the sirtuin inhibitor comprises nicotinamide.

As detailed herein, modulate broadly denotes a qualitative and/or quantitative alteration, change or variation in that which is being modulated. Where modulation can be assessed quantitatively—for example, where modulation comprises or consists of a change in a quantifiable variable such as a quantifiable property of a cell or where a quantifiable variable provides a suitable surrogate for the modulation—modulation specifically encompasses both increase (e.g., activation) or decrease (e.g., inhibition) in the measured variable. The term encompasses any extent of such modulation, e.g., any extent of such increase or decrease, and may more particularly refer to statistically significant increase or decrease in the measured variable. The modulating agents can be used in an amount sufficient to modify an infection, a change in the amount or degree of infection as compared to in the absence of infection. By means of example, modulation may encompass an increase in the value of the measured variable by at least about 10%, e.g., by at least about 20%, preferably by at least about 30%, e.g., by at least about 40%, more preferably by at least about 50%, e.g., by at least about 75%, even more preferably by at least about 100%, e.g., by at least about 150%, 200%, 250%, 300%, 400% or by at least about 500%, compared to a reference situation without said modulation; or modulation may encompass a decrease or reduction in the value of the measured variable by at least about 10%, e.g., by at least about 20%, by at least about 30%, e.g., by at least about 40%, by at least about 50%, e.g., by at least about 60%, by at least about 70%, e.g., by at least about 80%, by at least about 90%, e.g., by at least about 95%, such as by at least about 96%, 97%, 98%, 99% or even by 100%, compared to a reference situation without said modulation. Preferably, modulation may be specific or selective, hence, one or more desired phenotypic aspects of a cell, cell population, or tissue, or any other infected cell or tissue may be modulated without substantially altering other (unintended, undesired) phenotypic aspect(s).

As further detailed herein, an agent broadly encompasses any condition, substance or agent capable of modulating one or more phenotypic aspects of cell or cell population as disclosed herein. Such conditions, substances or agents may be of physical, chemical, biochemical and/or biological nature. A candidate agent refers to any condition, substance or agent that is being examined for the ability to modulate one or more phenotypic aspects of a cell or cell population as disclosed herein in a method comprising applying the candidate agent to the cell or cell population (e.g., exposing the cell, cell population, or tissue to the candidate agent or contacting the cell, cell population, or tissue with the candidate agent) and observing whether the desired modulation takes place. In some instances, the cell population comprises immune cells, in some embodiments, the cell population comprises macrophages.

Agents may include any potential class of biologically active conditions, substances or agents, such as for instance antibodies, proteins, peptides, nucleic acids, oligonucleotides, small molecules, or combinations thereof.

By means of example but without limitation, agents can include low molecular weight compounds, but may also be larger compounds, or any organic or inorganic molecule effective in the given situation, including modified and unmodified nucleic acids such as antisense nucleic acids, RNAi, such as siRNA or shRNA, CRISPR/Cas systems, peptides, peptidomimetics, receptors, ligands, and antibodies, aptamers, polypeptides, nucleic acid analogues or variants thereof. Examples include an oligomer of nucleic acids, amino acids, or carbohydrates including without limitation proteins, oligonucleotides, ribozymes, DNAzymes, glycoproteins, siRNAs, lipoproteins, aptamers, and modifications and combinations thereof. Agents can be selected from a group comprising: chemicals; small molecules; nucleic acid sequences; nucleic acid analogues; proteins; peptides; aptamers; antibodies; or fragments thereof. A nucleic acid sequence can be RNA or DNA, and can be single or double stranded, and can be selected from a group comprising; nucleic acid encoding a protein of interest, oligonucleotides, nucleic acid analogues, for example peptide—nucleic acid (PNA), pseudo-complementary PNA (pc-PNA), locked nucleic acid (LNA), modified RNA (mod-RNA), single guide RNA etc. Such nucleic acid sequences include, for example, but are not limited to, nucleic acid sequence encoding proteins, for example that act as transcriptional repressors, antisense molecules, ribozymes, small inhibitory nucleic acid sequences, for example but are not limited to RNAi, shRNAi, siRNA, micro RNAi (mRNAi), antisense oligonucleotides, CRISPR guide RNA, for example that target a CRISPR enzyme to a specific DNA target sequence etc. A protein and/or peptide or fragment thereof can be any protein of interest, for example, but are not limited to: mutated proteins; therapeutic proteins and truncated proteins, wherein the protein is normally absent or expressed at lower levels in the cell. Proteins can also be selected from a group comprising; mutated proteins, genetically engineered proteins, peptides, synthetic peptides, recombinant proteins, chimeric proteins, antibodies, midibodies, minibodies, triabodies, humanized proteins, humanized antibodies, chimeric antibodies, modified proteins and fragments thereof. Alternatively, the agent can be intracellular within the cell as a result of introduction of a nucleic acid sequence into the cell and its transcription resulting in the production of the nucleic acid and/or protein modulator of a gene within the cell. In some embodiments, the agent is any chemical, entity or moiety, including without limitation synthetic and naturally-occurring non-proteinaceous entities. In certain embodiments, the agent is a small molecule having a chemical moiety. Agents can be known to have a desired activity and/or property, or can be selected from a library of diverse compounds.

Hormones, Cytokines, Growth Factors

In certain embodiments, an agent may be a hormone, a cytokine, a lymphokine, a growth factor, a chemokine, a cell surface receptor ligand such as a cell surface receptor agonist or antagonist, or a mitogen.

Non-limiting examples of hormones include growth hormone (GH), adrenocorticotropic hormone (ACTH), dehydroepiandrosterone (DHEA), cortisol, epinephrine, thyroid hormone, estrogen, progesterone, testosterone, or combinations thereof.

Non-limiting examples of cytokines include lymphokines (e.g., interferon-γ, IL-2, IL-3, IL-4, IL-6, granulocyte-macrophage colony-stimulating factor (GM-CSF), interferon-γ, leukocyte migration inhibitory factors (T-LIF, B-LIF), lymphotoxin-alpha, macrophage-activating factor (MAF), macrophage migration-inhibitory factor (MIF), neuroleukin, immunologic suppressor factors, transfer factors, or combinations thereof), monokines (e.g., IL-1, TNF-alpha, interferon-α, interferon-β, colony stimulating factors, e.g., CSF2, CSF3, macrophage CSF or GM-CSF, or combinations thereof), chemokines (e.g., beta-thromboglobulin, C chemokines, CC chemokines, CXC chemokines, CX3C chemokines, macrophage inflammatory protein (MIP), or combinations thereof), interleukins (e.g., IL-1, IL-2, IL-3, IL-4, IL-5, IL-6, IL-7, IL-8, IL-9, IL-10, IL-11, IL-12, IL-13, IL-14, IL-15, IL-17, IL-18, IL-19, IL-20, IL-21, IL-22, IL-23, IL-24, IL-25, IL-26, IL-27, IL-28, IL-29, IL-30, IL-31, IL-32, IL-33, IL-34, IL-35, IL-36, or combinations thereof), and several related signaling molecules, such as tumour necrosis factor (TNF) and interferons (e.g., interferon-α, interferon-β, interferon-γ, interferon-λ, or combinations thereof).

Non-limiting examples of growth factors include those of fibroblast growth factor (FGF) family, bone morphogenic protein (BMP) family, platelet derived growth factor (PDGF) family, transforming growth factor beta (TGFbeta) family, nerve growth factor (NGF) family, epidermal growth factor (EGF) family, insulin related growth factor (IGF) family, hepatocyte growth factor (HGF) family, hematopoietic growth factors (HeGFs), platelet-derived endothelial cell growth factor (PD-ECGF), angiopoietin, vascular endothelial growth factor (VEGF) family, glucocorticoids, or combinations thereof.

Non-limiting examples of mitogens include phytohaemagglutinin (PHA), concanavalin A (conA), lipopolysaccharide (LPS), pokeweed mitogen (PWM), phorbol ester such as phorbol myristate acetate (PMA) with or without ionomycin, or combinations thereof.

Non-limiting examples of cell surface receptors the ligands of which may act as agents include Toll-like receptors (TLRs) (e.g., TLR1, TLR2, TLR3, TLR4, TLR5, TLR6, TLR7, TLR8, TLR9, TLR10, TLR11, TLR12 or TLR13), CD80, CD86, CD40, CCR7, or C-type lectin receptors.

Pharmaceutical Compositions

Pharmaceutical compositions or vaccines are also contemplated within the scope of the disclosure. One aspect of the invention provides for a composition, pharmaceutical composition or vaccine directed to MTB infected cells.

A "pharmaceutical composition" refers to a composition that usually contains an excipient, such as a pharmaceutically acceptable carrier that is conventional in the art and that is suitable for administration to cells or to a subject. Pharmaceutically acceptable as used throughout this specification is consistent with the art and means compatible with the other ingredients of a pharmaceutical composition and not deleterious to the recipient thereof.

As used herein, "carrier" or "excipient" includes any and all solvents, diluents, buffers (such as, e.g., neutral buffered saline or phosphate buffered saline), solubilisers, colloids, dispersion media, vehicles, fillers, chelating agents (such as, e.g., EDTA or glutathione), amino acids (such as, e.g., glycine), proteins, disintegrants, binders, lubricants, wetting agents, emulsifiers, sweeteners, colorants, flavourings, aromatisers, thickeners, agents for achieving a depot effect, coatings, antifungal agents, preservatives, stabilisers, antioxidants, tonicity controlling agents, absorption delaying agents, and the like. The use of such media and agents for pharmaceutical active components is well known in the art. Such materials should be non-toxic and should not interfere with the activity of the cells or active components.

The precise nature of the carrier or excipient or other material will depend on the route of administration. For example, the composition may be in the form of a parenterally acceptable aqueous solution, which is pyrogen-free and has suitable pH, isotonicity and stability. For general principles in medicinal formulation, the reader is referred to Cell Therapy: Stem Cell Transplantation, Gene Therapy, and Cellular Immunotherapy, by G. Morstyn & W. Sheridan eds., Cambridge University Press, 1996; and Hematopoietic Stem Cell Therapy, E. D. Ball, J. Lister & P. Law, Churchill Livingstone, 2000.

It will be appreciated that administration of therapeutic entities in accordance with the invention will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences (15th ed, Mack Publishing Company, Easton, Pa. (1975)), particularly Chapter 87 by Blaug, Seymour, therein. These formulations include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the present invention, provided that the active ingredient in the formulation is not inactivated by the formulation and the formulation is physiologically compatible and tolerable with the route of administration. See also Baldrick P. "Pharmaceutical excipient development: the need for preclinical guidance." Regul. Toxicol Pharmacol. 32(2):210-8 (2000), Wang W. "Lyophilization and development of solid protein pharmaceuticals." Int. J. Pharm. 203(1-2):1-60 (2000), Charman W N "Lipids, lipophilic drugs, and oral drug delivery-some emerging concepts." J Pharm Sci. 89(8):967-78 (2000), Powell et al. "Compendium of excipients for parenteral formulations" PDA J Pharm Sci Technol. 52:238-311 (1998) and the citations therein for additional information related to formulations, excipients and carriers well known to pharmaceutical chemists.

The medicaments of the invention are prepared in a manner known to those skilled in the art, for example, by means of conventional dissolving, lyophilizing, mixing, granulating or confectioning processes. Methods well known in the art for making formulations are found, for example, in Remington: The Science and Practice of Pharmacy, 20th ed., ed. A. R. Gennaro, 2000, Lippincott Williams & Wilkins, Philadelphia, and Encyclopedia of Pharmaceutical Technology, eds. J. Swarbrick and J. C. Boylan, 1988-1999, Marcel Dekker, New York.

Administration of medicaments of the invention may be by any suitable means that results in a compound concentration that is effective for treating or inhibiting (e.g., by delaying) the development of a disease. The compound is admixed with a suitable carrier substance, e.g., a pharmaceutically acceptable excipient that preserves the therapeutic properties of the compound with which it is administered. One exemplary pharmaceutically acceptable excipient is physiological saline. The suitable carrier substance is generally present in an amount of 1-95% by weight of the total weight of the medicament. The medicament may be provided in a dosage form that is suitable for administration. Thus, the medicament may be in form of, e.g., tablets, capsules, pills, powders, granulates, suspensions, emulsions, solutions, gels including hydrogels, pastes, ointments, creams, plasters, drenches, delivery devices, injectables, implants, sprays, or aerosols.

The agents disclosed herein (e.g., antibodies) may be used in a pharmaceutical composition when combined with a pharmaceutically acceptable carrier. Such compositions comprise a therapeutically-effective amount of the agent and a pharmaceutically acceptable carrier. Such a composition may also further comprise (in addition to an agent and a carrier) diluents, fillers, salts, buffers, stabilizers, solubilizers, and other materials well known in the art. Compositions comprising the agent can be administered in the form of salts provided the salts are pharmaceutically acceptable. Salts may be prepared using standard procedures known to those skilled in the art of synthetic organic chemistry.

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. The term "pharmaceutically acceptable salt" further includes all acceptable salts such as acetate, lactobionate, benzenesulfonate, laurate, benzoate, malate, bicarbonate, maleate, bi sulfate, mandelate, bitartrate, mesylate, borate, methylbromide, bromide, methylnitrate, calcium edetate, methyl sulfate, camsylate, mucate, carbonate, napsylate, chloride, nitrate, clavulanate, N-methylglucamine, citrate, ammonium salt, dihydrochloride, oleate, edetate, oxalate, edisylate, pamoate (embonate), estolate, palmitate, esylate, pantothenate, fumarate, phosphate/diphosphate, gluceptate, polygalacturonate, gluconate, salicylate, glutamate, stearate, glycollylarsanilate, sulfate, hexylresorcinate, subacetate, hydrabamine, succinate, hydrobromide, tannate, hydrochloride, tartrate, hydroxynaphthoate, teoclate, iodide, tosylate, isothionate, triethiodide, lactate, panoate, valerate, and the like which can be used as a dosage form for modifying the solubility or hydrolysis characteristics or can be used in sustained release or prodrug formulations. It will be understood that, as used herein, references to specific agents (e.g., neuromedin U receptor agonists or antagonists), also include the pharmaceutically acceptable salts thereof.

Methods of administrating the pharmacological compositions, including agonists, antagonists, antibodies or fragments thereof, to an individual include, but are not limited to, intradermal, intrathecal, intramuscular, intraperitoneal, intravenous, subcutaneous, intranasal, epidural, by inhalation, and oral routes. The compositions can be administered by any convenient route, for example by infusion or bolus injection, by absorption through epithelial or mucocutaneous linings (for example, oral mucosa, rectal and intestinal mucosa, and the like), ocular, and the like and can be administered together with other biologically-active agents. Administration can be systemic or local. In addition, it may be advantageous to administer the composition into the central nervous system by any suitable route, including intraventricular and intrathecal injection. Pulmonary administration may also be employed by use of an inhaler or nebulizer, and formulation with an aerosolizing agent. It may also be desirable to administer the agent locally to the area in need of treatment; this may be achieved by, for example, and not by way of limitation, local infusion during surgery, topical application, by injection, by means of a catheter, by means of a suppository, or by means of an implant.

Various delivery systems are known and can be used to administer the pharmacological compositions including, but not limited to, encapsulation in liposomes, microparticles, microcapsules; minicells; polymers; capsules; tablets; and the like. In one embodiment, the agent may be delivered in a vesicle, in particular a liposome. In a liposome, the agent is combined, in addition to other pharmaceutically acceptable carriers, with amphipathic agents such as lipids which exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. Nos. 4,837,028 and 4,737,323. In yet another embodiment, the pharmacological compositions can be delivered in a controlled release system including, but not limited to: a delivery pump (See, for example, Saudek, et al., New Engl. J. Med. 321: 574 (1989) and a semi-permeable polymeric material (See, for example, Howard, et al., J. Neurosurg. 71: 105 (1989)). Additionally, the controlled release system can be placed in proximity of the therapeutic target (e.g., a tumor or infected tissue), thus requiring only a fraction of the systemic dose. See, for example, Goodson, In: Medical Applications of Controlled Release, 1984. (CRC Press, Boca Raton, Fla.).

The amount of the agents which will be effective in the treatment of a particular disorder or condition will depend on the nature of the disorder or condition, and may be determined by standard clinical techniques by those of skill within the art. In addition, in vitro assays may optionally be employed to help identify optimal dosage ranges. The precise dose to be employed in the formulation will also depend on the route of administration, and the overall seriousness of the disease or disorder, and should be decided according to the judgment of the practitioner and each patient's circumstances. Ultimately, the attending physician will decide the amount of the agent with which to treat each individual patient. In certain embodiments, the attending physician will administer low doses of the agent and observe the patient's response. Larger doses of the agent may be administered until the optimal therapeutic effect is obtained for the patient, and at that point the dosage is not increased further. In general, the daily dose range of a drug lie within the range known in the art for a particular drug or biologic. Effective doses may be extrapolated from dose-response curves derived from in vitro or animal model test systems. Ultimately the attending physician will decide on the appropriate duration of therapy using compositions of the present invention. Dosage will also vary according to the age, weight and response of the individual patient.

Methods for administering antibodies for therapeutic use is well known to one skilled in the art. In certain embodiments, small particle aerosols of antibodies or fragments thereof may be administered (see e.g., Piazza et al., J. Infect. Dis., Vol. 166, pp. 1422-1424, 1992; and Brown, Aerosol Science and Technology, Vol. 24, pp. 45-56, 1996). In certain embodiments, antibodies are administered in metered-dose propellant driven aerosols. In certain embodiments, antibodies may be administered in liposomes, i.e., immunoliposomes (see, e.g., Maruyama et al., Biochim. Biophys. Acta, Vol. 1234, pp. 74-80, 1995). In certain embodiments, immunoconjugates, immunoliposomes or immunomicrospheres containing an agent of the present invention is administered by inhalation.

In certain embodiments, antibodies may be topically administered to mucosa, such as the oropharynx, nasal cavity, respiratory tract, gastrointestinal tract, eye such as the conjunctival mucosa, vagina, urogenital mucosa, or for dermal application. In certain embodiments, antibodies are administered to the nasal, bronchial or pulmonary mucosa. In order to obtain optimal delivery of the antibodies to the pulmonary cavity in particular, it may be advantageous to add a surfactant such as a phosphoglyceride, e.g. phosphatidylcholine, and/or a hydrophilic or hydrophobic complex of a positively or negatively charged excipient and a charged antibody of the opposite charge.

Other excipients suitable for pharmaceutical compositions intended for delivery of antibodies to the respiratory tract mucosa may be a) carbohydrates, e.g., monosaccharides such as fructose, galactose, glucose. D-mannose, sorbiose, and the like; disaccharides, such as lactose, trehalose, cellobiose, and the like; cyclodextrins, such as 2-hydroxypropyl-β-cyclodextrin; and polysaccharides, such as raffinose, maltodextrins, dextrans, and the like; b) amino acids, such as glycine, arginine, aspartic acid, glutamic acid, cysteine, lysine and the like; c) organic salts prepared from organic acids and bases, such as sodium citrate, sodium ascorbate, magnesium gluconate, sodium gluconate, tromethamine hydrochloride, and the like: d) peptides and proteins, such as aspartame, human serum albumin, gelatin, and the like; e) alditols, such mannitol, xylitol, and the like, and f) polycationic polymers, such as chitosan or a chitosan salt or derivative.

For dermal application, the antibodies of the present invention may suitably be formulated with one or more of the following excipients: solvents, buffering agents, preservatives, humectants, chelating agents, antioxidants, stabilizers, emulsifying agents, suspending agents, gel-forming agents, ointment bases, penetration enhancers, and skin protective agents.

Examples of solvents are e.g. water, alcohols, vegetable or marine oils (e.g. edible oils like almond oil, castor oil, cacao butter, coconut oil, corn oil, cottonseed oil, linseed oil, olive oil, palm oil, peanut oil, poppy seed oil, rapeseed oil, sesame oil, soybean oil, sunflower oil, and tea seed oil), mineral oils, fatty oils, liquid paraffin, polyethylene glycols, propylene glycols, glycerol, liquid polyalkylsiloxanes, and mixtures thereof.

Examples of buffering agents are e.g. citric acid, acetic acid, tartaric acid, lactic acid, hydrogenphosphoric acid, diethyl amine etc. Suitable examples of preservatives for use in compositions are parabenes, such as methyl, ethyl, propyl p-hydroxybenzoate, butylparaben, isobutylparaben, isopropylparaben, potassium sorbate, sorbic acid, benzoic acid, methyl benzoate, phenoxyethanol, bronopol, bronidox, MDM hydantoin, iodopropynyl butylcarbamate, EDTA, benzalconium chloride, and benzylalcohol, or mixtures of preservatives.

Examples of humectants are glycerin, propylene glycol, sorbitol, lactic acid, urea, and mixtures thereof.

Examples of antioxidants are butylated hydroxy anisole (BHA), ascorbic acid and derivatives thereof, tocopherol and derivatives thereof, cysteine, and mixtures thereof.

Examples of emulsifying agents are naturally occurring gums, e.g. gum acacia or gum tragacanth; naturally occurring phosphatides, e.g. soybean lecithin, sorbitan monooleate derivatives: wool fats; wool alcohols; sorbitan esters; monoglycerides; fatty alcohols; fatty acid esters (e.g. triglycerides of fatty acids); and mixtures thereof.

Examples of suspending agents are e.g. celluloses and cellulose derivatives such as, e.g., carboxymethyl cellulose, hydroxyethylcellulose, hydroxypropylcellulose, hydroxypropylmethylcellulose, carrageenan, acacia gum, arabic gum, tragacanth, and mixtures thereof.

Examples of gel bases, viscosity-increasing agents or components which are able to take up exudate from a wound are: liquid paraffin, polyethylene, fatty oils, colloidal silica or aluminum, zinc soaps, glycerol, propylene glycol, tragacanth, carboxyvinyl polymers, magnesium-aluminum silicates, Carbopol®, hydrophilic polymers such as, e.g. starch or cellulose derivatives such as, e.g., carboxymethylcellulose, hydroxyethylcellulose and other cellulose derivatives, water-swellable hydrocolloids, carrageenans, hyaluronates (e.g. hyaluronate gel optionally containing sodium chloride), and alginates including propylene glycol alginate.

Examples of ointment bases are e.g. beeswax, paraffin, cetanol, cetyl palmitate, vegetable oils, sorbitan esters of fatty acids (Span), polyethylene glycols, and condensation products between sorbitan esters of fatty acids and ethylene oxide, e.g. polyoxyethylene sorbitan monooleate (Tween).

Examples of hydrophobic or water-emulsifying ointment bases are paraffins, vegetable oils, animal fats, synthetic glycerides, waxes, lanolin, and liquid polyalkylsiloxanes. Examples of hydrophilic ointment bases are solid macrogols (polyethylene glycols). Other examples of ointment bases are triethanolamine soaps, sulphated fatty alcohol and polysorbates.

Examples of other excipients are polymers such as carmellose, sodium carmellose, hydroxypropylmethylcellulose, hydroxyethylcellulose, hydroxypropylcellulose, pectin, xanthan gum, locust bean gum, acacia gum, gelatin, carbomer, emulsifiers like vitamin E, glyceryl stearates, cetanyl glucoside, collagen, carrageenan, hyaluronates and alginates and chitosans.

The dose of antibody required in humans to be effective in the treatment of TB infection differs with the type and severity of the TB to be treated, the age and condition of the patient, etc. Typical doses of antibody to be administered are in the range of 1 µg to 1 g, preferably 1-1000 more preferably 2-500, even more preferably 5-50, most preferably 10-20 µg per unit dosage form. In certain embodiments, infusion of antibodies of the present invention may range from 10-500 mg/m$^2$.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. The currently preferred in vivo gene transfer techniques include transduction with viral (typically lentivirus, adeno associated virus (AAV) and adenovirus) vectors.

In certain embodiments, an agent that reduces a gene signature as described herein is used to treat a subject in need thereof having a TB infection.

The pharmaceutical composition can be applied parenterally, rectally, orally or topically. Preferably, the pharmaceutical composition may be used for intravenous, intramuscular, subcutaneous, peritoneal, peridural, rectal, nasal, pulmonary, mucosal, or oral application. In a preferred embodiment, the pharmaceutical composition according to the invention is intended to be used as an infuse. The skilled person will understand that compositions which are to be administered orally or topically will usually not comprise cells, although it may be envisioned for oral compositions to also comprise cells, for example when gastro-intestinal tract indications are treated. Each of the cells or active components (e.g., modulants, immunomodulants, antigens) as discussed herein may be administered by the same route or may be administered by a different route. By means of example, and without limitation, cells may be administered parenterally and other active components may be administered orally.

Liquid pharmaceutical compositions may generally include a liquid carrier such as water or a pharmaceutically acceptable aqueous solution. For example, physiological saline solution, tissue or cell culture media, dextrose or other saccharide solution or glycols such as ethylene glycol, propylene glycol or polyethylene glycol may be included. The composition may include one or more cell protective molecules, cell regenerative molecules, growth factors, anti-apoptotic factors or factors that regulate gene expression in the cells. Such substances may render the cells independent of their environment. Such pharmaceutical compositions may contain further components ensuring the viability of the cells therein. For example, the compositions may comprise a suitable buffer system (e.g., phosphate or carbonate buffer system) to achieve desirable pH, more usually near neutral pH, and may comprise sufficient salt to ensure isoosmotic conditions for the cells to prevent osmotic stress. For example, suitable solution for these purposes may be phosphate-buffered saline (PBS), sodium chloride solution, Ringer's Injection or Lactated Ringer's Injection, as known in the art. Further, the composition may comprise a carrier protein, e.g., albumin (e.g., bovine or human albumin), which may increase the viability of the cells.

Further suitably pharmaceutically acceptable carriers or additives are well known to those skilled in the art and for instance may be selected from proteins such as collagen or gelatine, carbohydrates such as starch, polysaccharides, sugars (dextrose, glucose and sucrose), cellulose derivatives like sodium or calcium carboxymethylcellulose, hydroxypropyl cellulose or hydroxypropylmethyl cellulose, pregeletanized starches, pectin agar, carrageenan, clays, hydrophilic gums (acacia gum, guar gum, arabic gum and xanthan gum), alginic acid, alginates, hyaluronic acid, polyglycolic and polylactic acid, dextran, pectins, synthetic polymers such as water-soluble acrylic polymer or polyvinylpyrrolidone, proteoglycans, calcium phosphate and the like.

If desired, cell preparation can be administered on a support, scaffold, matrix or material to provide improved tissue regeneration. For example, the material can be a granular ceramic, or a biopolymer such as gelatine, collagen, or fibrinogen. Porous matrices can be synthesized according to standard techniques (e.g., Mikos et al., Biomaterials 14: 323, 1993; Mikos et al., Polymer 35:1068, 1994; Cook et al., J. Biomed. Mater. Res. 35:513, 1997). Such support, scaffold, matrix or material may be biodegradable or non-biodegradable. Hence, the cells may be transferred to and/or cultured on suitable substrate, such as porous or non-porous substrate, to provide for implants.

For example, cells that have proliferated, or that are being differentiated in culture dishes, can be transferred onto three-dimensional solid supports in order to cause them to multiply and/or continue the differentiation process by incubating the solid support in a liquid nutrient medium of the invention, if necessary. Cells can be transferred onto a three-dimensional solid support, e.g. by impregnating the support with a liquid suspension containing the cells. The impregnated supports obtained in this way can be implanted in a human subject. Such impregnated supports can also be re-cultured by immersing them in a liquid culture medium, prior to being finally implanted. The three-dimensional solid support needs to be biocompatible so as to enable it to be implanted in a human. It may be biodegradable or non-biodegradable.

The cells or cell populations can be administered in a manner that permits them to survive, grow, propagate and/or differentiate towards desired cell types (e.g. differentiation) or cell states. The cells or cell populations may be grafted to or may migrate to and engraft within the intended organ. In certain embodiments, a pharmaceutical cell preparation as taught herein may be administered in a form of liquid composition. In embodiments, the cells or pharmaceutical composition comprising such can be administered systemically, topically, within an organ or at a site of organ dysfunction or lesion.

The term "therapeutically effective amount" refers to an amount which can elicit a biological or medicinal response in a tissue, system, animal or human that is being sought by a researcher, veterinarian, medical doctor or other clinician, and in particular can prevent or alleviate one or more of the local or systemic symptoms or features of a disease or condition being treated.

A further aspect of the invention provides a modulating infection in a population of infected cells as taught herein. The terms "cell population" or "population" denote a set of cells having characteristics in common. The characteristics may include in particular the one or more marker(s) or gene or gene product signature(s) as taught herein. The cells as taught herein may be comprised in a cell population. By means of example, the specified cells may constitute at least 40% (by number) of all cells of the cell population, for example, at least 45%, preferably at least 50%, at least 55%, more preferably at least 60%, at least 65%, still more preferably at least 70%, at least 75%, even more preferably at least 80%, at least 85%, and yet more preferably at least 90%, at least 95%, at least 96%, at least 97%, at least 98%, at least 99%, or even 100% of all cells of the cell population.

The isolated cells, cells, or populations thereof as disclosed throughout this specification may be suitably cultured or cultivated in vitro. The term "in vitro" generally denotes outside, or external to, a body, e.g., an animal or human body. The term encompasses "ex vivo". The terms "culturing" or "cell culture" are common in the art and broadly refer to maintenance of cells and potentially expansion (proliferation, propagation) of cells in vitro. Typically, animal cells, such as mammalian cells, such as human cells, are cultured by exposing them to (i.e., contacting them with) a suitable cell culture medium in a vessel or container adequate for the purpose (e.g., a 96-, 24-, or 6-well plate, a T-25, T-75, T-150 or T-225 flask, or a cell factory), at art-known conditions conducive to in vitro cell culture, such as temperature of 37° C., 5% v/v CO2 and >95% humidity. The term "medium" as used herein broadly encompasses any cell culture medium conducive to maintenance of cells, preferably conducive to proliferation of cells. Typically, the medium will be a liquid culture medium, which facilitates easy manipulation (e.g., decantation, pipetting, centrifugation, filtration, and such) thereof.

Site-Specific Nucleases

In certain embodiments, one or more endogenous genes or gene products may be modified, and therefore, modulated, using a nuclease. The term "nuclease" as used herein broadly refers to an agent, for example a protein or a small molecule, capable of cleaving a phosphodiester bond connecting nucleotide residues in a nucleic acid molecule. In some embodiments, a nuclease may be a protein, e.g., an enzyme that can bind a nucleic acid molecule and cleave a phosphodiester bond connecting nucleotide residues within the nucleic acid molecule. A nuclease may be an endonuclease, cleaving a phosphodiester bonds within a polynucleotide chain, or an exonuclease, cleaving a phosphodiester bond at the end of the polynucleotide chain. Preferably, the nuclease is an endonuclease. Preferably, the nuclease is a site-specific nuclease, binding and/or cleaving a specific phosphodiester bond within a specific nucleotide sequence, which may be referred to as "recognition sequence", "nuclease target site", or "target site". In some embodiments, a nuclease may recognize a single stranded target site, in other embodiments a nuclease may recognize a double-stranded target site, for example a double-stranded DNA target site. Some endonucleases cut a double-stranded nucleic acid target site symmetrically, i.e., cutting both strands at the same position so that the ends comprise base-paired nucleotides, also known as blunt ends. Other endonucleases cut a double-stranded nucleic acid target sites asymmetrically, i.e., cutting each strand at a different position so that the ends comprise unpaired nucleotides. Unpaired nucleotides at the end of a double-stranded DNA molecule are also referred to as "overhangs", e.g., "5'-overhang" or "3'-overhang", depending on whether the unpaired nucleotide(s) form(s) the 5' or the 5' end of the respective DNA strand.

The nuclease may introduce one or more single-strand nicks and/or double-strand breaks in the endogenous gene, whereupon the sequence of the endogenous gene may be modified or mutated via non-homologous end joining (NHEJ) or homology-directed repair (HDR).

In certain embodiments, the nuclease may comprise (i) a DNA-binding portion configured to specifically bind to the endogenous gene and (ii) a DNA cleavage portion. Generally, the DNA cleavage portion will cleave the nucleic acid within or in the vicinity of the sequence to which the DNA-binding portion is configured to bind.

In certain embodiments, the DNA-binding portion may comprise a zinc finger protein or DNA-binding domain thereof, a transcription activator-like effector (TALE) protein or DNA-binding domain thereof, or an RNA-guided protein or DNA-binding domain thereof.

In certain embodiments, the DNA-binding portion may comprise (i) Cas9 or Cpf1 or any Cas protein described herein modified to eliminate its nuclease activity, or (ii) DNA-binding domain of Cas9 or Cpf1 or any Cas protein described herein.

In certain embodiments, the DNA cleavage portion comprises FokI or variant thereof or DNA cleavage domain of FokI or variant thereof.

CRISPR-Cas Systems

In certain embodiments, the nuclease may be an RNA-guided nuclease, such as Cas9 or Cpf1 or any Cas protein described herein.

With respect to general information on CRISPR-Cas Systems, components thereof, and delivery of such components, including methods, materials, delivery vehicles, vectors, particles, AAV, and making and using thereof, including as to amounts and formulations, all useful in the practice of the instant invention, reference is made to: U.S. Pat. Nos. 8,999,641, 8,993,233, 8,945,839, 8,932,814, 8,906,616, 8,895,308, 8,889,418, 8,889,356, 8,871,445, 8,865,406, 8,795,965, 8,771,945 and 8,697,359; US Patent Publications US 2014-0310830 (U.S. application Ser. No. 14/105,031), US 2014-0287938 A1 (U.S. application Ser. No. 14/213,991), US 2014-0273234 A1 (U.S. application Ser. No. 14/293,674), US2014-0273232 A1 (U.S. application Ser. No. 14/290,575), US 2014-0273231 (U.S. application Ser. No. 14/259,420), US 2014-0256046 A1 (U.S. application Ser. No. 14/226,274), US 2014-0248702 A1 (U.S. application Ser. No. 14/258,458), US 2014-0242700 A1 (U.S. application Ser. No. 14/222,930), US 2014-0242699 A1 (U.S. application Ser. No. 14/183,512), US 2014-0242664 A1 (U.S. application Ser. No. 14/104,990), US 2014-0234972 A1 (U.S. application Ser. No. 14/183,471), US 2014-0227787 A1 (U.S. application Ser. No. 14/256,912), US 2014-0189896 A1 (U.S. application Ser. No. 14/105,035), US 2014-0186958 (U.S. application Ser. No. 14/105,017), US 2014-0186919 A1 (U.S. application Ser. No. 14/104,977), US 2014-0186843 A1 (U.S. application Ser. No. 14/104,900), US 2014-0179770 A1 (U.S. application Ser. No. 14/104,837) and US 2014-0179006 A1 (U.S. application Ser. No. 14/183,486), US 2014-0170753 (U.S. application Ser. No. 14/183,429); European Patents EP 2 784 162 B1 and EP 2 771 468 B1; European Patent Applications EP 2 771 468 (EP13818570.7), EP 2 764 103 (EP13824232.6), and EP 2 784 162 (EP14170383.5); and PCT Patent Publications PCT Patent Publications WO 2014/093661 (PCT/US2013/074743), WO 2014/093694 (PCT/US2013/074790), WO 2014/093595 (PCT/US2013/074611), WO 2014/093718 (PCT/US2013/074825), WO 2014/093709 (PCT/US2013/074812), WO 2014/093622 (PCT/US2013/074667), WO 2014/093635 (PCT/US2013/074691), WO 2014/093655 (PCT/US2013/074736), WO 2014/093712 (PCT/US2013/074819), WO2014/093701 (PCT/US2013/074800), WO2014/018423 (PCT/US2013/051418), WO 2014/204723 (PCT/US2014/041790), WO 2014/204724 (PCT/US2014/041800), WO 2014/204725 (PCT/US2014/041803), WO 2014/204726 (PCT/US2014/041804), WO 2014/204727 (PCT/US2014/041806), WO 2014/204728 (PCT/US2014/041808), WO 2014/204729 (PCT/US2014/041809). Reference is also made to U.S. provisional patent applications 61/758,468; 61/802,174; 61/806,375; 61/814,263; 61/819,803 and 61/828,130, filed on Jan. 30, 2013; Mar. 15, 2013; Mar. 28, 2013; Apr. 20, 2013; May 6, 2013 and May 28, 2013 respectively. Reference is also made to U.S. provisional patent application 61/836,123, filed on Jun. 17, 2013. Reference is additionally made to U.S. provisional patent applications 61/835,931, 61/835,936, 61/836,127, 61/836,101, 61/836,080 and 61/835,973, each filed Jun. 17, 2013. Further reference is made to U.S. provisional patent applications 61/862,468 and 61/862,355 filed on Aug. 5, 2013; 61/871,301 filed on Aug. 28, 2013; 61/960,777 filed on Sep. 25, 2013 and 61/961,980 filed on Oct. 28, 2013. Reference is yet further made to: PCT Patent applications Nos: PCT/US2014/041803, PCT/US2014/041800, PCT/US2014/041809, PCT/US2014/041804 and PCT/US2014/041806, each filed Jun. 10, 2014 6/10/14; PCT/US2014/041808 filed Jun. 11, 2014; and PCT/US2014/62558 filed Oct. 28, 2014, and U.S. Provisional Patent Applications Ser. Nos. 61/915,150, 61/915,301, 61/915,267 and 61/915,260, each filed Dec. 12, 2013; 61/757,972 and 61/768,959, filed on Jan. 29, 2013 and Feb. 25, 2013; 61/835,936, 61/836,127, 61/836,101, 61/836,080, 61/835,973, and 61/835,931, filed Jun. 17, 2013; 62/010,888 and 62/010,879, both filed Jun. 11, 2014; 62/010,329 and 62/010,441, each filed Jun. 10, 2014; 61/939,228 and 61/939,242, each filed Feb. 12, 2014; 61/980,012, filed Apr. 15, 2014; 62/038,358, filed Aug. 17, 2014; 62/054,490, 62/055,484, 62/055,460 and 62/055,487, each filed Sep. 25, 2014; and 62/069,243, filed Oct. 27, 2014. Reference is also made to U.S. provisional patent applications Nos. 62/055,484, 62/055,460, and 62/055,487, filed Sep. 25, 2014; U.S. provisional patent application 61/980,012, filed Apr. 15, 2014; and U.S. provisional patent application 61/939,242 filed Feb. 12, 2014. Reference is made to PCT application designating, inter alia, the United States, application No. PCT/US14/41806, filed Jun. 10, 2014. Reference is made to U.S. provisional patent application 61/930,214 filed on Jan. 22, 2014. Reference is made to U.S. provisional patent applications 61/915,251; 61/915,260 and 61/915,267, each filed on Dec. 12, 2013. Reference is made to US provisional patent application U.S. Ser. No. 61/980,012 filed Apr. 15, 2014. Reference is made to PCT application designating, inter alia, the United States, application No. PCT/US14/41806, filed Jun. 10, 2014. Reference is made to U.S. provisional patent application 61/930,214 filed on Jan. 22, 2014. Reference is made to U.S. provisional patent applications 61/915,251; 61/915,260 and 61/915,267, each filed on Dec. 12, 2013.

Mention is also made of U.S. application 62/091,455, filed, 12 Dec. 2014, PROTECTED GUIDE RNAS (PGRNAS); U.S. application 62/096,708, 24 Dec. 2014, PROTECTED GUIDE RNAS (PGRNAS); U.S. application 62/091,462, 12 Dec. 2014, DEAD GUIDES FOR CRISPR TRANSCRIPTION FACTORS; U.S. application 62/096,324, 23 Dec. 2014, DEAD GUIDES FOR CRISPR TRANSCRIPTION FACTORS; U.S. application 62/091,456, 12 Dec. 2014, ESCORTED AND FUNCTIONALIZED GUIDES FOR CRISPR-CAS SYSTEMS; U.S. application 62/091,461, 12 Dec. 2014, DELIVERY, USE AND THERAPEUTIC APPLICATIONS OF THE CRISPR-CAS SYSTEMS AND COMPOSITIONS FOR GENOME EDITING AS TO HEMATOPOETIC STEM CELLS (HSCs); U.S. application 62/094,903, 19 Dec. 2014, UNBIASED IDENTIFICATION OF DOUBLE-STRAND BREAKS AND GENOMIC REARRANGEMENT BY GENOME-WISE INSERT CAPTURE SEQUENCING; U.S. application 62/096,761, 24 Dec. 2014, ENGINEERING OF SYSTEMS, METHODS AND OPTIMIZED ENZYME AND GUIDE SCAFFOLDS FOR SEQUENCE MANIPULATION; U.S. application 62/098,059, 30 Dec. 2014, RNA-TARGETING SYSTEM; U.S. application 62/096,656, 24 Dec. 2014, CRISPR HAVING OR ASSOCIATED WITH DESTABILIZATION DOMAINS; U.S. application 62/096,697, 24 Dec. 2014, CRISPR HAVING OR ASSOCIATED WITH AAV; U.S. application 62/098,158, 30 Dec. 2014, ENGINEERED CRISPR COMPLEX INSERTIONAL TARGETING SYSTEMS; U.S. application 62/151,052, 22 Apr. 2015, CELLULAR TARGETING FOR EXTRACELLULAR EXOSOMAL REPORTING; U.S. application 62/054,490, 24 Sep. 2014, DELIVERY, USE AND THERAPEUTIC APPLICATIONS OF THE CRISPR-CAS SYSTEMS AND COMPOSITIONS FOR TARGETING DISORDERS AND DISEASES USING PARTICLE DELIVERY COMPONENTS; U.S. application 62/055,484, 25 Sep. 2014, SYSTEMS, METHODS AND COMPOSITIONS FOR SEQUENCE MANIPULATION WITH OPTIMIZED FUNCTIONAL CRISPR-CAS SYSTEMS; U.S. application 62/087,537, 4 Dec. 2014, SYSTEMS, METHODS AND COMPOSITIONS FOR SEQUENCE MANIPULATION WITH OPTIMIZED FUNCTIONAL CRISPR-CAS SYSTEMS; U.S. application 62/054,651, 24 Sep. 2014, DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; U.S. application 62/067,886, 23 Oct. 2014, DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; U.S. application 62/054,675, 24 Sep. 2014, DELIVERY, USE AND THERAPEUTIC APPLICATIONS OF THE CRISPR-CAS SYSTEMS AND COMPOSITIONS IN NEURONAL CELLS/TISSUES; U.S. application 62/054,528, 24 Sep. 2014, DELIVERY, USE AND THERAPEUTIC APPLICATIONS OF THE CRISPR-CAS SYSTEMS AND COMPOSITIONS IN IMMUNE DISEASES OR DISORDERS; U.S. application 62/055,454, 25 Sep. 2014, DELIVERY, USE AND THERAPEUTIC APPLICATIONS OF THE CRISPR-CAS SYSTEMS AND COMPOSITIONS FOR TARGETING DISORDERS AND DISEASES USING CELL PENETRATION PEPTIDES (CPP); U.S. application 62/055,460, 25 Sep. 2014, MULTIFUNCTIONAL-CRISPR COMPLEXES AND/OR OPTIMIZED ENZYME LINKED FUNCTIONAL-CRISPR COMPLEXES; U.S. application 62/087,475, 4 Dec. 2014, FUNCTIONAL SCREENING WITH OPTIMIZED FUNCTIONAL CRISPR-CAS SYSTEMS; U.S. application 62/055,487, 25 Sep. 2014, FUNCTIONAL SCREENING WITH OPTIMIZED FUNCTIONAL CRISPR-CAS SYSTEMS; U.S. application 62/087,546, 4 Dec. 2014, MULTIFUNCTIONAL CRISPR COMPLEXES AND/OR OPTIMIZED ENZYME LINKED FUNCTIONAL-CRISPR COMPLEXES; and U.S. application 62/098,285, 30 Dec. 2014, CRISPR MEDIATED IN VIVO MODELING AND GENETIC SCREENING OF TUMOR GROWTH AND METASTASIS.

Each of these patents, patent publications, and applications, and all documents cited therein or during their prosecution ("appln cited documents") and all documents cited or referenced in the appln cited documents, together with any instructions, descriptions, product specifications, and product sheets for any products mentioned therein or in any document therein and incorporated by reference herein, are hereby incorporated herein by reference, and may be employed in the practice of the invention. All documents (e.g., these patents, patent publications and applications and the appln cited documents) are incorporated herein by reference to the same extent as if each individual document was specifically and individually indicated to be incorporated by reference.

Also with respect to general information on CRISPR-Cas Systems, mention is made of the following (also hereby incorporated herein by reference):

Multiplex genome engineering using CRISPR/Cas systems. Cong, L., Ran, F. A., Cox, D., Lin, S., Barretto, R., Habib, N., Hsu, P. D., Wu, X., Jiang, W., Marraffini, L. A., & Zhang, F. Science February 15; 339(6121):819-23 (2013);

RNA-guided editing of bacterial genomes using CRISPR-Cas systems. Jiang W., Bikard D., Cox D., Zhang F, Marraffini L A. Nat Biotechnol March; 31(3):233-9 (2013);

One-Step Generation of Mice Carrying Mutations in Multiple Genes by CRISPR/Cas-Mediated Genome Engineering. Wang H., Yang H., Shivalila C S., Dawlaty M M., Cheng A W., Zhang F., Jaenisch R. Cell May 9; 153(4): 910-8 (2013);

Optical control of mammalian endogenous transcription and epigenetic states. Konermann S, Brigham M D, Trevino A E, Hsu P D, Heidenreich M, Cong L, Platt R J, Scott D A, Church G M, Zhang F. Nature. August 22; 500(7463): 472-6. doi: 10.1038/Nature12466. Epub 2013 Aug. 23 (2013);

Double Nicking by RNA-Guided CRISPR Cas9 for Enhanced Genome Editing Specificity. Ran, F A., Hsu, P D., Lin, C Y., Gootenberg, J S., Konermann, S., Trevino, A E., Scott, D A., Inoue, A., Matoba, S., Zhang, Y., & Zhang, F. Cell August 28. pii: S0092-8674(13)01015-5 (2013-A);

DNA targeting specificity of RNA-guided Cas9 nucleases. Hsu, P., Scott, D., Weinstein, J., Ran, F A., Konermann, S., Agarwala, V., Li, Y., Fine, E., Wu, X., Shalem, O., Cradick, T J., Marraffini, L A., Bao, G., & Zhang, F. Nat Biotechnol doi:10.1038/nbt.2647 (2013);

Genome engineering using the CRISPR-Cas9 system. Ran, F A., Hsu, P D., Wright, J., Agarwala, V., Scott, D A., Zhang, F. Nature Protocols November; 8(11):2281-308 (2013-B);

Genome-Scale CRISPR-Cas9 Knockout Screening in Human Cells. Shalem, O., Sanjana, N E., Hartenian, E., Shi, X., Scott, D A., Mikkelson, T., Heckl, D., Ebert, B L., Root, D E., Doench, J G., Zhang, F. Science December 12. (2013). [Epub ahead of print];

Crystal structure of cas9 in complex with guide RNA and target DNA. Nishimasu, H., Ran, F A., Hsu, P D., Konermann, S., Shehata, S I., Dohmae, N., Ishitani, R., Zhang, F., Nureki, O. Cell February 27, 156(5):935-49 (2014);

Genome-wide binding of the CRISPR endonuclease Cas9 in mammalian cells. Wu X., Scott D A., Kriz A J., Chiu A C., Hsu P D., Dadon D B., Cheng A W., Trevino A E., Konermann S., Chen S., Jaenisch R., Zhang F., Sharp P A. Nat Biotechnol. April 20. doi: 10.1038/nbt.2889 (2014);

CRISPR-Cas9 Knockin Mice for Genome Editing and Cancer Modeling. Platt R J, Chen S, Zhou Y, Yim M J, Swiech L, Kempton H R, Dahlman J E, Parnas O, Eisenhaure T M, Jovanovic M, Graham D B, Jhunjhunwala S, Heidenreich M, Xavier R J, Langer R, Anderson D G, Hacohen N, Regev A, Feng G, Sharp P A, Zhang F. Cell 159(2): 440-455 DOI: 10.1016/j.cell.2014.09.014(2014);

Development and Applications of CRISPR-Cas9 for Genome Engineering, Hsu P D, Lander E S, Zhang F., Cell. June 5; 157(6):1262-78 (2014).

Genetic screens in human cells using the CRISPR/Cas9 system, Wang T, Wei J J, Sabatini D M, Lander E S., Science. January 3; 343(6166): 80-84. doi:10.1126/science.1246981 (2014);

Rational design of highly active sgRNAs for CRISPR-Cas9-mediated gene inactivation, Doench J G, Hartenian E, Graham D B, Tothova Z, Hegde M, Smith I, Sullender M, Ebert B L, Xavier R J, Root D E., (published online 3 Sep. 2014) Nat Biotechnol. December; 32(12):1262-7 (2014);

In vivo interrogation of gene function in the mammalian brain using CRISPR-Cas9, Swiech L, Heidenreich M, Banerjee A, Habib N, Li Y, Trombetta J, Sur M, Zhang F., (published online 19 Oct. 2014) Nat Biotechnol. January; 33(1):102-6 (2015);

Genome-scale transcriptional activation by an engineered CRISPR-Cas9 complex, Konermann S, Brigham M D, Trevino A E, Joung J, Abudayyeh O O, Barcena C, Hsu P D, Habib N, Gootenberg J S, Nishimasu H, Nureki O, Zhang F., Nature. January 29; 517(7536):583-8 (2015).

A split-Cas9 architecture for inducible genome editing and transcription modulation, Zetsche B, Volz S E, Zhang F., (published online 2 Feb. 2015) Nat Biotechnol. February; 33(2):139-42 (2015);

Genome-wide CRISPR Screen in a Mouse Model of Tumor Growth and Metastasis, Chen S, Sanjana N E, Zheng K, Shalem O, Lee K, Shi X, Scott D A, Song J, Pan J Q, Weissleder R, Lee H, Zhang F, Sharp P A. Cell 160, 1246-1260, Mar. 12, 2015 (multiplex screen in mouse), and In vivo genome editing using Staphylococcus aureus Cas9, Ran F A, Cong L, Yan W X, Scott D A, Gootenberg J S, Kriz A J, Zetsche B, Shalem O, Wu X, Makarova K S, Koonin E V, Sharp P A, Zhang F., (published online 1 Apr. 2015), Nature. April 9; 520(7546):186-91 (2015).

Shalem et al., "High-throughput functional genomics using CRISPR-Cas9," Nature Reviews Genetics 16, 299-311 (May 2015).

Xu et al., "Sequence determinants of improved CRISPR sgRNA design," Genome Research 25, 1147-1157 (August 2015).

Parnas et al., "A Genome-wide CRISPR Screen in Primary Immune Cells to Dissect Regulatory Networks," Cell 162, 675-686 (Jul. 30, 2015).

Ramanan et al., CRISPR/Cas9 cleavage of viral DNA efficiently suppresses hepatitis B virus," Scientific Reports 5:10833. doi: 10.1038/srep10833 (Jun. 2, 2015)

Nishimasu et al., Crystal Structure of *Staphylococcus aureus* Cas9," Cell 162, 1113-1126 (Aug. 27, 2015)

Zetsche et al., "Cpf1 Is a Single RNA-Guided Endonuclease of a Class 2 CRISPR-Cas System," Cell 163, 1-13 (Oct. 22, 2015)

Shmakov et al., "Discovery and Functional Characterization of Diverse Class 2 CRISPR-Cas Systems," Molecular Cell 60, 1-13 (Available online Oct. 22, 2015)

each of which is incorporated herein by reference, may be considered in the practice of the instant invention, and discussed briefly below:

Cong et al. engineered type II CRISPR-Cas systems for use in eukaryotic cells based on both *Streptococcus thermophilus* Cas9 and also *Streptococcus pyogenes* Cas9 and demonstrated that Cas9 nucleases can be directed by short RNAs to induce precise cleavage of DNA in human and mouse cells. Their study further showed that Cas9 as converted into a nicking enzyme can be used to facilitate homology-directed repair in eukaryotic cells with minimal mutagenic activity. Additionally, their study demonstrated that multiple guide sequences can be encoded into a single CRISPR array to enable simultaneous editing of several at endogenous genomic loci sites within the mammalian genome, demonstrating easy programmability and wide applicability of the RNA-guided nuclease technology. This ability to use RNA to program sequence specific DNA cleavage in cells defined a new class of genome engineering tools. These studies further showed that other CRISPR loci are likely to be transplantable into mammalian cells and can also mediate mammalian genome cleavage. Importantly, it can be envisaged that several aspects of the CRISPR-Cas system can be further improved to increase its efficiency and versatility.

Jiang et al. used the clustered, regularly interspaced, short palindromic repeats (CRISPR)-associated Cas9 endonuclease complexed with dual-RNAs to introduce precise mutations in the genomes of *Streptococcus pneumoniae* and *Escherichia coli*. The approach relied on dual-RNA:Cas9-directed cleavage at the targeted genomic site to kill unmutated cells and circumvents the need for selectable markers or counter-selection systems. The study reported reprogramming dual-RNA:Cas9 specificity by changing the sequence of short CRISPR RNA (crRNA) to make single- and multinucleotide changes carried on editing templates. The study showed that simultaneous use of two crRNAs enabled multiplex mutagenesis. Furthermore, when the approach was used in combination with recombineering, in *S. pneumoniae*, nearly 100% of cells that were recovered using the described approach contained the desired mutation, and in *E. coli*, 65% that were recovered contained the mutation.

Wang et al. (2013) used the CRISPR/Cas system for the one-step generation of mice carrying mutations in multiple genes which were traditionally generated in multiple steps by sequential recombination in embryonic stem cells and/or time-consuming intercrossing of mice with a single mutation. The CRISPR/Cas system will greatly accelerate the in vivo study of functionally redundant genes and of epistatic gene interactions.

Konermann et al. (2013) addressed the need in the art for versatile and robust technologies that enable optical and chemical modulation of DNA-binding domains based CRISPR Cas9 enzyme and also Transcriptional Activator Like Effectors Ran et al. (2013-A) described an approach that combined a Cas9 nickase mutant with paired guide RNAs to introduce targeted double-strand breaks. This addresses the issue of the Cas9 nuclease from the microbial CRISPR-Cas system being targeted to specific genomic loci by a guide sequence, which can tolerate certain mismatches to the DNA target and thereby promote undesired off-target mutagenesis. Because individual nicks in the genome are repaired with high fidelity, simultaneous nicking via appropriately offset guide RNAs is required for double-stranded breaks and extends the number of specifically recognized bases for target cleavage. The authors demonstrated that using paired nicking can reduce off-target activity by 50- to 1,500-fold in cell lines and to facilitate gene knockout in mouse zygotes without sacrificing on-target cleavage efficiency. This versatile strategy enables a wide variety of genome editing applications that require high specificity.

Hsu et al. (2013) characterized SpCas9 targeting specificity in human cells to inform the selection of target sites and avoid off-target effects. The study evaluated >700 guide RNA variants and SpCas9-induced indel mutation levels at >100 predicted genomic off-target loci in 293T and 293FT cells. The authors that SpCas9 tolerates mismatches between guide RNA and target DNA at different positions in a sequence-dependent manner, sensitive to the number, position and distribution of mismatches. The authors further showed that SpCas9-mediated cleavage is unaffected by DNA methylation and that the dosage of SpCas9 and sgRNA can be titrated to minimize off-target modification. Additionally, to facilitate mammalian genome engineering applications, the authors reported providing a web-based software tool to guide the selection and validation of target sequences as well as off-target analyses.

Ran et al. (2013-B) described a set of tools for Cas9-mediated genome editing via non-homologous end joining (NHEJ) or homology-directed repair (HDR) in mammalian cells, as well as generation of modified cell lines for downstream functional studies. To minimize off-target cleavage, the authors further described a double-nicking strategy using the Cas9 nickase mutant with paired guide RNAs. The protocol provided by the authors experimentally derived guidelines for the selection of target sites, evaluation of cleavage efficiency and analysis of off-target activity. The studies showed that beginning with target design, gene modifications can be achieved within as little as 1-2 weeks, and modified clonal cell lines can be derived within 2-3 weeks.

Shalem et al. described a new way to interrogate gene function on a genome-wide scale. Their studies showed that delivery of a genome-scale CRISPR-Cas9 knockout (GeCKO) library targeted 18,080 genes with 64,751 unique guide sequences enabled both negative and positive selection screening in human cells. First, the authors showed use of the GeCKO library to identify genes essential for cell viability in cancer and pluripotent stem cells. Next, in a melanoma model, the authors screened for genes whose loss is involved in resistance to vemurafenib, a therapeutic that inhibits mutant protein kinase BRAF. Their studies showed that the highest-ranking candidates included previously validated genes NF1 and MED12 as well as novel hits NF2, CUL3, TADA2B, and TADA1. The authors observed a high level of consistency between independent guide RNAs targeting the same gene and a high rate of hit confirmation, and thus demonstrated the promise of genome-scale screening with Cas9.

Nishimasu et al. reported the crystal structure of *Streptococcus pyogenes* Cas9 in complex with sgRNA and its target DNA at 2.5 A° resolution. The structure revealed a bilobed architecture composed of target recognition and nuclease lobes, accommodating the sgRNA:DNA heteroduplex in a positively charged groove at their interface. Whereas the recognition lobe is essential for binding sgRNA and DNA, the nuclease lobe contains the HNH and RuvC nuclease domains, which are properly positioned for cleavage of the complementary and non-complementary strands of the target DNA, respectively. The nuclease lobe also contains a carboxyl-terminal domain responsible for the interaction with the protospacer adjacent motif (PAM). This high-resolution structure and accompanying functional analyses have revealed the molecular mechanism of RNA-guided DNA targeting by Cas9, thus paving the way for the rational design of new, versatile genome-editing technologies.

Wu et al. mapped genome-wide binding sites of a catalytically inactive Cas9 (dCas9) from *Streptococcus pyogenes* loaded with single guide RNAs (sgRNAs) in mouse embryonic stem cells (mESCs). The authors showed that each of the four sgRNAs tested targets dCas9 to between tens and thousands of genomic sites, frequently characterized by a 5-nucleotide seed region in the sgRNA and an NGG protospacer adjacent motif (PAM). Chromatin inaccessibility decreases dCas9 binding to other sites with matching seed sequences; thus 70% of off-target sites are associated with genes. The authors showed that targeted sequencing of 295 dCas9 binding sites in mESCs transfected with catalytically active Cas9 identified only one site mutated above background levels. The authors proposed a two-state model for Cas9 binding and cleavage, in which a seed match triggers binding but extensive pairing with target DNA is required for cleavage.

Platt et al. established a Cre-dependent Cas9 knockin mouse. The authors demonstrated in vivo as well as ex vivo genome editing using adeno-associated virus (AAV)-, lentivirus-, or particle-mediated delivery of guide RNA in neurons, immune cells, and endothelial cells.

Hsu et al. (2014) is a review article that discusses generally CRISPR-Cas9 history from yogurt to genome editing, including genetic screening of cells.

Wang et al. (2014) relates to a pooled, loss-of-function genetic screening approach suitable for both positive and negative selection that uses a genome-scale lentiviral single guide RNA (sgRNA) library.

Doench et al. created a pool of sgRNAs, tiling across all possible target sites of a panel of six endogenous mouse and three endogenous human genes and quantitatively assessed their ability to produce null alleles of their target gene by antibody staining and flow cytometry. The authors showed that optimization of the PAM improved activity and also provided an on-line tool for designing sgRNAs.

Swiech et al. demonstrate that AAV-mediated SpCas9 genome editing can enable reverse genetic studies of gene function in the brain.

Konermann et al. (2015) discusses the ability to attach multiple effector domains, e.g., transcriptional activator, functional and epigenomic regulators at appropriate positions on the guide such as stem or tetraloop with and without linkers.

Zetsche et al. demonstrates that the Cas9 enzyme can be split into two and hence the assembly of Cas9 for activation can be controlled.

Chen et al. relates to multiplex screening by demonstrating that a genome-wide in vivo CRISPR-Cas9 screen in mice reveals genes regulating lung metastasis.

Ran et al. (2015) relates to SaCas9 and its ability to edit genomes and demonstrates that one cannot extrapolate from biochemical assays.

Shalem et al. (2015) described ways in which catalytically inactive Cas9 (dCas9) fusions are used to synthetically repress (CRISPRi) or activate (CRISPRa) expression, showing. advances using Cas9 for genome-scale screens, including arrayed and pooled screens, knockout approaches that inactivate genomic loci and strategies that modulate transcriptional activity.

Xu et al. (2015) assessed the DNA sequence features that contribute to single guide RNA (sgRNA) efficiency in CRISPR-based screens. The authors explored efficiency of CRISPR/Cas9 knockout and nucleotide preference at the cleavage site. The authors also found that the sequence preference for CRISPRi/a is substantially different from that for CRISPR/Cas9 knockout.

Parnas et al. (2015) introduced genome-wide pooled CRISPR-Cas9 libraries into dendritic cells (DCs) to identify genes that control the induction of tumor necrosis factor (Tnf) by bacterial lipopolysaccharide (LPS). Known regulators of Tlr4 signaling and previously unknown candidates were identified and classified into three functional modules with distinct effects on the canonical responses to LPS.

Ramanan et al (2015) demonstrated cleavage of viral episomal DNA (cccDNA) in infected cells. The HBV genome exists in the nuclei of infected hepatocytes as a 3.2 kb double-stranded episomal DNA species called covalently closed circular DNA (cccDNA), which is a key component in the HBV life cycle whose replication is not inhibited by current therapies. The authors showed that sgRNAs specifically targeting highly conserved regions of HBV robustly suppresses viral replication and depleted cccDNA.

Nishimasu et al. (2015) reported the crystal structures of SaCas9 in complex with a single guide RNA (sgRNA) and its double-stranded DNA targets, containing the 5'-TTGAAT-3' PAM and the 5'-TTGGGT-3' PAM. A structural comparison of SaCas9 with SpCas9 highlighted both structural conservation and divergence, explaining their distinct PAM specificities and orthologous sgRNA recognition.

Zetsche et al. (2015) reported the characterization of Cpf1, a putative class 2 CRISPR effector. It was demonstrated that Cpf1 mediates robust DNA interference with features distinct from Cas9. Identifying this mechanism of interference broadens our understanding of CRISPR-Cas systems and advances their genome editing applications.

Shmakov et al. (2015) reported the characterization of three distinct Class 2 CRISPR-Cas systems. The effectors of two of the identified systems, C2c1 and C2c3, contain RuvC like endonuclease domains distantly related to Cpf1. The third system, C2c2, contains an effector with two predicted HEPN RNase domains.

Also, "Dimeric CRISPR RNA-guided FokI nucleases for highly specific genome editing", Shengdar Q. Tsai, Nicolas Wyvekens, Cyd Khayter, Jennifer A. Foden, Vishal Thapar, Deepak Reyon, Mathew J. Goodwin, Martin J. Aryee, J. Keith Joung Nature Biotechnology 32(6): 569-77 (2014), relates to dimeric RNA-guided FokI Nucleases that recognize extended sequences and can edit endogenous genes with high efficiencies in human cells.

In general, the CRISPR-Cas or CRISPR system is as used in the foregoing documents, such as WO 2014/093622 (PCT/US2013/074667) and refers collectively to transcripts and other elements involved in the expression of or directing the activity of CRISPR-associated ("Cas") genes, including sequences encoding a Cas gene, a tracr (trans-activating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or "RNA(s)" as that term is herein used (e.g., RNA(s) to guide Cas, such as Cas9, e.g. CRISPR RNA and transactivating (tracr) RNA or a single guide RNA (sgRNA) (chimeric RNA)) or other sequences and transcripts from a CRISPR locus. In general, a CRISPR system is characterized by elements that promote the formation of a CRISPR complex at the site of a target sequence (also referred to as a protospacer in the context of an endogenous CRISPR system). In the context of formation of a CRISPR complex, "target sequence" refers to a sequence to which a guide sequence is designed to have complementarity, where hybridization between a target sequence and a guide sequence promotes the formation of a CRISPR complex. A target sequence may comprise any polynucleotide, such as DNA or RNA polynucleotides. In some embodiments, a target sequence is located in the nucleus or cytoplasm of a cell. In some embodiments, direct repeats may be identified in silico by searching for repetitive motifs that fulfill any or all of the following criteria: 1. found in a 2 Kb window of genomic sequence flanking the type II CRISPR locus; 2. span from 20 to 50 bp; and 3. interspaced by 20 to 50 bp. In some embodiments, 2 of these criteria may be used, for instance 1 and 2, 2 and 3, or 1 and 3. In some embodiments, all 3 criteria may be used.

In embodiments of the invention the terms guide sequence and guide RNA, i.e. RNA capable of guiding Cas to a target genomic locus, are used interchangeably as in foregoing cited documents such as WO 2014/093622 (PCT/US2013/074667). In general, a guide sequence is any polynucleotide sequence having sufficient complementarity with a target polynucleotide sequence to hybridize with the target sequence and direct sequence-specific binding of a CRISPR complex to the target sequence. In some embodiments, the degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g. the Burrows Wheeler Aligner), ClustalW, Clustal X, BLAT, Novoalign (Novocraft Technologies; available at www.novocraft.com), ELAND (Illumina, San Diego, Calif.), SOAP (available at soap.genomics.org.cn), and Maq (available at maq.sourceforge.net). In some embodiments, a guide sequence is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20, 15, 12, or fewer nucleotides in length. Preferably the guide sequence is 10 30 nucleotides long. The ability of a guide sequence to direct sequence-specific binding of a CRISPR complex to a target sequence may be assessed by any suitable assay. For example, the components of a CRISPR system sufficient to form a CRISPR complex, including the guide sequence to be tested, may be provided to a host cell having the corresponding target sequence, such as by transfection with vectors encoding the components of the CRISPR sequence, followed by an assessment of preferential cleavage within the target sequence, such as by Surveyor assay as described herein. Similarly, cleavage of a target polynucleotide sequence may be evaluated in a test tube by providing the target sequence, components of a CRISPR complex, including the guide sequence to be tested and a control guide sequence different from the test guide sequence, and comparing binding or rate of cleavage at the target sequence between the test and control guide sequence reactions. Other assays are possible, and will occur to those skilled in the art.

In a classic CRISPR-Cas system, the degree of complementarity between a guide sequence and its corresponding target sequence can be about or more than about 50%, 60%, 75%, 80%, 85%, 90%, 95%, 97.5%, 99%, or 100%; a guide or RNA or sgRNA can be about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length; or guide or RNA or sgRNA can be less than about 75, 50, 45, 40, 35, 30, 25, 20, 15, 12, or fewer nucleotides in length; and advantageously tracr RNA is 30 or 50 nucleotides in length. However, an aspect of the invention is to reduce off-target interactions, e.g., reduce the guide interacting with a target sequence having low complementarity. Indeed, in the examples, it is shown that the invention involves mutations that result in the CRISPR-Cas system being able to distinguish between target and off-target sequences that have greater than 80% to about 95% complementarity, e.g., 83%-84% or 88-89% or 94-95% complementarity (for instance, distinguishing between a target having 18 nucleotides from an off-target of 18 nucleotides having 1, 2 or 3 mismatches). Accordingly, in the context of the present invention the degree of complementarity between a guide sequence and its corresponding target sequence is greater than 94.5% or 95% or 95.5% or 96% or 96.5% or 97% or 97.5% or 98% or 98.5% or 99% or 99.5% or 99.9%, or 100%. Off target is less than 100% or 99.9% or 99.5% or 99% or 99% or 98.5% or 98% or 97.5% or 97% or 96.5% or 96% or 95.5% or 95% or 94.5% or 94% or 93% or 92% or 91% or 90% or 89% or 88% or 87% or 86% or 85% or 84% or 83% or 82% or 81% or 80% complementarity between the sequence and the guide, with it advantageous that off target is 100% or 99.9% or 99.5% or 99% or 99% or 98.5% or 98% or 97.5% or 97% or 96.5% or 96% or 95.5% or 95% or 94.5% complementarity between the sequence and the guide.

In particularly preferred embodiments according to the invention, the guide RNA (capable of guiding Cas to a target locus) may comprise (1) a guide sequence capable of hybridizing to a genomic target locus in the eukaryotic cell; (2) a tracr sequence; and (3) a tracr mate sequence. All (1) to (3) may reside in a single RNA, i.e. an sgRNA (arranged in a 5' to 3' orientation), or the tracr RNA may be a different RNA than the RNA containing the guide and tracr sequence. The tracr hybridizes to the tracr mate sequence and directs the CRISPR/Cas complex to the target sequence.

The methods according to the invention as described herein comprehend inducing one or more mutations in a eukaryotic cell (in vitro, i.e. in an isolated eukaryotic cell) as herein discussed comprising delivering to cell a vector as herein discussed. The mutation(s) can include the introduction, deletion, or substitution of one or more nucleotides at each target sequence of cell(s) via the guide(s) RNA(s) or sgRNA(s). The mutations can include the introduction, deletion, or substitution of 1-75 nucleotides at each target sequence of said cell(s) via the guide(s) RNA(s) or sgRNA (s). The mutations can include the introduction, deletion, or substitution of 1, 5, 10, 11, 12, 13, 14, 15, 16, 17, 18, 19, 20, 21, 22, 23, 24, 25, 26, 27, 28, 29, 30, 35, 40, 45, 50, or 75 nucleotides at each target sequence of said cell(s) via the guide(s) RNA(s) or sgRNA(s). The mutations can include the introduction, deletion, or substitution of 5, 10, 11, 12, 13, 14, 15, 16, 17, 18, 19, 20, 21, 22, 23, 24, 25, 26, 27, 28, 29, 30, 35, 40, 45, 50, or 75 nucleotides at each target sequence of said cell(s) via the guide(s) RNA(s) or sgRNA(s). The mutations include the introduction, deletion, or substitution of 10, 11, 12, 13, 14, 15, 16, 17, 18, 19, 20, 21, 22, 23, 24, 25, 26, 27, 28, 29, 30, 35, 40, 45, 50, or 75 nucleotides at each target sequence of said cell(s) via the guide(s) RNA(s) or sgRNA(s). The mutations can include the introduction, deletion, or substitution of 20, 21, 22, 23, 24, 25, 26, 27, 28, 29, 30, 35, 40, 45, 50, or 75 nucleotides at each target sequence of said cell(s) via the guide(s) RNA(s) or sgRNA (s). The mutations can include the introduction, deletion, or substitution of 40, 45, 50, 75, 100, 200, 300, 400 or 500 nucleotides at each target sequence of said cell(s) via the guide(s) RNA(s) or sgRNA(s).

For minimization of toxicity and off-target effect, it will be important to control the concentration of Cas mRNA and guide RNA delivered. Optimal concentrations of Cas mRNA and guide RNA can be determined by testing different concentrations in a cellular or non-human eukaryote animal model and using deep sequencing the analyze the extent of modification at potential off-target genomic loci. Alternatively, to minimize the level of toxicity and off-target effect, Cas nickase mRNA (for example *S. pyogenes* Cas9 with the D10A mutation) can be delivered with a pair of guide RNAs targeting a site of interest. Guide sequences and strategies to minimize toxicity and off-target effects can be as in WO 2014/093622 (PCT/US2013/074667); or, via mutation as herein.

Typically, in the context of an endogenous CRISPR system, formation of a CRISPR complex (comprising a guide sequence hybridized to a target sequence and complexed with one or more Cas proteins) results in cleavage of one or both strands in or near (e.g. within 1, 2, 3, 4, 5, 6, 7, 8, 9, 10, 20, 50, or more base pairs from) the target sequence. Without wishing to be bound by theory, the tracr sequence, which may comprise or consist of all or a portion of a wild-type tracr sequence (e.g. about or more than about 20, 26, 32, 45, 48, 54, 63, 67, 85, or more nucleotides of a wild-type tracr sequence), may also form part of a CRISPR complex, such as by hybridization along at least a portion of the tracr sequence to all or a portion of a tracr mate sequence that is operably linked to the guide sequence.

The nucleic acid molecule encoding a Cas is advantageously codon optimized Cas. An example of a codon optimized sequence, is in this instance a sequence optimized for expression in a eukaryote, e.g., humans (i.e. being optimized for expression in humans), or for another eukaryote, animal or mammal as herein discussed; see, e.g., SaCas9 human codon optimized sequence in WO 2014/093622 (PCT/US2013/074667). Whilst this is preferred, it will be appreciated that other examples are possible and codon optimization for a host species other than human, or for codon optimization for specific organs is known. In some embodiments, an enzyme coding sequence encoding a Cas is codon optimized for expression in particular cells, such as eukaryotic cells. The eukaryotic cells may be those of or derived from a particular organism, such as a mammal, including but not limited to human, or non-human eukaryote or animal or mammal as herein discussed, e.g., mouse, rat, rabbit, dog, livestock, or non-human mammal or primate. In some embodiments, processes for modifying the germ line genetic identity of human beings and/or processes for modifying the genetic identity of animals which are likely to cause them suffering without any substantial medical benefit to man or animal, and also animals resulting from such processes, may be excluded. In general, codon optimization refers to a process of modifying a nucleic acid sequence for enhanced expression in the host cells of interest by replacing at least one codon (e.g. about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database" available at www.kazusa.orjp/codon/and these tables can be adapted in a number of ways. See Nakamura, Y., et al. "Codon usage tabulated from the international DNA sequence databases: status for the year 2000" Nucl. Acids Res. 28:292 (2000). Computer algorithms for codon optimizing a particular sequence for expression in a particular host cell are also available, such as Gene Forge (Aptagen; Jacobus, Pa.), are also available. In some embodiments, one or more codons (e.g. 1, 2, 3, 4, 5, 10, 15, 20, 25, 50, or more, or all codons) in a sequence encoding a Cas correspond to the most frequently used codon for a particular amino acid.

In certain embodiments, the methods as described herein may comprise providing a Cas transgenic cell in which one or more nucleic acids encoding one or more guide RNAs are provided or introduced operably connected in the cell with a regulatory element comprising a promoter of one or more gene of interest. As used herein, the term "Cas transgenic cell" refers to a cell, such as a eukaryotic cell, in which a Cas gene has been genomically integrated. The nature, type, or origin of the cell are not particularly limiting according to the present invention. Also, the way how the Cas transgene is introduced in the cell is may vary and can be any method as is known in the art. In certain embodiments, the Cas transgenic cell is obtained by introducing the Cas transgene in an isolated cell. In certain other embodiments, the Cas transgenic cell is obtained by isolating cells from a Cas transgenic organism. By means of example, and without limitation, the Cas transgenic cell as referred to herein may be derived from a Cas transgenic eukaryote, such as a Cas knock-in eukaryote. Reference is made to WO 2014/093622 (PCT/US13/74667), incorporated herein by reference. Methods of US Patent Publication Nos. 20120017290 and 20110265198 assigned to Sangamo BioSciences, Inc. directed to targeting the Rosa locus may be modified to utilize the CRISPR Cas system of the present invention. Methods of US Patent Publication No. 20130236946 assigned to Cellectis directed to targeting the Rosa locus may also be modified to utilize the CRISPR Cas system of the present invention. By means of further example reference is made to Platt et. al. (Cell; 159(2):440-455 (2014)), describing a Cas9 knock-in mouse, which is incorporated herein by reference. The Cas transgene can further comprise a Lox-Stop-polyA-Lox(LSL) cassette thereby rendering Cas expression inducible by Cre recombinase. Alternatively, the Cas transgenic cell may be obtained by introducing the Cas transgene in an isolated cell. Delivery systems for transgenes are well known in the art. By means of example, the Cas transgene may be delivered in for instance eukaryotic cell by means of vector (e.g., AAV, adenovirus, lentivirus) and/or particle and/or nanoparticle delivery, as also described herein elsewhere.

It will be understood by the skilled person that the cell, such as the Cas transgenic cell, as referred to herein may comprise further genomic alterations besides having an integrated Cas gene or the mutations arising from the sequence specific action of Cas when complexed with RNA capable of guiding Cas to a target locus, such as for instance one or more oncogenic mutations, as for instance and without limitation described in Platt et al. (2014), Chen et al., (2014) or Kumar et al. (2009).

In some embodiments, the Cas sequence is fused to one or more nuclear localization sequences (NLSs), such as about or more than about 1, 2, 3, 4, 5, 6, 7, 8, 9, 10, or more NLSs. In some embodiments, the Cas comprises about or more than about 1, 2, 3, 4, 5, 6, 7, 8, 9, 10, or more NLSs at or near the amino-terminus, about or more than about 1, 2, 3, 4, 5, 6, 7, 8, 9, 10, or more NLSs at or near the carboxy-terminus, or a combination of these (e.g. zero or at least one or more NLS at the amino-terminus and zero or at one or more NLS at the carboxy terminus). When more than one NLS is present, each may be selected independently of the others, such that a single NLS may be present in more than one copy and/or in combination with one or more other NLSs present in one or more copies. In a preferred embodiment of the invention, the Cas comprises at most 6 NLSs. In some embodiments, an NLS is considered near the N- or C-terminus when the nearest amino acid of the NLS is within about 1, 2, 3, 4, 5, 10, 15, 20, 25, 30, 40, 50, or more amino acids along the polypeptide chain from the N- or C-terminus. Non-limiting examples of NLSs include an NLS sequence derived from: the NLS of the SV40 virus large T-antigen, having the amino acid sequence PKKKRKV (SEQ ID NO: 1); the NLS from nucleoplasmin (e.g. the nucleoplasmin bipartite NLS with the sequence KRPAATKKAGQAKKKK) (SEQ ID NO: 2); the c-myc NLS having the amino acid sequence PAAKRVKLD (SEQ ID NO: 3) or RQRRNELKRSP (SEQ ID NO: 4); the hRNPA1 M9 NLS having the sequence NQSSNFGPMKGGNFGGRSSGPYGGGGQYFAK-PRNQGGY (SEQ ID NO: 5); the sequence RMRIZFKNKGKDTAELRRRRVEVSVELRKAKKD-EQILKRRNV (SEQ ID NO: 6) of the IBB domain from importin-alpha; the sequences VSRKRPRP (SEQ ID NO: 7) and PPKKARED (SEQ ID NO: 8) of the myoma T protein; the sequence PQPKKKPL (SEQ ID NO: 9) of human p53; the sequence SALIKKKKKMAP (SEQ ID NO: 10) of mouse c-abl IV; the sequences DRLRR (SEQ ID NO: 11) and PKQKKRK (SEQ ID NO: 12) of the influenza virus NS1; the sequence RKLKKKIKKL (SEQ ID NO: 13) of the Hepatitis virus delta antigen; the sequence REKKKFLKRR (SEQ ID NO: 14) of the mouse Mx1 protein; the sequence KRKGDEVDGVDEVAKKKSKK (SEQ ID NO: 15) of the human poly(ADP-ribose) polymerase; and the sequence RKCLQAGMNLEARKTKK (SEQ ID NO: 16) of the steroid hormone receptors (human) glucocorticoid. In general, the one or more NLSs are of sufficient strength to drive accumulation of the Cas in a detectable amount in the nucleus of a eukaryotic cell. In general, strength of nuclear localization activity may derive from the number of NLSs in the Cas, the particular NLS(s) used, or a combination of these factors. Detection of accumulation in the nucleus may be performed by any suitable technique. For example, a detectable marker may be fused to the Cas, such that location within a cell may be visualized, such as in combination with a means for detecting the location of the nucleus (e.g. a stain specific for the nucleus such as DAPI). Cell nuclei may also be isolated from cells, the contents of which may then be analyzed by any suitable process for detecting protein, such as immunohistochemistry, Western blot, or enzyme activity assay. Accumulation in the nucleus may also be determined indirectly, such as by an assay for the effect of CRISPR complex formation (e.g. assay for DNA cleavage or mutation at the target sequence, or assay for altered gene expression activity affected by CRISPR complex formation and/or Cas enzyme activity), as compared to a control no exposed to the Cas or complex, or exposed to a Cas lacking the one or more NLSs.

Zinc Finger and TALE

One type of programmable DNA-binding domain is provided by artificial zinc-finger (ZF) technology, which involves arrays of ZF modules to target new DNA-binding sites in the genome. Each finger module in a ZF array targets three DNA bases. A customized array of individual zinc finger domains is assembled into a ZF protein (ZFP).

ZFPs can comprise a functional domain. The first synthetic zinc finger nucleases (ZFNs) were developed by fusing a ZF protein to the catalytic domain of the Type IIS restriction enzyme FokI. (Kim, Y. G. et al., 1994, Chimeric restriction endonuclease, Proc. Natl. Acad. Sci. U.S.A. 91, 883-887; Kim, Y. G. et al., 1996, Hybrid restriction enzymes: zinc finger fusions to Fok I cleavage domain. Proc. Natl. Acad. Sci. U.S.A. 93, 1156-1160). Increased cleavage specificity can be attained with decreased off target activity by use of paired ZFN heterodimers, each targeting different nucleotide sequences separated by a short spacer. (Doyon, Y. et al., 2011, Enhancing zinc-finger-nuclease activity with improved obligate heterodimeric architectures. Nat. Methods 8, 74-79). ZFPs can also be designed as transcription activators and repressors and have been used to target many genes in a wide variety of organisms.

In advantageous embodiments of the invention, the methods provided herein use isolated, non-naturally occurring, recombinant or engineered DNA binding proteins that comprise TALE monomers or TALE monomers or half monomers as a part of their organizational structure that enable the targeting of nucleic acid sequences with improved efficiency and expanded specificity.

Naturally occurring TALEs or "wild type TALEs" are nucleic acid binding proteins secreted by numerous species of proteobacteria. TALE polypeptides contain a nucleic acid binding domain composed of tandem repeats of highly conserved monomer polypeptides that are predominantly 33, 34 or 35 amino acids in length and that differ from each other mainly in amino acid positions 12 and 13. In advantageous embodiments the nucleic acid is DNA. As used herein, the term "polypeptide monomers", "TALE monomers" or "monomers" will be used to refer to the highly conserved repetitive polypeptide sequences within the TALE nucleic acid binding domain and the term "repeat variable di-residues" or "RVD" will be used to refer to the highly variable amino acids at positions 12 and 13 of the polypeptide monomers. As provided throughout the disclosure, the amino acid residues of the RVD are depicted using the IUPAC single letter code for amino acids. A general representation of a TALE monomer which is comprised within the DNA binding domain is $X_{1-11}$-$(X_{12}X_{13})$-$X_{14-33 \text{ or } 34 \text{ or } 35}$, where the subscript indicates the amino acid position and X represents any amino acid. $X_{12}X_{13}$ indicate the RVDs. In some polypeptide monomers, the variable amino acid at position 13 is missing or absent and in such monomers, the RVD consists of a single amino acid. In such cases the RVD may be alternatively represented as X*, where X represents $X_{12}$ and (*) indicates that $X_{13}$ is absent. The DNA binding domain comprises several repeats of TALE monomers and this may be represented as $(X_{1-11}$-$(X_{12}X_{13})$-$X_{14-33 \text{ or } 34 \text{ or } 35})_z$, where in an advantageous embodiment, z is at least 5 to 40. In a further advantageous embodiment, z is at least 10 to 26.

The TALE monomers have a nucleotide binding affinity that is determined by the identity of the amino acids in its RVD. For example, polypeptide monomers with an RVD of NI preferentially bind to adenine (A), monomers with an RVD of NG preferentially bind to thymine (T), monomers with an RVD of HD preferentially bind to cytosine (C) and monomers with an RVD of NN preferentially bind to both adenine (A) and guanine (G). In yet another embodiment of the invention, monomers with an RVD of IG preferentially bind to T. Thus, the number and order of the polypeptide monomer repeats in the nucleic acid binding domain of a TALE determines its nucleic acid target specificity. In still further embodiments of the invention, monomers with an RVD of NS recognize all four base pairs and may bind to A, T, G or C. The structure and function of TALEs is further described in, for example, Moscou et al., Science 326:1501 (2009); Boch et al., Science 326:1509-1512 (2009); and Zhang et al., Nature Biotechnology 29:149-153 (2011), each of which is incorporated by reference in its entirety.

The polypeptides used in methods of the invention are isolated, non-naturally occurring, recombinant or engineered nucleic acid-binding proteins that have nucleic acid or DNA binding regions containing polypeptide monomer repeats that are designed to target specific nucleic acid sequences.

As described herein, polypeptide monomers having an RVD of HN or NH preferentially bind to guanine and thereby allow the generation of TALE polypeptides with high binding specificity for guanine containing target nucleic acid sequences. In a preferred embodiment of the invention, polypeptide monomers having RVDs RN, NN, NK, SN, NH, KN, HN, NQ, HH, RG, KH, RH and SS preferentially bind to guanine. In a much more advantageous embodiment of the invention, polypeptide monomers having RVDs RN, NK, NQ, HH, KH, RH, SS and SN preferentially bind to guanine and thereby allow the generation of TALE polypeptides with high binding specificity for guanine containing target nucleic acid sequences. In an even more advantageous embodiment of the invention, polypeptide monomers having RVDs HH, KH, NH, NK, NQ, RH, RN and SS preferentially bind to guanine and thereby allow the generation of TALE polypeptides with high binding specificity for guanine containing target nucleic acid sequences. In a further advantageous embodiment, the RVDs that have high binding specificity for guanine are RN, NH RH and KH. Furthermore, polypeptide monomers having an RVD of NV preferentially bind to adenine and guanine. In more preferred embodiments of the invention, monomers having RVDs of H*, HA, KA, N*, NA, NC, NS, RA, and S* bind to adenine, guanine, cytosine and thymine with comparable affinity.

Figure 8:
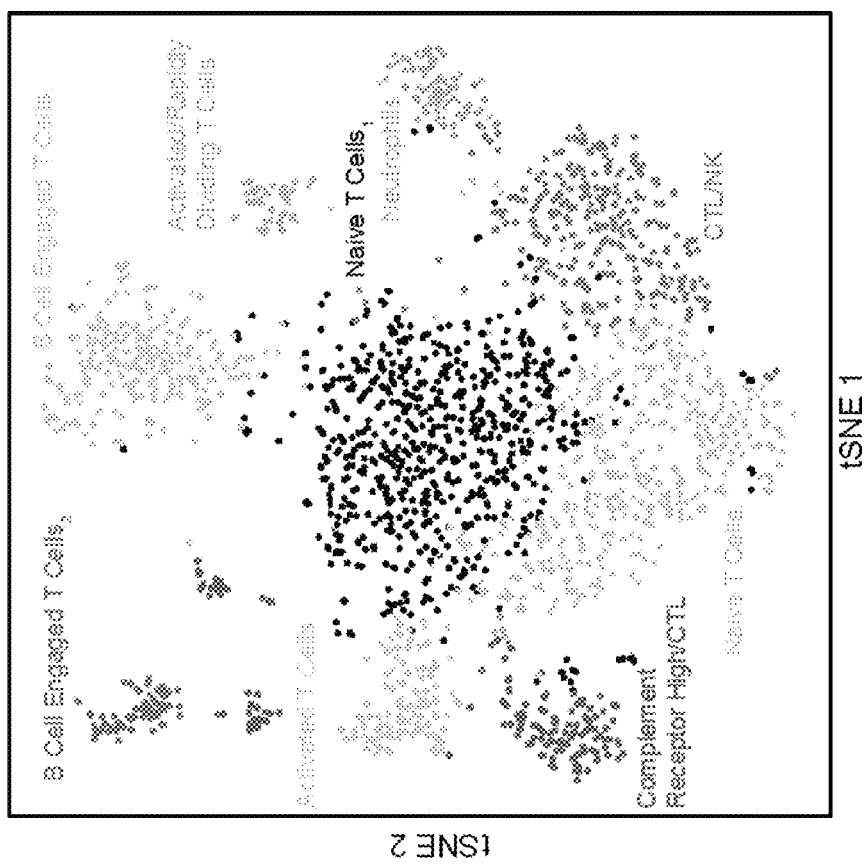
FIG. 8—includes t-distributed stochastic neighbor embedding (t-SNE) plots of CD3E++CD3D++CD3G+ cells by tissue and cell type.
Figure 8:
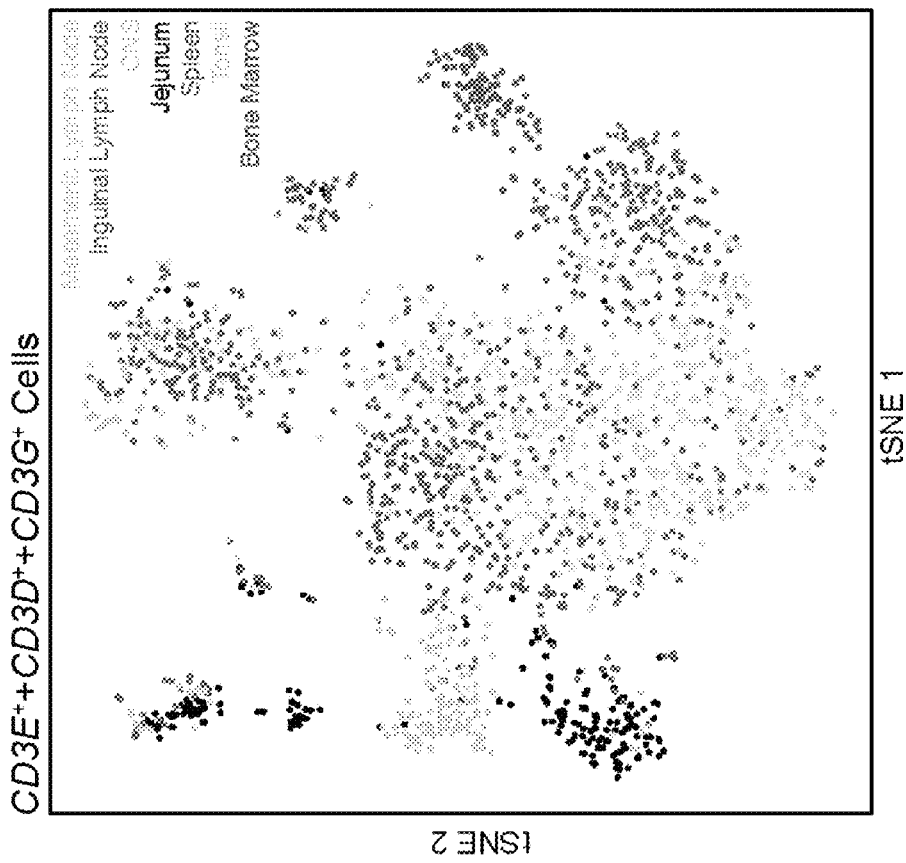
Figure 9A:
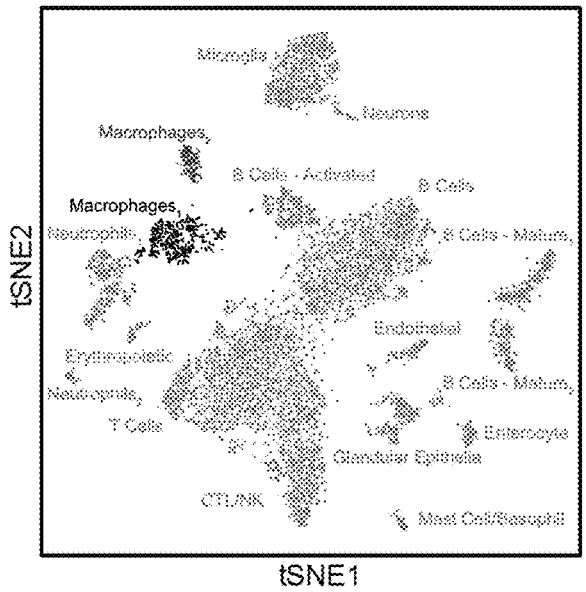
FIG. 9A—plots tissue specific behavior of macrophages t-distributed stochastic neighbor embedding (t-SNE)
Figure 9B:
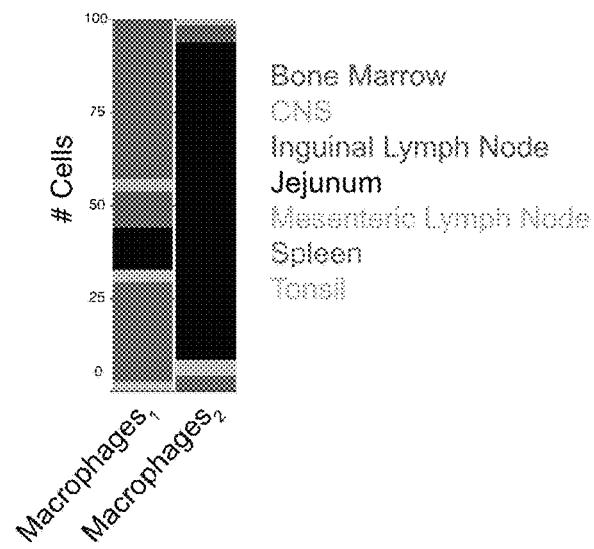
FIG. 9B charts number of tissue specific cells of macrophages.
Figure 9C:
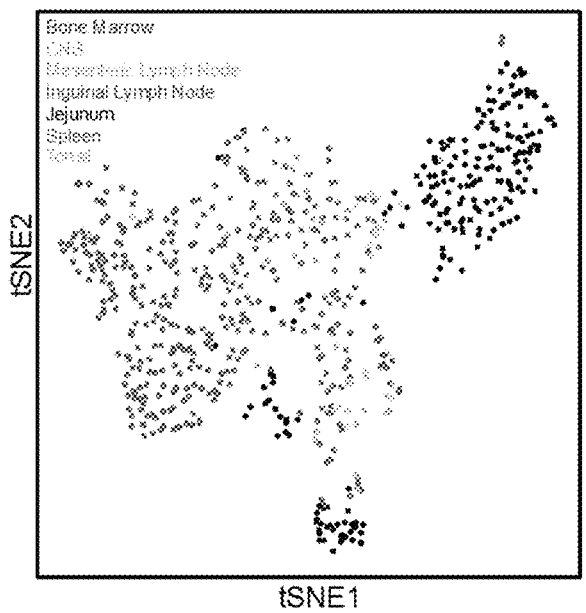
FIG. 9C t-SNE plots of single cell transcriptomes of macrophages identify genes that define them.
Figure 9D:
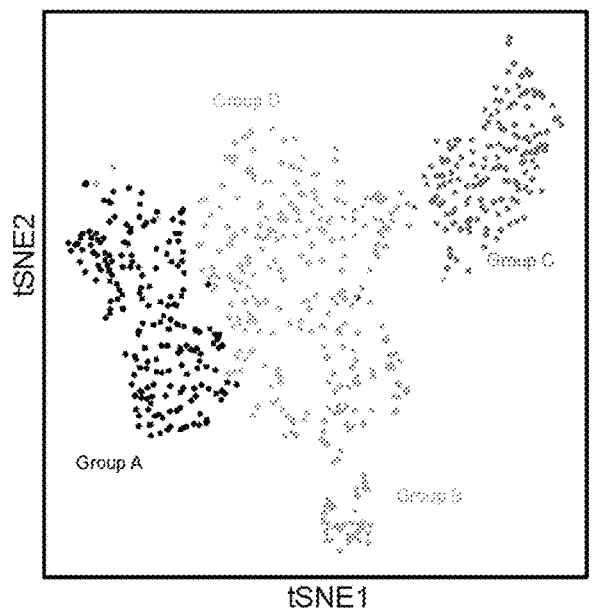
FIG. 9D t-SNE plots of single cell transcriptomes of macrophages identify tissue specific subsets.

The predetermined N-terminal to C-terminal order of the one or more polypeptide monomers of the nucleic acid or DNA binding domain determines the corresponding predetermined target nucleic acid sequence to which the polypeptides of the invention will bind. As used herein the monomers and at least one or more half monomers are "specifically ordered to target" the genomic locus or gene of interest. In plant genomes, the natural TALE-binding sites always begin with a thymine (T), which may be specified by a cryptic signal within the non-repetitive N-terminus of the TALE polypeptide; in some cases, this region may be referred to as repeat 0. In animal genomes, TALE binding sites do not necessarily have to begin with a thymine (T) and polypeptides of the invention may target DNA sequences that begin with T, A, G or C. The tandem repeat of TALE monomers always ends with a half-length repeat or a stretch of sequence that may share identity with only the first 20 amino acids of a repetitive full length TALE monomer and this half repeat may be referred to as a half-monomer (FIG. 8). Therefore, it follows that the length of the nucleic acid or DNA being targeted is equal to the number of full monomers plus two.

As described in Zhang et al., Nature Biotechnology 29:149-153 (2011), TALE polypeptide binding efficiency may be increased by including amino acid sequences from the "capping regions" that are directly N-terminal or C-terminal of the DNA binding region of naturally occurring TALEs into the engineered TALEs at positions N-terminal or C-terminal of the engineered TALE DNA binding region. Thus, in certain embodiments, the TALE polypeptides described herein further comprise an N-terminal capping region and/or a C-terminal capping region.

An exemplary amino acid sequence of a N-terminal capping region is:

```
                                        (SEQ ID NO: 17)
        M D P I R S R T P S P A R E L L S

G P Q P D G V Q P T A D R G V S P

P A G G P L D G L P A R R T M S R

T R L P S P P A P S P A F S A D S

F S D L L R Q F D P S L F N T S L

F D S L P P F G A H H T E A A T G

E W D E V Q S G L R A A D A P P P

T M R V A V T A A R P P R A K P A

P R R R A A Q P S D A S P A A Q V

D L R T L G Y S Q Q Q Q E K I K P

K V R S T V A Q H H E A L V G H G

F T H A H I V A L S Q H P A A L G

T V A V K Y Q D M I A A L P E A T

H E A I V G V G K Q W S G A R A L

E A L L T V A G E L R G P P L Q L

D T G Q L L K I A K R G G V T A V

E A V H A W R N A L T G A P L N
```

An exemplary amino acid sequence of a C-terminal capping region is:

```
                                        (SEQ ID NO: 18)
        R P A L E S I V A Q L S R P D P A L

A A L T N D H L V A L A C L G G R P
```

-continued
```
        A L D A V K K G L P H A P A L I K R

T N R R I P E R T S H R V A D H A Q

V V R V L G F F Q C H S H P A Q A F

D D A M T Q F G M S R H G L L Q L F

R R V G V T E L E A R S G T L P P A

S Q R W D R I L Q A S G M K R A K P

S P T S T Q T P D Q A S L H A F A D

S L E R D L D A P S P M H E G D Q T

R A S
```

As used herein the predetermined "N-terminus" to "C terminus" orientation of the N-terminal capping region, the DNA binding domain comprising the repeat TALE monomers and the C-terminal capping region provide structural basis for the organization of different domains in the d-TALEs or polypeptides of the invention.

The entire N-terminal and/or C-terminal capping regions are not necessary to enhance the binding activity of the DNA binding region. Therefore, in certain embodiments, fragments of the N-terminal and/or C-terminal capping regions are included in the TALE polypeptides described herein.

In certain embodiments, the TALE polypeptides described herein contain a N-terminal capping region fragment that included at least 10, 20, 30, 40, 50, 54, 60, 70, 80, 87, 90, 94, 100, 102, 110, 117, 120, 130, 140, 147, 150, 160, 170, 180, 190, 200, 210, 220, 230, 240, 250, 260 or 270 amino acids of an N-terminal capping region. In certain embodiments, the N-terminal capping region fragment amino acids are of the C-terminus (the DNA-binding region proximal end) of an N-terminal capping region. As described in Zhang et al., Nature Biotechnology 29:149-153 (2011), N-terminal capping region fragments that include the C-terminal 240 amino acids enhance binding activity equal to the full length capping region, while fragments that include the C-terminal 147 amino acids retain greater than 80% of the efficacy of the full length capping region, and fragments that include the C-terminal 117 amino acids retain greater than 50% of the activity of the full-length capping region.

In some embodiments, the TALE polypeptides described herein contain a C-terminal capping region fragment that included at least 6, 10, 20, 30, 37, 40, 50, 60, 68, 70, 80, 90, 100, 110, 120, 127, 130, 140, 150, 155, 160, 170, 180 amino acids of a C-terminal capping region. In certain embodiments, the C-terminal capping region fragment amino acids are of the N-terminus (the DNA-binding region proximal end) of a C-terminal capping region. As described in Zhang et al., Nature Biotechnology 29:149-153 (2011), C-terminal capping region fragments that include the C-terminal 68 amino acids enhance binding activity equal to the full length capping region, while fragments that include the C-terminal 20 amino acids retain greater than 50% of the efficacy of the full length capping region.

In certain embodiments, the capping regions of the TALE polypeptides described herein do not need to have identical sequences to the capping region sequences provided herein. Thus, in some embodiments, the capping region of the TALE polypeptides described herein have sequences that are at least 50%, 60%, 70%, 80%, 85%, 90%, 91%, 92%, 93%, 94%, 95%, 96%, 97%, 98% or 99% identical or share identity to the capping region amino acid sequences provided herein. Sequence identity is related to sequence homology. Homology comparisons may be conducted by eye, or more usually, with the aid of readily available sequence comparison programs. These commercially available computer programs may calculate percent (%) homology between two or more sequences and may also calculate the sequence identity shared by two or more amino acid or nucleic acid sequences. In some preferred embodiments, the capping region of the TALE polypeptides described herein have sequences that are at least 95% identical or share identity to the capping region amino acid sequences provided herein.

Sequence homologies may be generated by any of a number of computer programs known in the art, which include but are not limited to BLAST or FASTA. Suitable computer program for carrying out alignments like the GCG Wisconsin Bestfit package may also be used. Once the software has produced an optimal alignment, it is possible to calculate % homology, preferably % sequence identity. The software typically does this as part of the sequence comparison and generates a numerical result.

In advantageous embodiments described herein, the TALE polypeptides of the invention include a nucleic acid binding domain linked to the one or more effector domains. The terms "effector domain" or "regulatory and functional domain" refer to a polypeptide sequence that has an activity other than binding to the nucleic acid sequence recognized by the nucleic acid binding domain. By combining a nucleic acid binding domain with one or more effector domains, the polypeptides of the invention may be used to target the one or more functions or activities mediated by the effector domain to a particular target DNA sequence to which the nucleic acid binding domain specifically binds.

In some embodiments of the TALE polypeptides described herein, the activity mediated by the effector domain is a biological activity. For example, in some embodiments the effector domain is a transcriptional inhibitor (i.e., a repressor domain), such as an mSin interaction domain (SID). SID4X domain or a Kruppel-associated box (KRAB) or fragments of the KRAB domain. In some embodiments the effector domain is an enhancer of transcription (i.e. an activation domain), such as the VP16, VP64 or p65 activation domain. In some embodiments, the nucleic acid binding is linked, for example, with an effector domain that includes but is not limited to a transposase, integrase, recombinase, resolvase, invertase, protease, DNA methyltransferase, DNA demethylase, histone acetylase, histone deacetylase, nuclease, transcriptional repressor, transcriptional activator, transcription factor recruiting, protein nuclear-localization signal or cellular uptake signal.

In some embodiments, the effector domain is a protein domain which exhibits activities which include but are not limited to transposase activity, integrase activity, recombinase activity, resolvase activity, invertase activity, protease activity, DNA methyltransferase activity, DNA demethylase activity, histone acetylase activity, histone deacetylase activity, nuclease activity, nuclear-localization signaling activity, transcriptional repressor activity, transcriptional activator activity, transcription factor recruiting activity, or cellular uptake signaling activity. Other preferred embodiments of the invention may include any combination the activities described herein.

Target Gene and Gene Products for Modulation

Host gene or product of one or more host genes that may be modulated by agents are provided in Tables 1 and 2. In certain example embodiments, the agent modulates MTB-infected cells by modulating one or more of the genes listed in Table 1. In certain example embodiments, the agent modulates MTB-infected cells by modulating one or more of the genes listed in Table 2. In another example embodiment, the agent modulates MTB-infected cells by modulating one or more of the genes listed in Table 1 (expression induced/increased in MTB+ cells) and/or Table 2 (expression suppressed/decreased in MTB+ cells). A product of one or more host genes includes mRNA of a given gene, or cDNA made of the mRNA, or detectable portions thereof. Any such nucleic acid(s), peptide(s), polypeptide(s) and/or protein(s) encoded by or produced from a given gene are encompassed by a gene product.

Additionally, host genes or products of one or more host genes may be identified by their associated pathways. In some instances, the gene or gene product is part of a gene pathway associated with TB. In particular embodiments, the gene pathway is associated with a high multiplicity of infection (MOI) or a low MOI. In some instances, genes or gene products in the TNFR2 pathway, NOS1 pathway, ETS pathway, NTHI pathway, IL1R pathway, NFkB pathway, MAL pathway, ALK pathway, RAC1 pathway, CCR3 pathway, GCR pathway, PPAR signaling pathway, PPARA activation of gene expression, PPARA pathway, amyotrophic lateral sclerosis pathway, activation of BH3 proteins, SNARE interaction for vesicular transport, Golgi associated vesicle biogenesis, TGF beta signaling pathway, TGF beta receptor signaling activates SMADS, signaling by TGF beta receptor complex, Hematopoietic cell lineage, leishmanial infection, glycosaminoglycan biosynthesis and chondroitin sulfate biosynthesis, metabolism of vitamins and cofactors, fatty Acyl CoA biosynthesis, synthesis, secretion, and inactivation of GLP1, incretin synthesis, secretion, and inactivation, fatty acid triacylglycerol and ketone body metabolism, glycosaminoglycan metabolism, triglyceride biosynthesis, cytokine receptor signaling, lamellipodium assembly, transcriptional repressors, negative regulation of receptor mediated endocytosis, and ubiquitin protein transfer activity, IFNB1, TREX1, CXCL10, IFNA17 in cytosolic DNA sensing pathway, HDAC9, CDKN2C, PPP2R2C, CCND1 in cyclins and cell cycle regulation correlate with high MTB MOI. In some embodiments, genes or gene products of the PARRXR pathway, transcription, RNA Pol I/III Transcription, PI3k Events in ERBB2 signaling, signaling by ERBB2, signaling by EGFR in cancer, chromosome maintenance, telomere maintenance, Acyl chain remodeling, N glycan biosynthesis and protein transfer, respiratory electron transport, chemiosmotic coupling, glycine, serine, and threonine metabolism, TCA cycle, glycolysis and gluconeogenesis, phenylalanine metabolism, purine metabolism, stress and heat shock, transcriptional regulation, linoleic acid metabolism, REGIP, CD69, CD22, SFTPA1, CD72 involved in sugar binding, IFNA1, IFNA13, DHX58, TRADD in RIG-I-like receptor singling pathway, FCER1A, SDC1, CD69, CD276, PCSK9, CD22, TP53I13, GPC1 in cell surface recognition, BAG4 in SODD/TNFR1 signaling pathway, IFNA1 and IFNA13 interferon alpha/beta receptor binding; IL36 G, ARG2, IL1F10, MAP4K4 in 11-10 signaling correlate with low MTB MOI. Accordingly, modulating agents of one or more of these gene pathways can be utilized in accordance with the methods disclosed herein. In an embodiment of the invention, the host gene expression is correlated with the copy number of *M. tuberculosis* in the cell.

In a particular embodiment of the invention, the gene function or gene pathway of the host gene comprises sugar binding, RIG-I-like receptor signaling pathway, cell surface protein, SODD/TNFR1 signaling pathway, interferon-alpha/beta receptor binding, Il-10 signaling, cytosolic DNA-sensing pathway, cytokines, or cyclins and cell cycle regulators. In an embodiment, the host gene comprises REGIP, CD69, CD22, SFTAP1, CD72, IFNA1, IFNA13, DHX58, TRADD, FCER1A, SDC1, CD276, PCSK9, TP53I13, GPC1, BAG4, IL36G, ARG2, IL1F10, MAP4K4, IFNB1, TREX1, CXCL10, IFNA17, HDAC9, CDKN2C, or CCND1. In an embodiment, the host gene is associated with endocytosis or intracellular transport. In an embodiment, the host gene comprises RAB3C, RAC1, APOC1, or NR1H3. In an embodiment of the invention, the host gene is associated with macromolecular complex assembly. In an embodiment of the invention, the host gene comprises TARBP2, TSPYL2, MED27, RAC1, APOC1, H2AFY, NAP1L3, ZW10, or RNF20.

Screening

A further aspect of the invention relates to methods for identifying an agent capable of modulating one or more phenotypic aspects of a pathogen infected cell, comprising: a) applying a candidate agent to the cell or cell population; b) detecting modulation of one or more phenotypic aspects of the cell or cell population by the candidate agent, thereby identifying the agent.

Some embodiments include identifying modulating agents for treating mycobacteria infection. In some instances, a test modulating agent, or candidate compound is administered and a gene expression signature is detected. In some embodiments, subsequent to administration of a test compound, one or more genes of Tables 1 and 2 are measured for differential expression. In some instances, when expression of one or more genes in Table 1 decreases and one ore more genes in Table 2 decreases, the compound be further screened as a candidate modulating agent for mycobacteria infection. As such, particular screening applications of this invention relate to the testing of pharmaceutical compounds in drug research. The reader is referred generally to the standard textbook In vitro Methods in Pharmaceutical Research, Academic Press, 1997, and U.S. Pat. No. 5,030,015. In certain aspects of this invention, the culture of the invention is used to grow and differentiate a cachectic target cell to play the role of test cells for standard drug screening and toxicity assays. Assessment of the activity of candidate pharmaceutical compounds generally involves combining the target cell (e.g., a myocyte, an adipocyte, a cardiomyocyte or a hepatocyte) with the candidate compound, determining any change in the morphology, marker phenotype, or metabolic activity of the cells that is attributable to the candidate compound (compared with untreated cells or cells treated with an inert compound, such as vehicle), and then correlating the effect of the candidate compound with the observed change. The screening may be done because the candidate compound is designed to have a pharmacological effect on the target cell, or because a candidate compound may have unintended side effects on the target cell. Alternatively, libraries can be screened without any predetermined expectations in hopes of identifying compounds with desired effects.

Cytotoxicity can be determined in the first instance by the effect on cell viability and morphology. In certain embodiments, toxicity may be assessed by observation of vital staining techniques, ELISA assays, immunohistochemistry, and the like or by analyzing the cellular content of the culture, e.g., by total cell counts, and differential cell counts or by metabolic markers such as MTT and XTT.

Additional further uses of the culture of the invention include, but are not limited to, its use in research e.g., to elucidate mechanisms leading to the identification of novel targets for therapies, and to generate genotype-specific cells for disease modeling, including the generation of new therapies customized to different genotypes. Such customization can reduce adverse drug effects and help identify therapies appropriate to the patient's genotype.

In certain embodiments, the present invention provides method for high-throughput screening. "High-throughput screening" (HTS) refers to a process that uses a combination of modern robotics, data processing and control software, liquid handling devices, and/or sensitive detectors, to efficiently process a large amount of (e.g., thousands, hundreds of thousands, or millions of) samples in biochemical, genetic or pharmacological experiments, either in parallel or in sequence, within a reasonably short period of time (e.g., days). Preferably, the process is amenable to automation, such as robotic simultaneous handling of 96 samples, 384 samples, 1536 samples or more. A typical HTS robot tests up to 100,000 to a few hundred thousand compounds per day. The samples are often in small volumes, such as no more than 1 mL, 500 µl, 200 µl, 100 µl, 50 µl or less. Through this process, one can rapidly identify active compounds, small molecules, antibodies, proteins or polynucleotides which modulate a particular biomolecular/genetic pathway. The results of these experiments provide starting points for further drug design and for understanding the interaction or role of a particular biochemical process in biology. Thus "high-throughput screening" as used herein does not include handling large quantities of radioactive materials, slow and complicated operator-dependent screening steps, and/or prohibitively expensive reagent costs, etc.

In certain embodiments, the present invention provides for gene signature screening. The concept of signature screening was introduced by Stegmaier et al. (Gene expression-based high-throughput screening (GE-HTS) and application to leukemia differentiation. Nature Genet. 36, 257-263 (2004)), who realized that if a gene-expression signature was the proxy for a phenotype of interest, it could be used to find small molecules that effect that phenotype without knowledge of a validated drug target. The signatures of the present invention may be used to screen for drugs that induce or reduce the signature in cells as described herein. The signature may be used for GE-HTS (Gene Expression-based High-Throughput Screening). In certain embodiments, pharmacological screens may be used to identify drugs that selectively activate or repress infected cells.

The Connectivity Map (cmap) is a collection of genome-wide transcriptional expression data from cultured human cells treated with bioactive small molecules and simple pattern-matching algorithms that together enable the discovery of functional connections between drugs, genes and diseases through the transitory feature of common gene-expression changes (see, Lamb et al., The Connectivity Map: Using Gene-Expression Signatures to Connect Small Molecules, Genes, and Disease. Science 29 Sep. 2006: Vol. 313, Issue 5795, pp. 1929-1935, DOI: 10.1126/science.1132939; and Lamb, J., The Connectivity Map: a new tool for biomedical research. Nature Reviews Cancer January 2007: Vol. 7, pp. 54-60). In certain embodiments, Cmap can be used to screen for small molecules capable of modulating a signature of the present invention in silico.

A blocking antibody or an antibody antagonist is one which inhibits or reduces biological activity of the antigen(s) it binds. In certain embodiments, the blocking antibodies or antagonist antibodies or portions thereof described herein completely inhibit the biological activity of the antigen(s).

Antibodies may act as agonists or antagonists of the recognized polypeptides. For example, the present invention includes antibodies which disrupt receptor/ligand interactions either partially or fully. The invention features both receptor-specific antibodies and ligand-specific antibodies. The invention also features receptor-specific antibodies which do not prevent ligand binding but prevent receptor activation. Receptor activation (i.e., signaling) may be determined by techniques described herein or otherwise known in the art. For example, receptor activation can be determined by detecting the phosphorylation (e.g., tyrosine or serine/threonine) of the receptor or of one of its down-stream substrates by immunoprecipitation followed by western blot analysis. In specific embodiments, antibodies are provided that inhibit ligand activity or receptor activity by at least 95%, at least 90%, at least 85%, at least 80%, at least 75%, at least 70%, at least 60%, or at least 50% of the activity in absence of the antibody.

Diagnostic Methods

Methods as disclosed herein are also directed to methods of diagnosing a cell or tissue in a subject comprising a *Mycobacterium tuberculosis* infection. In methods of diagnosing, the method comprises the step of detecting a gene expression profile in one or more cells or tissues associated with *Mycobacterium tuberculosis* infection. The order of steps provided herein is exemplary, certain steps may be carried out simultaneously or in a different order.

Diagnosis is commonplace and well-understood in medical practice. By means of further explanation and without limitation the term "diagnosis" generally refers to the process or act of recognizing, deciding on or concluding on a disease or condition in a subject on the basis of symptoms and signs and/or from results of various diagnostic procedures (such as, for example, from knowing the presence, absence and/or quantity of one or more biomarkers characteristic of the diagnosed disease or condition). Identifying a disease state, disease progression, or other abnormal condition, based upon symptoms, signs, and other physiological and anatomical parameters are also encompassed in diagnosis. In certain instances, diagnosis comprises detecting a gene expression profile of a sample, host tissue, cell or cell subpopulation.

The terms "prognosing" or "prognosis" generally refer to an anticipation on the progression of a disease or condition and the prospect (e.g., the probability, duration, and/or extent) of recovery. A good prognosis of the diseases or conditions taught herein may generally encompass anticipation of a satisfactory partial or complete recovery from the diseases or conditions, preferably within an acceptable time period. A good prognosis of such may more commonly encompass anticipation of not further worsening or aggravating of such, preferably within a given time period. A poor prognosis of the diseases or conditions as taught herein may generally encompass anticipation of a substandard recovery and/or unsatisfactorily slow recovery, or to substantially no recovery or even further worsening of such.

In certain embodiments, signature genes and biomarkers related to MTB infection and TB symptoms may be identified by comparing single cell expression profiles obtained from uninfected cells and MTB infected cells.

In one particular embodiment, signature genes and biomarkers related MTB infection and TB symptoms may be identified by comparing single cell expression profiles obtained from uninfected cells and cells infected with detectable copies of MTB, such as MTB strain expressing fluorescence markers.

Various aspects and embodiments of the invention may involve analyzing gene signatures, protein signature, and/or other genetic or epigenetic signature based on single cell analyses (e.g. single cell RNA sequencing) or alternatively based on cell population analyses, as is defined herein elsewhere.

A gene profile can be a gene signature, or expression profile. In one aspect, the gene expression profile measures upregulation or down regulation of particular genes or pathways. In particular instances, the gene expression profile comprises one or more genes from Table 1 and/or Table 2.

A gene signature or gene expression profile may encompass any gene or genes, protein or proteins, or epigenetic element(s) whose expression profile or whose occurrence is associated with a specific cell type, subtype, or cell state of a specific cell type or subtype within a population of cells. For ease of discussion, when discussing gene expression, any of gene or genes, protein or proteins, or epigenetic element(s) may be substituted. As used herein, the terms "signature", "expression profile", or "expression program" may be used interchangeably. It is to be understood that also when referring to proteins (e.g. differentially expressed proteins), such may fall within the definition of "gene" signature. Levels of expression or activity or prevalence may be compared between different cells in order to characterize or identify for instance signatures specific for cell (sub) populations. Increased or decreased expression or activity or prevalence of signature genes may be compared between different cells in order to characterize or identify for instance specific cell (sub)populations. The detection of a signature in single cells may be used to identify and quantitate for instance specific cell (sub)populations. A signature may include a gene or genes, protein or proteins, or epigenetic element(s) whose expression or occurrence is specific to a cell (sub)population, such that expression or occurrence is exclusive to the cell (sub)population. A gene signature as used herein, may thus refer to any set of up- and down-regulated genes that are representative of a cell type or subtype. A gene signature as used herein, may also refer to any set of up- and down-regulated genes between different cells or cell (sub)populations derived from a gene-expression profile. For example, a gene signature may comprise a list of genes differentially expressed in a distinction of interest.

The signature as defined herein (being it a gene signature, protein signature or other genetic or epigenetic signature) can be used to indicate the presence of a cell type, a subtype of the cell type, the state of the microenvironment of a population of cells, a particular cell type population or subpopulation, and/or the overall status of the entire cell (sub)population. Furthermore, the signature may be indicative of cells within a population of cells in vivo. The signature may also be used to suggest for instance particular therapies, or to follow up treatment, or to suggest ways to modulate immune systems. The signatures of the present invention may be discovered by analysis of expression profiles of single-cells within a population of cells from isolated samples (e.g. blood samples), thus allowing the discovery of novel cell subtypes or cell states that were previously invisible or unrecognized. The presence of subtypes or cell states may be determined by subtype specific or cell state specific signatures. The presence of these specific cell (sub)types or cell states may be determined by applying the signature genes to bulk sequencing data in a sample. Not being bound by a theory the signatures of the present invention may be microenvironment specific, such as their expression in a particular spatio-temporal context. Not being bound by a theory, signatures as discussed herein are specific to a particular pathological context. Not being bound by a theory, a combination of cell subtypes having a particular signature may indicate an outcome. Not being bound by a theory, the signatures can be used to deconvolute the network of cells present in a particular pathological condition. Not being bound by a theory the presence of specific cells and cell subtypes are indicative of a particular response to treatment, such as including increased or decreased susceptibility to treatment. The signature may indicate the presence of one particular cell type. In one embodiment, the novel signatures are used to detect multiple cell states or hierarchies that occur in subpopulations of infected cells that are linked to particular pathological condition (e.g. presence and/or copy number of TB in cells), or linked to a particular outcome or progression of the disease, or linked to a particular response to treatment of the disease.

The signature according to certain embodiments of the present invention may comprise or consist of one or more genes, proteins and/or epigenetic elements, such as for instance 1, 2, 3, 4, 5, 6, 7, 8, 9, 10 or more. In certain embodiments, the signature may comprise or consist of two or more genes, proteins and/or epigenetic elements, such as for instance 2, 3, 4, 5, 6, 7, 8, 9, 10 or more. In certain embodiments, the signature may comprise or consist of three or more genes, proteins and/or epigenetic elements, such as for instance 3, 4, 5, 6, 7, 8, 9, 10 or more. In certain embodiments, the signature may comprise or consist of four or more genes, proteins and/or epigenetic elements, such as for instance 4, 5, 6, 7, 8, 9, 10 or more. In certain embodiments, the signature may comprise or consist of five or more genes, proteins and/or epigenetic elements, such as for instance 5, 6, 7, 8, 9, 10 or more. In certain embodiments, the signature may comprise or consist of six or more genes, proteins and/or epigenetic elements, such as for instance 6, 7, 8, 9, 10 or more. In certain embodiments, the signature may comprise or consist of seven or more genes, proteins and/or epigenetic elements, such as for instance 7, 8, 9, 10 or more. In certain embodiments, the signature may comprise or consist of eight or more genes, proteins and/or epigenetic elements, such as for instance 8, 9, 10 or more. In certain embodiments, the signature may comprise or consist of nine or more genes, proteins and/or epigenetic elements, such as for instance 9, 10 or more. In certain embodiments, the signature may comprise or consist of ten or more genes, proteins and/or epigenetic elements, such as for instance 10, 11, 12, 13, 14, 15, or more. It is to be understood that a signature according to the invention may for instance also include genes or proteins as well as epigenetic elements combined.

In certain embodiments, a signature is characterized as being specific for a particular cell or cell (sub)population if it is upregulated or only present, detected or detectable in that particular cell or cell (sub)population, or alternatively is downregulated or only absent, or undetectable in that particular cell or cell (sub)population. In this context, a signature consists of one or more differentially expressed genes/proteins or differential epigenetic elements when comparing different cells or cell (sub)populations, including comparing different cells or cell (sub)populations, as well as comparing infected cells or cell (sub)populations with non-infected cells or cell (sub)populations, or cells or cell (sub)populations treated with modulating agents with cells or cell (sub)populations not treated with modulating agents. It is to be understood that "differentially expressed" genes/proteins include genes/proteins which are up- or down-regulated as well as genes/proteins which are turned on or off. When referring to up- or down-regulation, in certain embodiments, such up- or down-regulation is preferably at least two-fold, such as two-fold, three-fold, four-fold, five-fold, or more, such as for instance at least ten-fold, at least 20-fold, at least 30-fold, at least 40-fold, at least 50-fold, or more. Alternatively, or in addition, differential expression may be determined based on common statistical tests, as is known in the art.

As discussed herein, differentially expressed genes/proteins, or differential epigenetic elements may be differentially expressed on a single cell level, or may be differentially expressed on a cell population level. Preferably, the differentially expressed genes/proteins or epigenetic elements as discussed herein, such as constituting the gene signatures as discussed herein, when as to the cell population level, refer to genes that are differentially expressed in all or substantially all cells of the population (such as at least 80%, preferably at least 90%, such as at least 95% of the individual cells). This allows one to define a particular subpopulation of cells. As referred to herein, a "subpopulation" of cells preferably refers to a particular subset of cells of a particular cell type which can be distinguished or are uniquely identifiable and set apart from other cells of this cell type. The cell subpopulation may be phenotypically characterized, and is preferably characterized by the signature as discussed herein. A cell (sub)population as referred to herein may constitute of a (sub)population of cells of a particular cell type characterized by a specific cell state.

When referring to induction, or alternatively suppression of a particular signature, preferable is meant induction or alternatively suppression (or upregulation or downregulation) of at least one gene/protein and/or epigenetic element of the signature, such as for instance at least to, at least three, at least four, at least five, at least six, or all genes/proteins and/or epigenetic elements of the signature.

Signatures may be functionally validated as being uniquely associated with a particular immune responder phenotype. Induction or suppression of a particular signature may consequentially be associated with or causally drive a particular immune responder phenotype.

Various aspects and embodiments of the invention may involve analyzing gene signatures, protein signature, and/or other genetic or epigenetic signature based on single cell analyses (e.g. single cell RNA sequencing) or alternatively based on cell population analyses, as is defined herein elsewhere.

In further aspects, the invention relates to gene signatures, protein signature, and/or other genetic or epigenetic signature of particular infected cell subpopulations, as defined herein elsewhere. The invention hereto also further relates to particular infected cell subpopulations, which may be identified based on the methods according to the invention as discussed herein; as well as methods to obtain such cell (sub)populations and screening methods to identify agents capable of inducing or suppressing particular cell (sub)populations.

The invention further relates to various uses of the gene signatures, protein signature, and/or other genetic or epigenetic signature as defined herein, as well as various uses of the cell, tissues, or cell (sub)populations as defined herein. Particular advantageous uses include methods for identifying agents capable of inducing or suppressing particular cell (sub)populations based on the gene signatures, protein signature, and/or other genetic or epigenetic signature as defined herein. The invention further relates to agents capable of inducing or suppressing particular cell (sub) populations based on the gene signatures, protein signature, and/or other genetic or epigenetic signature as defined herein, as well as their use for modulating, such as inducing or repressing, a particular gene signature, protein signature, and/or other genetic or epigenetic signature. In one embodiment, genes in one population of cells may be activated or suppressed in order to affect the cells of another population. In related aspects, modulating, such as inducing or repressing, a particular a particular gene signature, protein signature, and/or other genetic or epigenetic signature may modify overall composition of infected cells, such as infected cell subpopulation composition or distribution, or functionality.

By means of additional guidance, when a cell is said to be positive for or to express or comprise expression of a given marker, such as a given gene or gene product, a skilled person would conclude the presence or evidence of a distinct signal for the marker when carrying out a measurement capable of detecting or quantifying the marker in or on the cell. Suitably, the presence or evidence of the distinct signal for the marker would be concluded based on a comparison of the measurement result obtained for the cell to a result of the same measurement carried out for a negative control (for example, a cell known to not express the marker) and/or a positive control (for example, a cell known to express the marker). Where the measurement method allows for a quantitative assessment of the marker, a positive cell may generate a signal for the marker that is at least 1.5-fold higher than a signal generated for the marker by a negative control cell or than an average signal generated for the marker by a population of negative control cells, e.g., at least 2-fold, at least 4-fold, at least 10-fold, at least 20-fold, at least 30-fold, at least 40-fold, at least 50-fold higher or even higher. Further, a positive cell may generate a signal for the marker that is 3.0 or more standard deviations, e.g., 3.5 or more, 4.0 or more, 4.5 or more, or 5.0 or more standard deviations, higher than an average signal generated for the marker by a population of negative control cells. The upregulation and/or downregulation of gene or gene product, including the amount, may be included as part of the gene signature or expression profile.

A "deviation" of a first value from a second value may generally encompass any direction (e.g., increase: first value>second value; or decrease: first value<second value) and any extent of alteration.

For example, a deviation may encompass a decrease in a first value by, without limitation, at least about 10% (about 0.9-fold or less), or by at least about 20% (about 0.8-fold or less), or by at least about 30% (about 0.7-fold or less), or by at least about 40% (about 0.6-fold or less), or by at least about 50% (about 0.5-fold or less), or by at least about 60% (about 0.4-fold or less), or by at least about 70% (about 0.3-fold or less), or by at least about 80% (about 0.2-fold or less), or by at least about 90% (about 0.1-fold or less), relative to a second value with which a comparison is being made.

For example, a deviation may encompass an increase of a first value by, without limitation, at least about 10% (about 1.1-fold or more), or by at least about 20% (about 1.2-fold or more), or by at least about 30% (about 1.3-fold or more), or by at least about 40% (about 1.4-fold or more), or by at least about 50% (about 1.5-fold or more), or by at least about 60% (about 1.6-fold or more), or by at least about 70% (about 1.7-fold or more), or by at least about 80% (about 1.8-fold or more), or by at least about 90% (about 1.9-fold or more), or by at least about 100% (about 2-fold or more), or by at least about 150% (about 2.5-fold or more), or by at least about 200% (about 3-fold or more), or by at least about 500% (about 6-fold or more), or by at least about 700% (about 8-fold or more), or like, relative to a second value with which a comparison is being made.

Preferably, a deviation may refer to a statistically significant observed alteration. For example, a deviation may refer to an observed alteration which falls outside of error margins of reference values in a given population (as expressed, for example, by standard deviation or standard error, or by a predetermined multiple thereof, e.g., $\pm 1 \times SD$ or $\pm 2 \times SD$ or $\pm 3 \times SD$, or $\pm 1 \times SE$ or $\pm 2 \times SE$ or $\pm 3 \times SE$). Deviation may also refer to a value falling outside of a reference range defined by values in a given population (for example, outside of a range which comprises $\geq 40\%$, $\geq 50\%$, $\geq 60\%$, $\geq 70\%$, $\geq 75\%$ or $\geq 80\%$ or $\geq 85\%$ or $\geq 90\%$ or $\geq 95\%$ or even $\geq 100\%$ of values in said population).

In a further embodiment, a deviation may be concluded if an observed alteration is beyond a given threshold or cut-off. Such threshold or cut-off may be selected as generally known in the art to provide for a chosen sensitivity and/or specificity of the prediction methods, e.g., sensitivity and/or specificity of at least 50%, or at least 60%, or at least 70%, or at least 80%, or at least 85%, or at least 90%, or at least 95%.

For example, receiver-operating characteristic (ROC) curve analysis can be used to select an optimal cut-off value of the quantity of a given immune cell population, biomarker or gene or gene product signatures, for clinical use of the present diagnostic tests, based on acceptable sensitivity and specificity, or related performance measures which are well-known per se, such as positive predictive value (PPV), negative predictive value (NPV), positive likelihood ratio (LR+), negative likelihood ratio (LR−), Youden index, or similar.

Method Embodiment 2, Step 1 (Detecting)

The methods of diagnosing comprise a step of detecting a gene expression profile in one or more cells or tissue associated with *Mycobacterium tuberculosis* infection. The step of detecting can, in one embodiment, comprise whether one or more genes is overexpressed or underexpressed compared to a cell that is not infected. In some preferred embodiments, the cells are immune cells, in some particular embodiments, the cells are macrophages.

In one embodiment, the signature genes may be detected by immunofluorescence, immunohistochemistry, fluorescence activated cell sorting (FACS), mass cytometry (CyTOF), Drop-seq, RNA-seq, scRNA-seq, InDrop, single cell qPCR, MERFISH (multiplex (in situ) RNA FISH) and/or by in situ hybridization. Other methods including absorbance assays and colorimetric assays are known in the art and may be used herein.

All gene name symbols provided herein refer to the gene as commonly known in the art. The examples described herein refer to the human gene names and it is to be understood that the present invention also encompasses genes from other organisms (e.g., mouse genes). Gene symbols may be those referred to by the HUGO Gene Nomenclature Committee (HGNC) or National Center for Biotechnology Information (NCBI). Any reference to the gene symbol is a reference made to the entire gene or variants of the gene. The signature as described herein may encompass any of the genes described herein. In certain embodiments, the gene signature includes surface expressed and secreted proteins. Not being bound by a theory, surface proteins may be targeted for detection and isolation of cell types, or may be targeted therapeutically to modulate an immune response.

In certain embodiments, the gene signature is detected in a bulk sample, whereby the gene signature is detected by deconvolution of bulk expression data such that gene expression is assigned to infected cells and non-infected cells in the sample. In certain embodiments, detecting the gene signature comprises detecting downregulation of the down signature and/or upregulation of the up signature, and wherein not detecting the gene signature comprises detecting upregulation of the down signature and/or downregulation of the up signature.

The step of detecting can, in one embodiment, comprise whether one or more genes is underexpressed or overexpressed compared to a cell that is not infected. The step of detecting can include detecting whether one or more genes is overexpressed and whether one or more genes is underexpressed in a cell or tissue in a subject comprising a *Mycobacterium tuberculosis* infection as compared to a cell that is not infected.

In an embodiment, the step of detecting can include detection of differential gene expression that is indicative of copy number, aggregation state, or both. In some instances, detection of the presence of upregulation of particular genes is also indicated of low single copy infection, high single copy infection, or aggregate infection.

In one embodiment, the method comprises detecting or quantifying MTB infected cells in a biological sample. A marker, for example, a gene or gene product, for example a peptide, polypeptide, protein, or nucleic acid, or a group of two or more markers, is detected or measured qualitatively or quantitatively in a tested object (e.g., in or on a cell, cell population, tissue, organ, or organism, e.g., in a biological sample of a subject) when the presence or absence and/or quantity of said marker or said group of markers is detected or determined in the tested object, preferably substantially to the exclusion of other molecules and analytes, e.g., other genes or gene products.

In one particular embodiment, signature genes and biomarkers related to MTB infection and TB symptoms may be identified by comparing single cell expression profiles obtained from uninfected cells and cells infected with detectable copies of MTB, such as MTB strain expressing fluorescence markers.

Various aspects and embodiments of the invention may involve analyzing gene signatures, protein signature, and/or other genetic or epigenetic signature based on single cell analyses (e.g. single cell RNA sequencing) or alternatively based on cell population analyses, as is defined herein elsewhere.

In one embodiment, the method comprises detecting or quantifying MTB infected cells in a biological sample. A marker, for example a gene or gene product, for example a peptide, polypeptide, protein, or nucleic acid, or a group of two or more markers, is "detected" or "measured" in a tested object (e.g., in or on a cell, cell population, tissue, organ, or organism, e.g., in a biological sample of a subject) when the presence or absence and/or quantity of said marker or said group of markers is detected or determined in the tested object, preferably substantially to the exclusion of other molecules and analytes, e.g., other genes or gene products.

In one embodiment, the method comprises detecting or quantifying a sub-population of cells harboring persistent or latent infection in a biological sample. A marker, for example a gene or gene product, for example a peptide, polypeptide, protein, or nucleic acid, or a group of two or more markers, is detected or measured in a tested object (e.g., in or on a cell, cell population, tissue, organ, or organism, e.g., in a biological sample of a subject) when the presence or absence and/or quantity of said marker or said group of markers is detected or determined in the tested object, preferably substantially to the exclusion of other molecules and analytes, e.g., other genes or gene products.

In one embodiment, the method comprises detecting or quantifying MTB infected cells in a biological sample. A marker, for example a gene or gene product, for example a peptide, polypeptide, protein, or nucleic acid, or a group of two or more markers, is "detected" or "measured" in a tested object (e.g., in or on a cell, cell population, tissue, organ, or organism, e.g., in a biological sample of a subject) when the presence or absence and/or quantity of said marker or said group of markers is detected or determined in the tested object, preferably substantially to the exclusion of other molecules and analytes, e.g., other genes or gene products.

In one embodiment, the method comprises detecting or quantifying MTB infection state or MTB copy numbers in TB cells in a biological sample. A marker, for example a gene or gene product, for example a peptide, polypeptide, protein, or nucleic acid, or a group of two or more markers, is "detected" or "measured" in a tested object (e.g., in or on a cell, cell population, tissue, organ, or organism, e.g., in a biological sample of a subject) when the presence or absence and/or quantity of said marker or said group of markers is detected or determined in the tested object, preferably substantially to the exclusion of other molecules and analytes, e.g., other genes or gene products.

In some embodiments, overexpression of a gene associated with a pathway is provided, in some instances, the pathway can be selected from sugar binding, RIG-I-like receptor signaling pathway, cell surface protein, SODD/TNFR1 signaling pathway, interferon-alpha/beta receptor binding, IL-10 signaling, cytosolic DNA-sensing pathway, cytokines, or cyclins and cell cycle regulators. In particular instances, the overexpression of a gene in a particular pathway is indicative of low or high multiplicity of infection. In some embodiments, overexpressed gene is indicative of low multiplicity of infection, and is associated with a function or pathway selected from cytosolic DNA-sensing pathway, cytokines, or cyclins and cell cycle regulators. In some embodiments, the overexpressed gene is indicative of high multiplicity of infection, and is associated with a function or pathway selected from comprising sugar binding, RIG-I-like receptor signaling pathway, cell surface protein, SODD/TNFR1 signaling pathway, interferon-alpha/beta receptor binding, and IL-10 signaling. In particular instances, the gene comprises REGIP, CD69, CD22, SFTAP1, CD72, IFNA1, IFNA13, DHX58, TRADD, FCER1A, SDC1, CD276, PCSK9, TP53I13, GPC1, BAG4, IL36G, ARG2, IL1F10, MAP4K4, IFNB1, TREX1, CXCL10, IFNA17, HDAC9, CDKN2C, or CCND1.

In a preferred embodiment, the method comprises detecting or quantifying pathogen in an easily obtainable sample such as blood or body fluid as a proxy or surrogate indicative of infection states of the tested sub population of cells, a different sub population of cells, a different tissue, or the whole organism. Particularly preferred cells are immune cells, more particularly macrophages.

In certain embodiments, the cell types disclosed herein may be detected, quantified or isolated using a technique selected from the group consisting of flow cytometry, mass cytometry, fluorescence activated cell sorting (FACS), fluorescence microscopy, affinity separation, magnetic cell separation, microfluidic separation, RNA-seq (e.g., bulk or single cell), quantitative PCR, MERFISH (multiplex (in situ) RNA FISH) and combinations thereof. The technique may employ one or more agents capable of specifically binding to one or more gene products expressed or not expressed by the cells, preferably on the cell surface of the cells. The one or more agents may be one or more antibodies. Other methods including absorbance assays and colorimetric assays are known in the art and may be used herein.

Depending on factors that can be evaluated and decided on by a skilled person, such as, inter alia, the type of a marker (e.g., peptide, polypeptide, protein, or nucleic acid), the type of the tested object (e.g., a cell, cell population, tissue, organ, or organism, e.g., the type of biological sample of a subject, e.g., whole blood, plasma, serum, tissue biopsy), the expected abundance of the marker in the tested object, the type, robustness, sensitivity and/or specificity of the detection method used to detect the marker, etc., the marker may be measured directly in the tested object, or the tested object may be subjected to one or more processing steps aimed at achieving an adequate measurement of the marker.

In other example embodiments, detection of a marker may include immunological assay methods, wherein the ability of an assay to separate, detect and/or quantify a marker (such as, preferably, peptide, polypeptide, or protein) is conferred by specific binding between a separable, detectable and/or quantifiable immunological binding agent (antibody) and the marker. Immunological assay methods include without limitation immunohistochemistry, immunocytochemistry, flow cytometry, mass cytometry, fluorescence activated cell sorting (FACS), fluorescence microscopy, fluorescence based cell sorting using microfluidic systems, immunoaffinity adsorption based techniques such as affinity chromatography, magnetic particle separation, magnetic activated cell sorting or bead based cell sorting using microfluidic systems, enzyme-linked immunosorbent assay (ELISA) and ELISPOT based techniques, radioimmunoassay (IA), Western blot, etc.

In certain example embodiments, detection of a marker or signature may include biochemical assay methods, including inter alia assays of enzymatic activity, membrane channel activity, substance-binding activity, gene regulatory activity, or cell signaling activity of a marker, e.g., peptide, polypeptide, protein, or nucleic acid.

In other example embodiments, detection of a marker may include mass spectrometry analysis methods. Generally, any mass spectrometric (MS) techniques that are capable of obtaining precise information on the mass of peptides, and preferably also on fragmentation and/or (partial) amino acid sequence of selected peptides (e.g., in tandem mass spectrometry, MS/MS; or in post source decay, TOF MS), may be useful herein for separation, detection and/or quantification of markers (such as, preferably, peptides, polypeptides, or proteins). Suitable peptide MS and MS/MS techniques and systems are well-known per se (see, e.g., Methods in Molecular Biology, vol. 146: "Mass Spectrometry of Proteins and Peptides", by Chapman, ed., Humana Press 2000, ISBN 089603609x; Biemann 1990. Methods Enzymol 193: 455-79; or Methods in Enzymology, vol. 402: "Biological Mass Spectrometry", by Burlingame, ed., Academic Press 2005, ISBN 9780121828073) and may be used herein. MS arrangements, instruments and systems suitable for biomarker peptide analysis may include, without limitation, matrix-assisted laser desorption/ionisation time-of-flight (MALDI-TOF) MS; MALDI-TOF post-source-decay (PSD); MALDI-TOF/TOF; surface-enhanced laser desorption/ionization time-of-flight mass spectrometry (SELDI-TOF) MS; electrospray ionization mass spectrometry (ESI-MS); ESI-MS/MS; ESI-MS/(MS)n (n is an integer greater than zero); ESI 3D or linear (2D) ion trap MS; ESI triple quadrupole MS; ESI quadrupole orthogonal TOF (Q-TOF); ESI Fourier transform MS systems; desorption/ionization on silicon (DIOS); secondary ion mass spectrometry (SIMS); atmospheric pressure chemical ionization mass spectrometry (APCI-MS); APCI-MS/MS; APCI-(MS)n; atmospheric pressure photoionization mass spectrometry (APPI-MS); APPI-MS/MS; and APPI-(MS)n. Peptide ion fragmentation in tandem MS (MS/MS) arrangements may be achieved using manners established in the art, such as, e.g., collision induced dissociation (CID). Detection and quantification of markers by mass spectrometry may involve multiple reaction monitoring (MRM), such as described among others by Kuhn et al. 2004 (Proteomics 4: 1175-86). MS peptide analysis methods may be advantageously combined with upstream peptide or protein separation or fractionation methods, such as for example with the chromatographic and other methods.

In other example embodiments, detection of a marker may include chromatography methods. In a one example embodiment, chromatography refers to a process in which a mixture of substances (analytes) carried by a moving stream of liquid or gas ("mobile phase") is separated into components as a result of differential distribution of the analytes, as they flow around or over a stationary liquid or solid phase ("stationary phase"), between said mobile phase and said stationary phase. The stationary phase may be usually a finely divided solid, a sheet of filter material, or a thin film of a liquid on the surface of a solid, or the like. Chromatography may be columnar. While particulars of chromatography are well known in the art, for further guidance see, e.g., Meyer M., 1998, ISBN: 047198373X, and "Practical HPLC Methodology and Applications", Bidlingmeyer, B. A., John Wiley & Sons Inc., 1993. Exemplary types of chromatography include, without limitation, high-performance liquid chromatography (HPLC), normal phase HPLC (NP-HPLC), reversed phase HPLC (RP-HPLC), ion exchange chromatography (IEC), such as cation or anion exchange chromatography, hydrophilic interaction chromatography (HILIC), hydrophobic interaction chromatography (HIC), size exclusion chromatography (SEC) including gel filtration chromatography or gel permeation chromatography, chromatofocusing, affinity chromatography such as immunoaffinity, immobilised metal affinity chromatography, and the like.

In certain embodiments, further techniques for separating, detecting and/or quantifying markers may be used in conjunction with any of the above described detection methods. Such methods include, without limitation, chemical extraction partitioning, isoelectric focusing (IEF) including capillary isoelectric focusing (CIEF), capillary isotachophoresis (CITP), capillary electrochromatography (CEC), and the like, one-dimensional polyacrylamide gel electrophoresis (PAGE), two-dimensional polyacrylamide gel electrophoresis (2D-PAGE), capillary gel electrophoresis (CGE), capillary zone electrophoresis (CZE), micellar electrokinetic chromatography (MEKC), free flow electrophoresis (FFE), etc.

In certain examples, such methods may include separating, detecting and/or quantifying markers at the nucleic acid level, more particularly RNA level, e.g., at the level of hnRNA, pre-mRNA, mRNA, or cDNA. Standard quantitative RNA or cDNA measurement tools known in the art may be used. Non-limiting examples include hybridization-based analysis, microarray expression analysis, digital gene expression profiling (DGE), RNA-in-situ hybridization (RISH), Northern-blot analysis and the like; PCR, RT-PCR, RT-qPCR, end-point PCR, digital PCR or the like; supported oligonucleotide detection, pyrosequencing, polony cyclic sequencing by synthesis, simultaneous bi-directional sequencing, single-molecule sequencing, single molecule real time sequencing, true single molecule sequencing, hybridization-assisted nanopore sequencing, sequencing by synthesis, single-cell RNA sequencing (sc-RNA seq), or the like. By means of an example, methods to profile the RNA content of large numbers of individual cells have been recently developed. The cell of origin is determined by a cellular barcode. In certain embodiments, special microfluidic devices have been developed to encapsulate each cell in an individual drop, associate the RNA of each cell with a 'cell barcode' unique to that cell/drop, measure the expression level of each RNA with sequencing, and then use the cell barcodes to determine which cell each RNA molecule came from. In these regards, reference is made to Macosko et al., 2015, "Highly Parallel Genome-wide Expression Profiling of Individual Cells Using Nanoliter Droplets" Cell 161, 1202-1214; International patent application number PCT/US2015/049178, published as WO2016/040476 on Mar. 17, 2016; Klein et al., 2015, "Droplet Barcoding for Single-Cell Transcriptomics Applied to Embryonic Stem Cells" Cell 161, 1187-1201; International patent application number PCT/US2016/027734, published as WO2016168584A1 on Oct. 20, 2016; Zheng, et al., 2016, "Haplotyping germline and cancer genomes with high-throughput linked-read sequencing" Nature Biotechnology 34, 303-311; Zheng, et al., 2017, "Massively parallel digital transcriptional profiling of single cells" Nat. Commun. 8, 14049 doi: 10.1038/ncomms14049; International patent publication number WO 2014210353 A2; Zilionis, et al., 2017, "Single-cell barcoding and sequencing using droplet microfluidics" Nat Protoc. January; 12(1):44-73; Cao et al., 2017, "Comprehensive single cell transcriptional profiling of a multicellular organism by combinatorial indexing" bioRxiv preprint first posted online Feb. 2, 2017, doi: dx.doi.org/10.1101/104844; and Rosenberg et al., 2017, "Scaling single cell transcriptomics through split pool barcoding" bioRxiv preprint first posted online Feb. 2, 2017, doi: dx.doi.org/10.1101/105163, all the contents and disclosure of each of which are herein incorporated by reference in their entirety.

In certain embodiments, the invention involves single nucleus RNA sequencing. In this regard, reference is made to Swiech et al., 2014, "In vivo interrogation of gene function in the mammalian brain using CRISPR-Cas9" Nature Biotechnology Vol. 33, pp. 102-106; and Habib et al., 2016, "Div-Seq: Single-nucleus RNA-Seq reveals dynamics of rare adult newborn neurons" Science, Vol. 353, Issue 6302, pp. 925-928, both of which are herein incorporated by reference in their entirety.

Method Embodiment 2, Optional Step 2 (Detecting)

The methods of diagnosing optionally comprise detected whether gene expression profile is overexpressed compared to a cell or tissue that is not infected, or whether the gene expression profile is underexpressed compared to a cell or tissue that is not infected. In some instances, the cell or tissue in the subject and the cell or tissue that is not infected is of the same cell type or tissue type. In some embodiments, the gene expression profile is correlated with the copy number of TB in the cell. In some instances, the gene expression profile can be indicative of higher copy number or lower copy number of TB within a cell. The step of detecting overexpression or underexpression of particular genes can be performed simultaneously with a gene expression profile. Alternatively, presence of particular genes can be detected initially, with further comparison and/or quantitation, including computation of overexpression and underexpression occurring subsequent to initial detection.

In some embodiments, a host gene is associated with chemotaxis, inflammatory response, metabolism, or cell death when infected with aggregates. In some embodiments, the upregulation of genes is indicative of early MTB infection, or in response to aggregates, in some instances, the host genes are CCL4, and/or IL8. In an embodiment genes KCNA2 and/or CXCL2 are significantly upregulated when aggregates are present in a mycobacteria infection. In other embodiments, particular gene expression shows a gradual increase from uninfected cells, to singles low infected, to singles high infected, to aggregate infected cells, allowing for genes that can be indicative of monitoring across a spectrum of infection states.

Method Embodiment 2, Optional Step 3 (Treating)

Upon diagnosis of an infection, optionally including determination of latent or active infection and/or relative copy numbers of mycobacteria in cells or tissue, treatment regimens can be administered.

As used herein, "treatment" or "treating," or "palliating" or "ameliorating" are used interchangeably. These terms refer to an approach for obtaining beneficial or desired results including but not limited to a therapeutic benefit and/or a prophylactic benefit. By therapeutic benefit is meant any therapeutically relevant improvement in or effect on one or more diseases, conditions, or symptoms under treatment. For prophylactic benefit, the compositions may be administered to a subject at risk of developing a particular disease, condition, or symptom, or to a subject reporting one or more of the physiological symptoms of a disease, even though the disease, condition, or symptom may not have yet been manifested. As used herein "treating" includes ameliorating, curing, preventing it from becoming worse, slowing the rate of progression, or preventing the disorder from re-occurring (i.e., to prevent a relapse).

An effective amount or therapeutically effective amount can refer to the amount of an agent that is sufficient to effect beneficial or desired results. The therapeutically effective amount may vary depending upon one or more of: the subject and disease condition being treated, the weight and age of the subject, the severity of the disease condition, the manner of administration and the like, which can readily be determined by one of ordinary skill in the art. The term also applies to a dose that will provide an image for detection by any one of the imaging methods described herein. The specific dose may vary depending on one or more of: the particular agent chosen, the dosing regimen to be followed, whether it is administered in combination with other compounds, timing of administration, the tissue to be imaged, and the physical delivery system in which it is carried.

Considerations for latent TB infection treatment can include the subject to be treated, including whether the subject has a suppressed or lowered immune systems, including HIV-infected persons, organ transplant recipients, young children, and other persons who are immunosuppressed (e.g. taking the equivalent of >15 mg/day of prednisone for 1 month or longer, taking TNF-α antagonists. Other persons to consider for latent infection treatment can include persons with fibrotic changes on chest radiograph consistent with old TB, recent contacts of an individual with TB, residents and employees of high-risk settings (e.g. nursing homes, homeless shelters, health care facilities), mycobacteriology laboratory personnel, persons from high-prevalence countries and injection drug users.

Several regimens for latent infections are recommended, and can depend on other factors, including health and age of the subject (cdc.gov Treatment Options for Latent Tuberculosis Infection, incorporated herein by reference). Treatment regimens can include isoniazid (INH) for a duration of 6 months or 9 months, requiring a minimum number of doses administered. INH can be administered 9 months daily (270 minimum doses) and is a standard treatment regimen, preferred for HIV-infected people taking antiretroviral therapy, and children aged 2-11; or INH can be administered twice weekly over 9 months (76 minimum doses). INH can also be used in certain instances for 6 months, administered daily (180 minimum doses) or twice weekly (52 minimum doses). INH can also be used in combination with Rifapentine for a duration of three months, dosed once weekly for a minimum of 12 doses. Rifampin (RIF) is recommended administered daily for 4 months for at least 120 minimum doses. In some instances, treatment for latent infection can be based on the methods of detection provided herein, including use of the gene expression signatures as detailed in Tables 1 and 2.

Treatment for active infections can, in some embodiments, include additional testing to determine if the TB infection is drug susceptible or drug resistant prior to treatment. When drug susceptible, a combination of drugs including ethambutol, INH, pyrazinamide and RIF can be used for an initial intensive phase of treatment, followed by administration of INH and RIF for a continuation phase usually given for either 4 or 7 months. Drug-resistant TB, multidrug-resistant TB and extensively drug-resistant TB may require combinations of first-line treatments as discussed, as well as fluoroquinolones, bedaquiline fumarate, ofloxacin, cycloserine, and/or including injectable second-line drugs such as amikacin, kanamycin, or capreomycin. In some instances, treatment for active infection can be based on the methods of detection provided herein, including use of the gene expression signatures as detailed in Tables 1 and 2.

In some embodiments, the treatment can include administering one or modulating agents of a host gene or gene products from the genes listed in Tables 1 and 2, or modulation of a gene or pathways as disclosed herein and as detailed in the examples. Treatment can be based in whole or in part on characterizations of copy number per cell or population of cell; the genes, gene products and pathways associated with multiplicity of infection that are detected, the degree of underexpression or overexpression of certain genes or gene products, or the relative number of differentially expressed genes or gene products.

Method Embodiment 3

In some embodiments, methods of monitoring treatment of a *M. tuberculosis* infection in a subject is provided. Methods of monitoring may comprise one or more steps of detecting, in some instance, at time intervals. The time intervals may be prior to infection and subsequent to infection, during an active infection, prior to treatment and subsequent to beginning treatment, or some combination thereof.

Method Embodiment 3, Step 1 (Monitoring)

The term "monitoring" generally refers to the follow-up of a disease or a condition in a subject for any changes which may occur over time. The term also encompass prediction of a disease. The terms "predicting" or "prediction" generally refer to an advance declaration, indication or foretelling of a disease or condition in a subject not (yet) having said disease or condition. For example, a prediction of a disease or condition in a subject may indicate a probability, chance or risk that the subject will develop said disease or condition, for example within a certain time period or by a certain age. Said probability, chance or risk may be indicated inter alia as an absolute value, range or statistics, or may be indicated relative to a suitable control subject or subject population (such as, e.g., relative to a general, normal or healthy subject or subject population). Hence, the probability, chance or risk that a subject will develop a disease or condition may be advantageously indicated as increased or decreased, or as fold-increased or fold-decreased relative to a suitable control subject or subject population. As used herein, the term "prediction" of the conditions or diseases as taught herein in a subject may also particularly mean that the subject has a 'positive' prediction of such, i.e., that the subject is at risk of having such (e.g., the risk is significantly increased vis-à-vis a control subject or subject population). The term "prediction of no" diseases or conditions as taught herein as described herein in a subject may particularly mean that the subject has a 'negative' prediction of such, i.e., that the subject's risk of having such is not significantly increased vis-à-vis a control subject or subject population.

The invention provides a method for monitoring infection in a subject and for determining the severity of a disease or condition by comparing the gene profiles from a healthy subject or reference control with one from a subject suspected of having a disease or condition, or monitoring the progression of the disease.

Method embodiments are also provided for monitoring a subject having no symptoms of disease to determine onset of or diagnose a disease comprising implanting the detector unit on or in the subject and monitoring changes, or velocity of change in the level or presence of one or more biomolecule markers associated with the disease wherein a change, or alterations in velocity of change in the level or presence of the one or more biomolecule markers indicates presence of the disease.

In another aspect, a method is provided for monitoring a subject to predict response to treatment for a disease comprising implanting the detector unit on or in the subject and monitoring changes in the level or presence of one or more biomolecule markers associated with a disease wherein a change, or alterations in velocity of change in the level or presence of the one or more biomolecule markers associated with treatment resistance of the disease indicates the presence or absence of resistance of the subject to a disease treatment.

The step of detecting for the purposes of monitoring can, in one embodiment, comprise whether one or more genes is overexpressed compared to a cell that is not infected. The step of detecting can, in one embodiment, comprise whether one or more genes is underexpressed compared to a cell that is not infected. The step of detecting can also comprise a gene expression profile of one or more genes, as described herein, and may include overexpressed and underexpressed genes in the gene expression profile.

In one embodiment, the change in the level or presence of the one or more biomolecule markers associated with the disease is compared to normal levels in the subject or a population of healthy or normal subjects where the change, or alterations in velocity of change in the level or presence of the one or more biomolecules indicates the presence of the disease.

The invention is further described in the following examples, which do not limit the scope of the invention described in the claims.

EXAMPLES

Example 1. Human-Derived Macrophages Infected with *M. tuberculosis*

Tuberculosis (TB) is an infectious disease caused by bacterium *Mycobacterium tuberculosis* (MTB). Currently, TB remains one of the most significant infectious disease worldwide, causing 1.8 million deaths annually (WHO. Global tuberculosis report 2016). MTB preferably infects macrophages in lungs, replicates within invaded macrophages, and induces cytokines that initiate inflammatory responses, resulting in granuloma in lungs (and potentially other organs). In MTB infected patients, infectious states and symptoms can vary greatly within the same organ or even tissues. In the same infected lobe, granuloma states can range from resolved to cavitary lesion and caseating.

The standard tests to detect active TB include detecting lung lesion with X-ray images and MTB specific antibody detection. Previous studies have identified biomarkers for diagnosis of active TB and to monitor TB therapy efficiency. However, these biomarkers rely on limited numbers of antigen recognition, or suffer from insensitivity under certain conditions (Friedrich S O et al., Lancet Respir Med. 2013 August; 1(6):462-70; Coppola et al., Tuberculosis 2017, 106: 25-32). A sensitive test that allows for diagnosis with easily obtainable specimens and one that responds to MTB load largely remains in need (Goletti et al., Infectious Disease Reports 2016; 8(2): 6568). More importantly, a comprehensive understanding of immune response and pathogenesis in different states of TB infection is still missing. Thus, it remains unclear whether intrinsic factors or extrinsic micro-environment, or both, contribute to the different behavior of infected macrophages at these different states, and how macrophage phenotype is related to the quantity of intracellular MTB (particularly, MTB multiplicity of infection, MOI).

Human monocytes derived macrophages are infected with an *Mycobacterium tuberculosis* expressing RFP for ~72 hours. Single cells are collected and sorted into 96 well plates using a tet-reporter system in the bacteria by flow cytometry. MTB infected cells indexed with fluorescence intensity of intracellular bacteria as well as uninfected bystanders were collected and single cell RNA-Sequencing was performed.

Figure 2A:
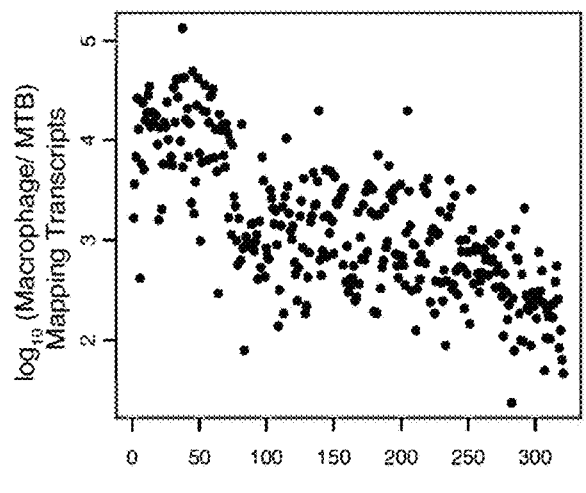
FIG. 2A-2E—MTB-infected macrophages.
Figure 2B:
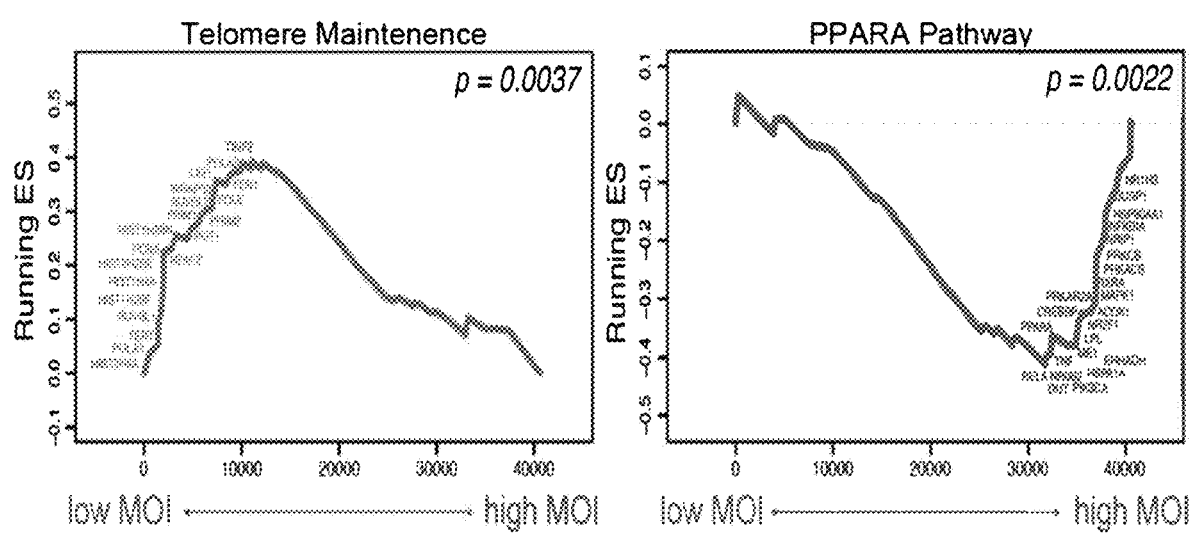
Figure 2C:
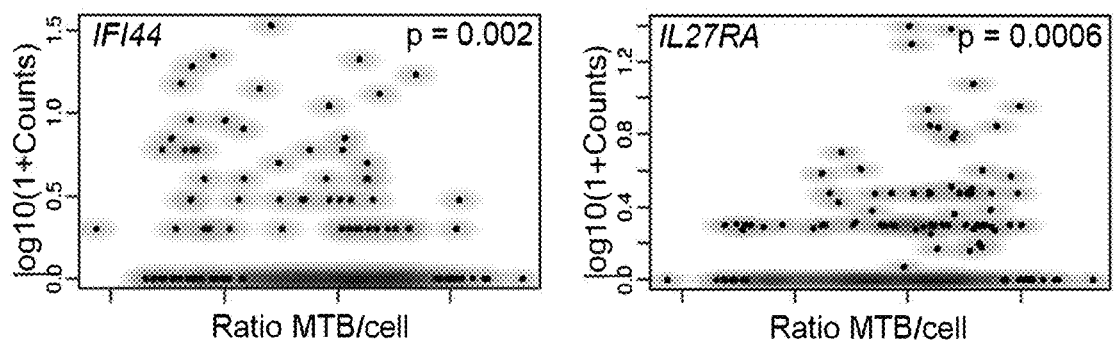
Figure 2D:
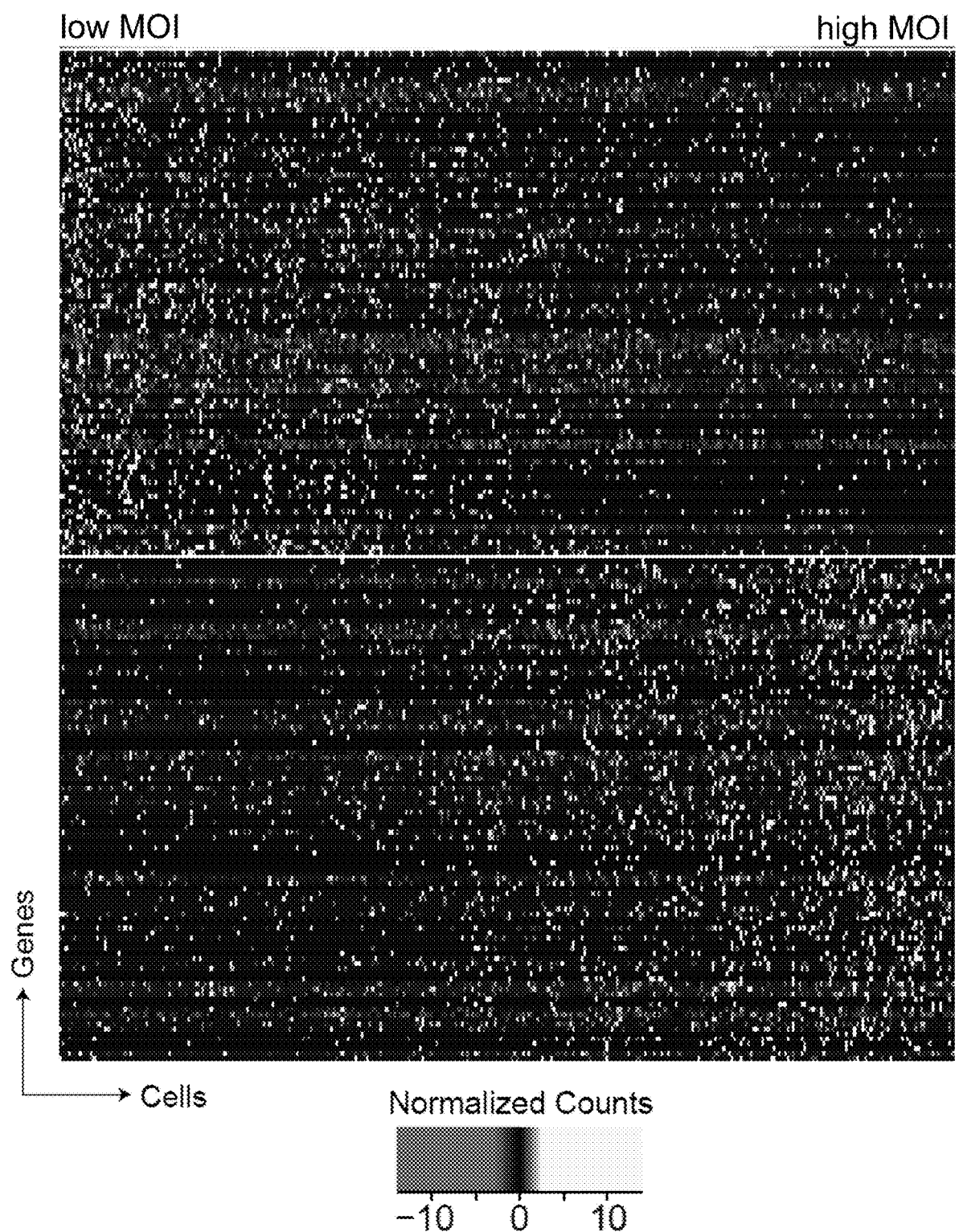
Figure 2E:
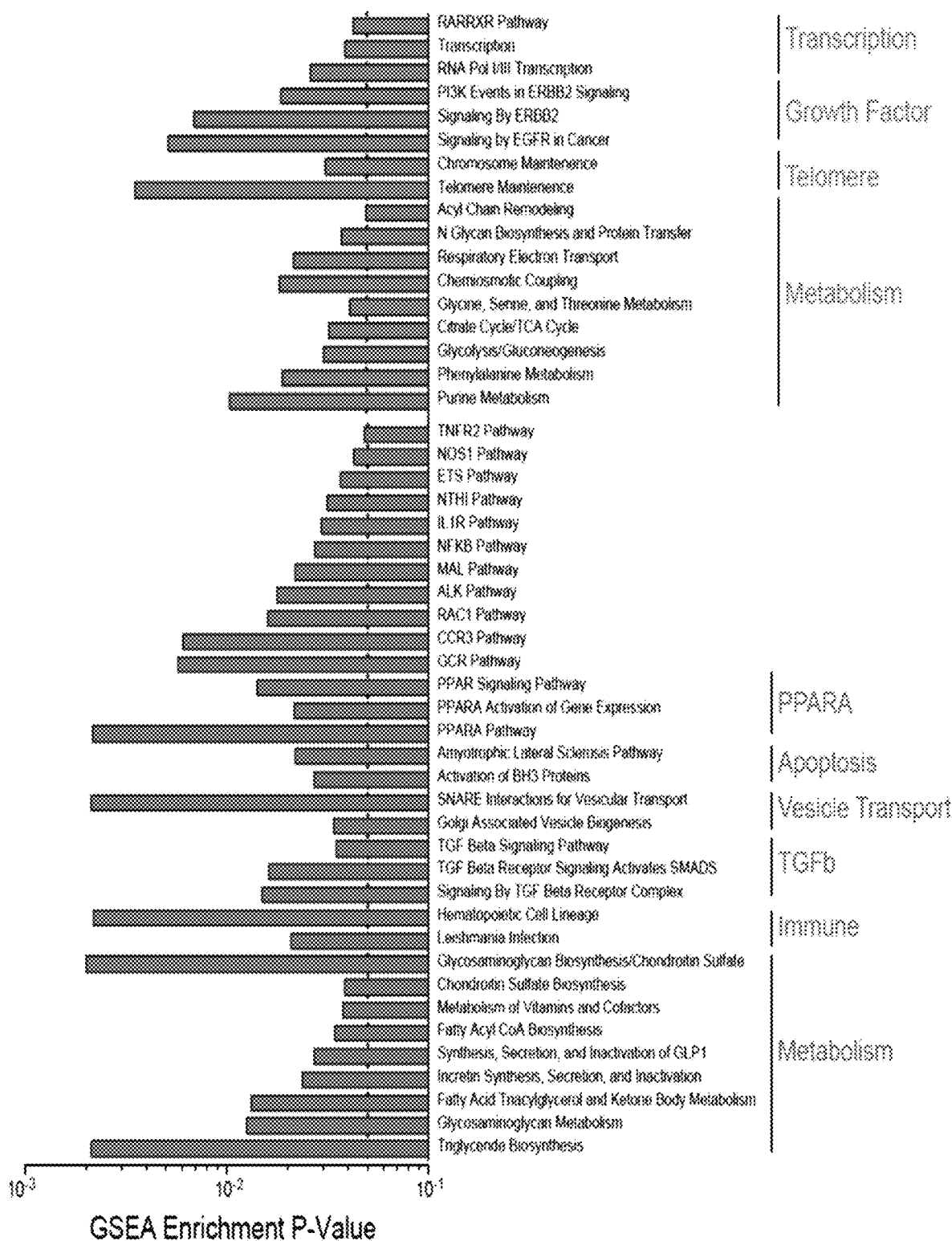
Figure 3:
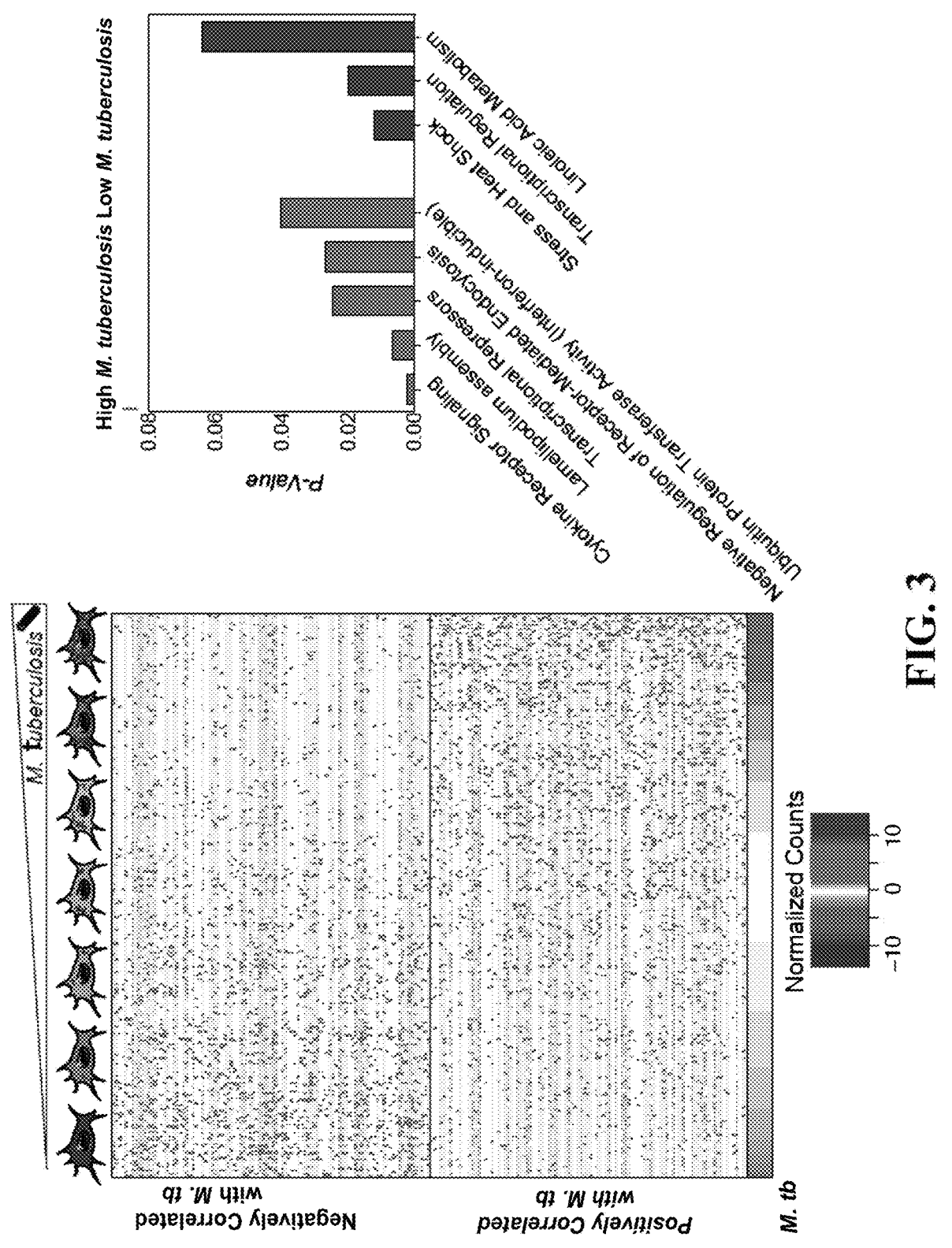
Figure 5:
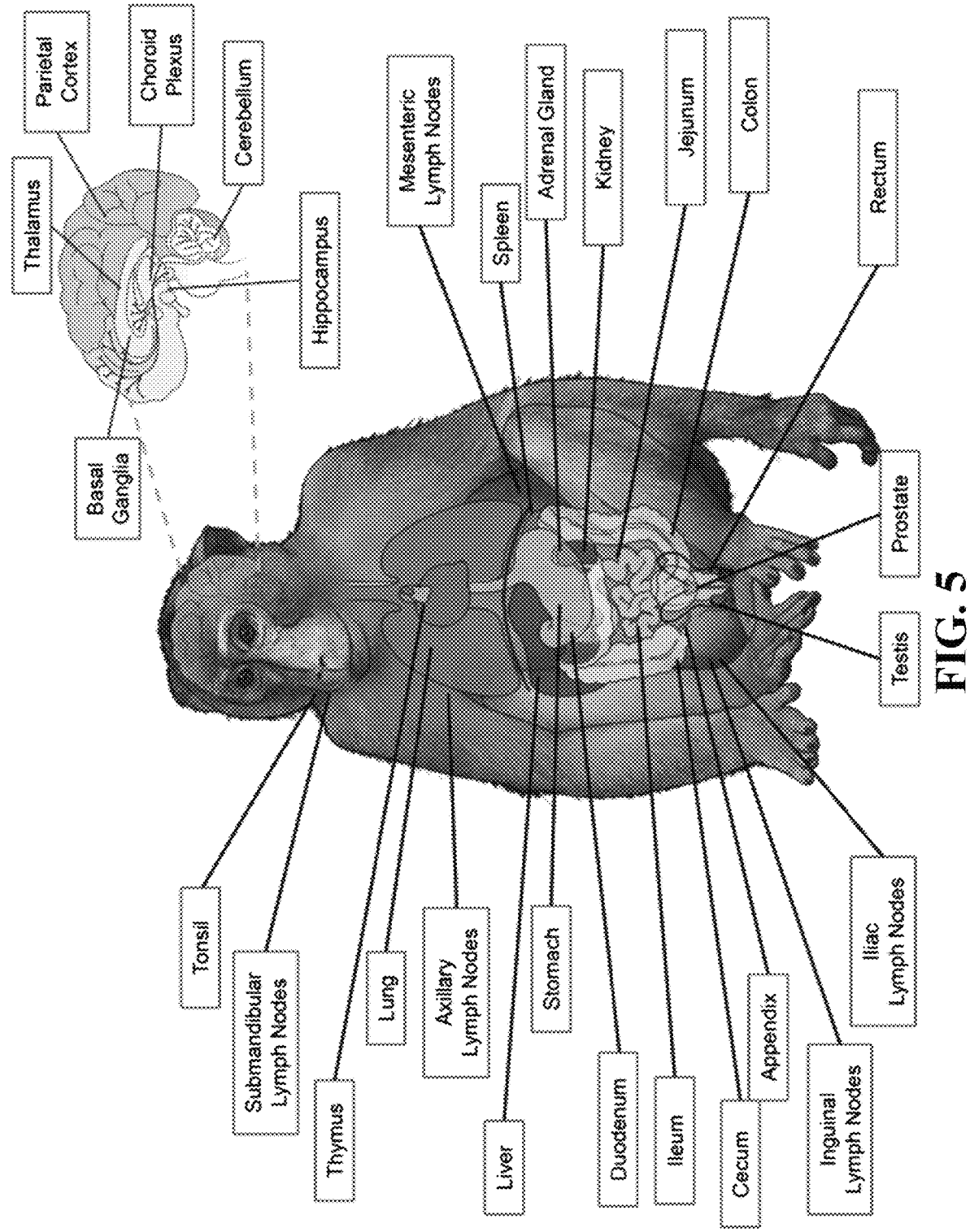
FIG. 5—Non-human primate model showing examples of cells and tissues useful for elaborating gene signatures associated with diseases and disorders.
Figure 10:
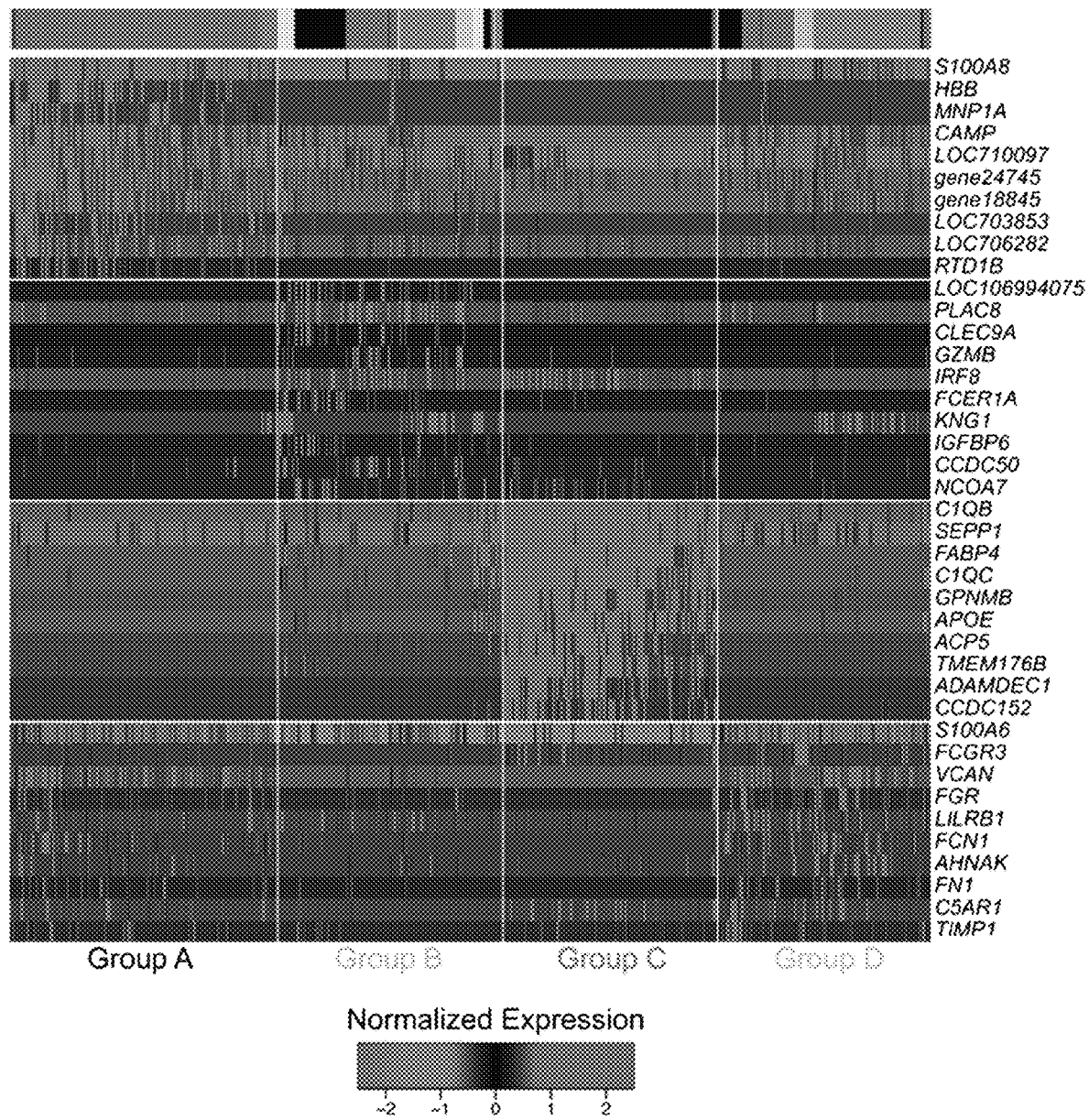
FIG. 10—Macrophage expression profiles correspond with tissues of origin.
Figure 11:
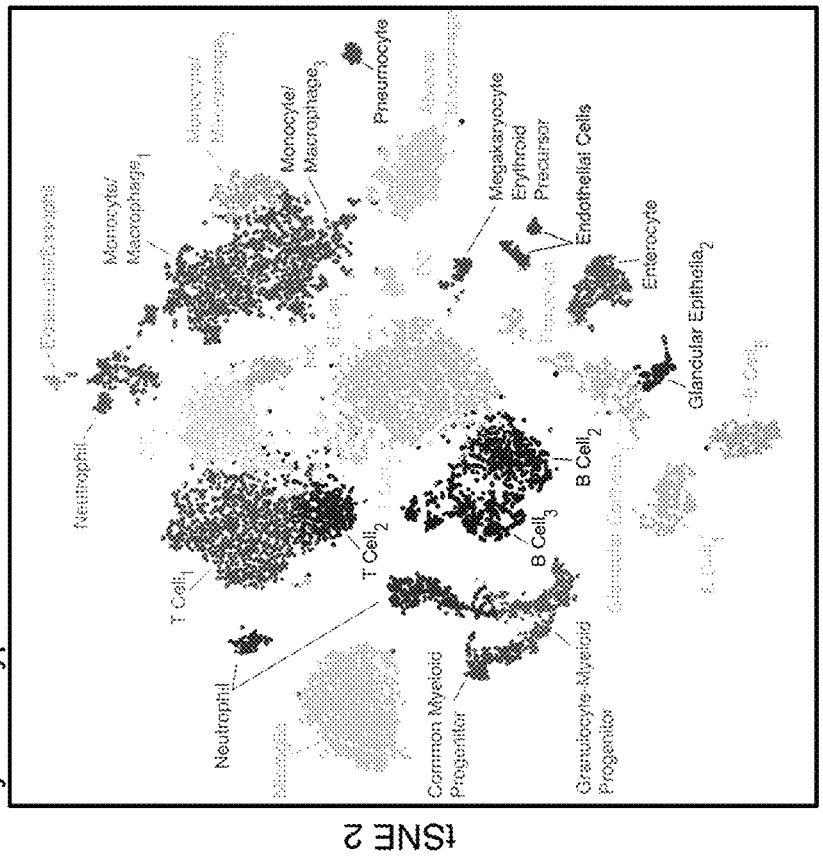
FIG. 11—includes t-distributed stochastic neighbor embedding (t-SNE) plots of Single single cell profiles define cells by tissue (left) and cell type (right).
Figure 11:
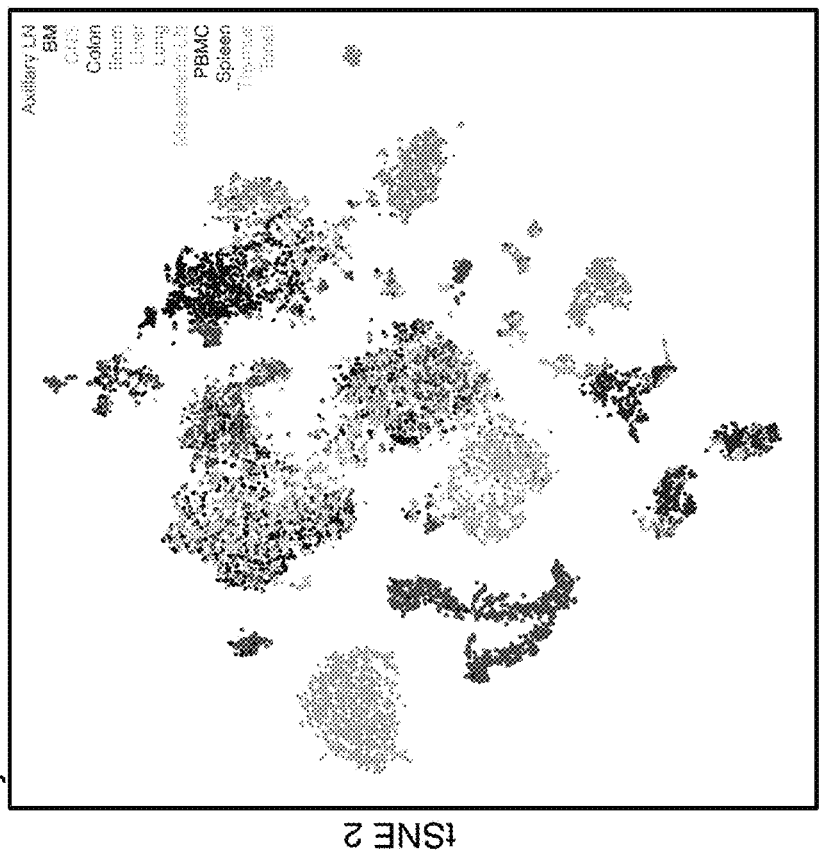
Figure 12A:
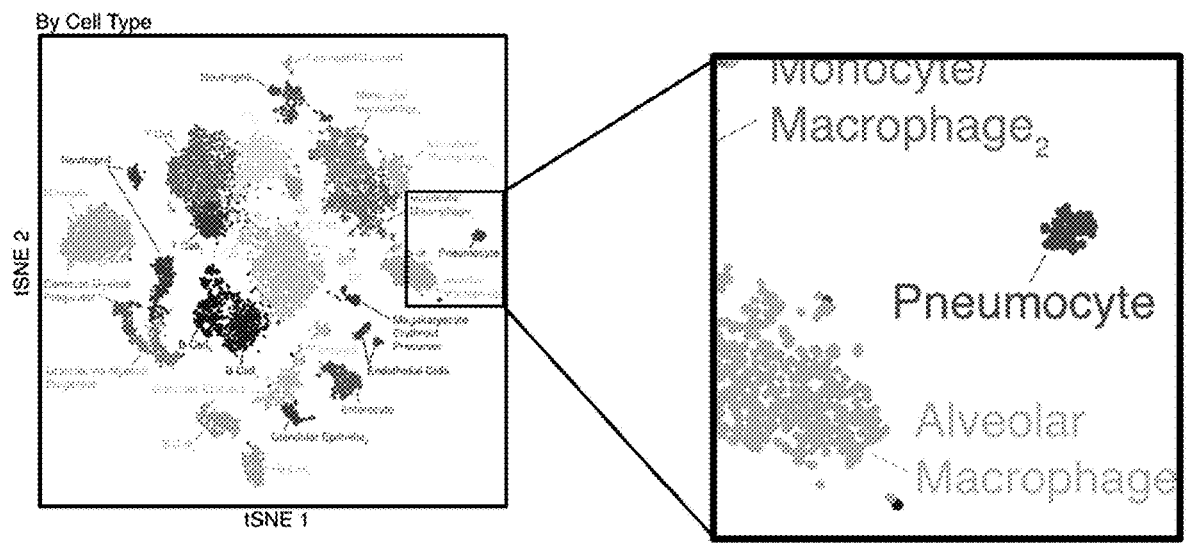
FIG. 12A-12B—Identification of pneumocyte (FIG. 12A) and NK (FIG. 12B) cell clusters via t-SNE plots.
Figure 12B:
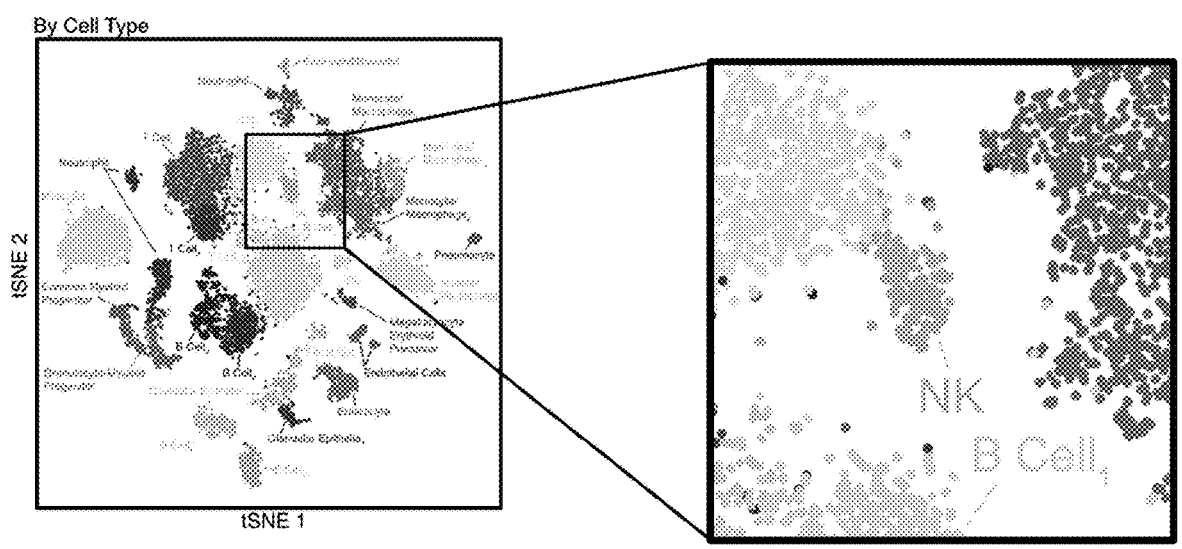
Figure 13:
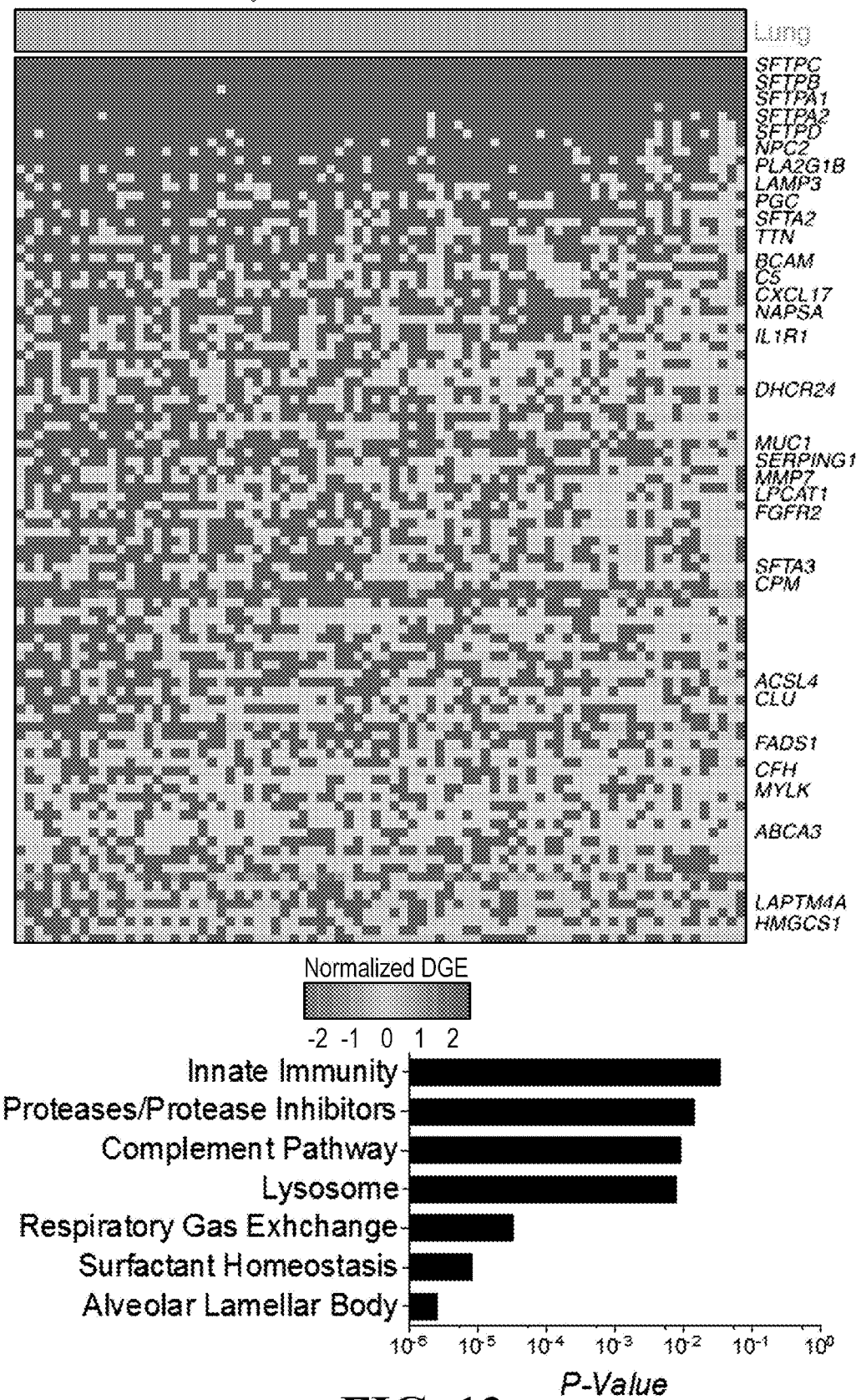
FIG. 13—Gene expression in pneumocytes indicates tissue-dependence (shown as normalized differential gene expression (DGE)).
Figure 14:
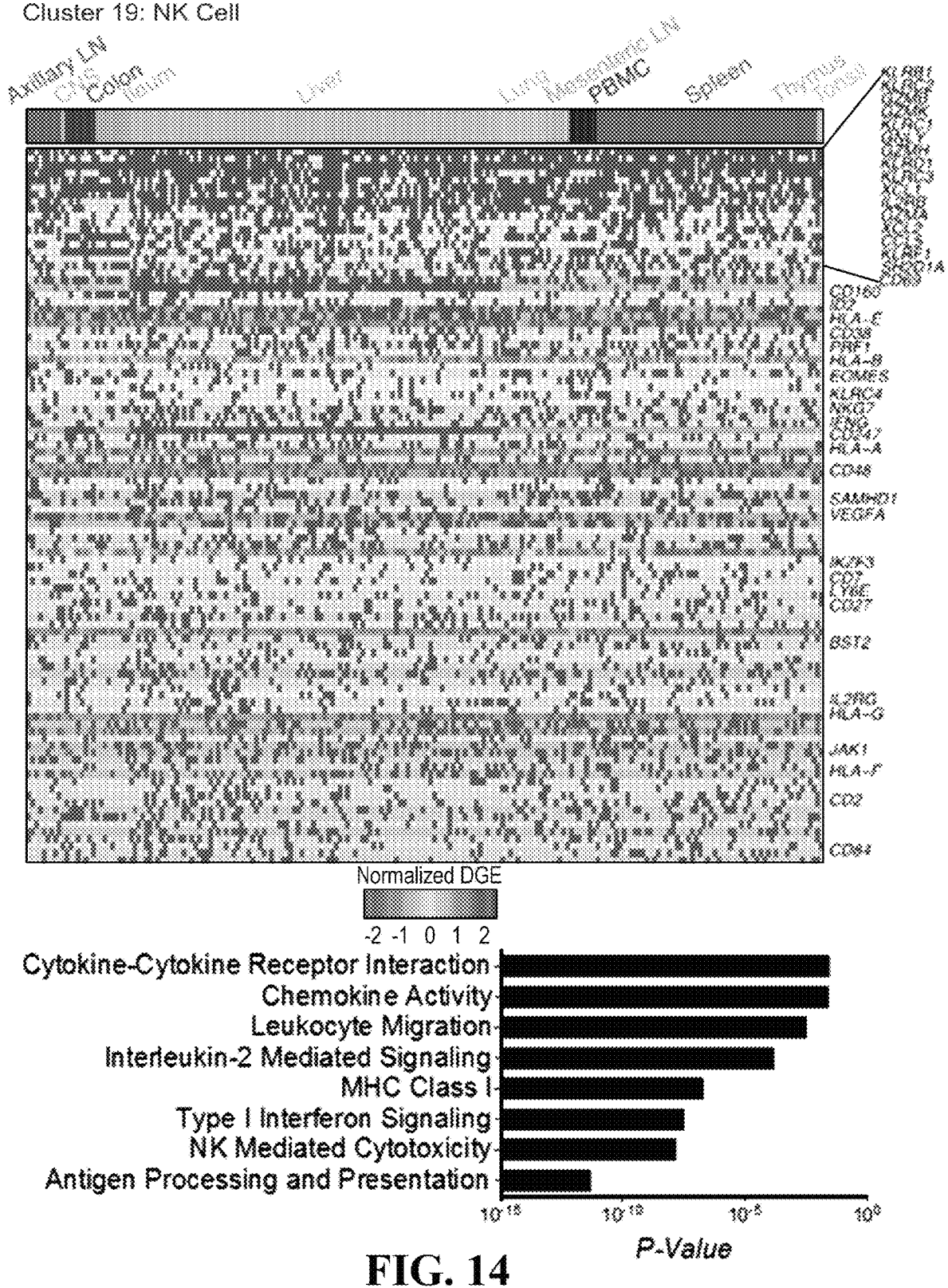
FIG. 14—Gene expression in NK cells indicates common functions and potential differences driven by tissue-of-origin (shown as normalized differential gene expression (DGE)).
Figure 15:
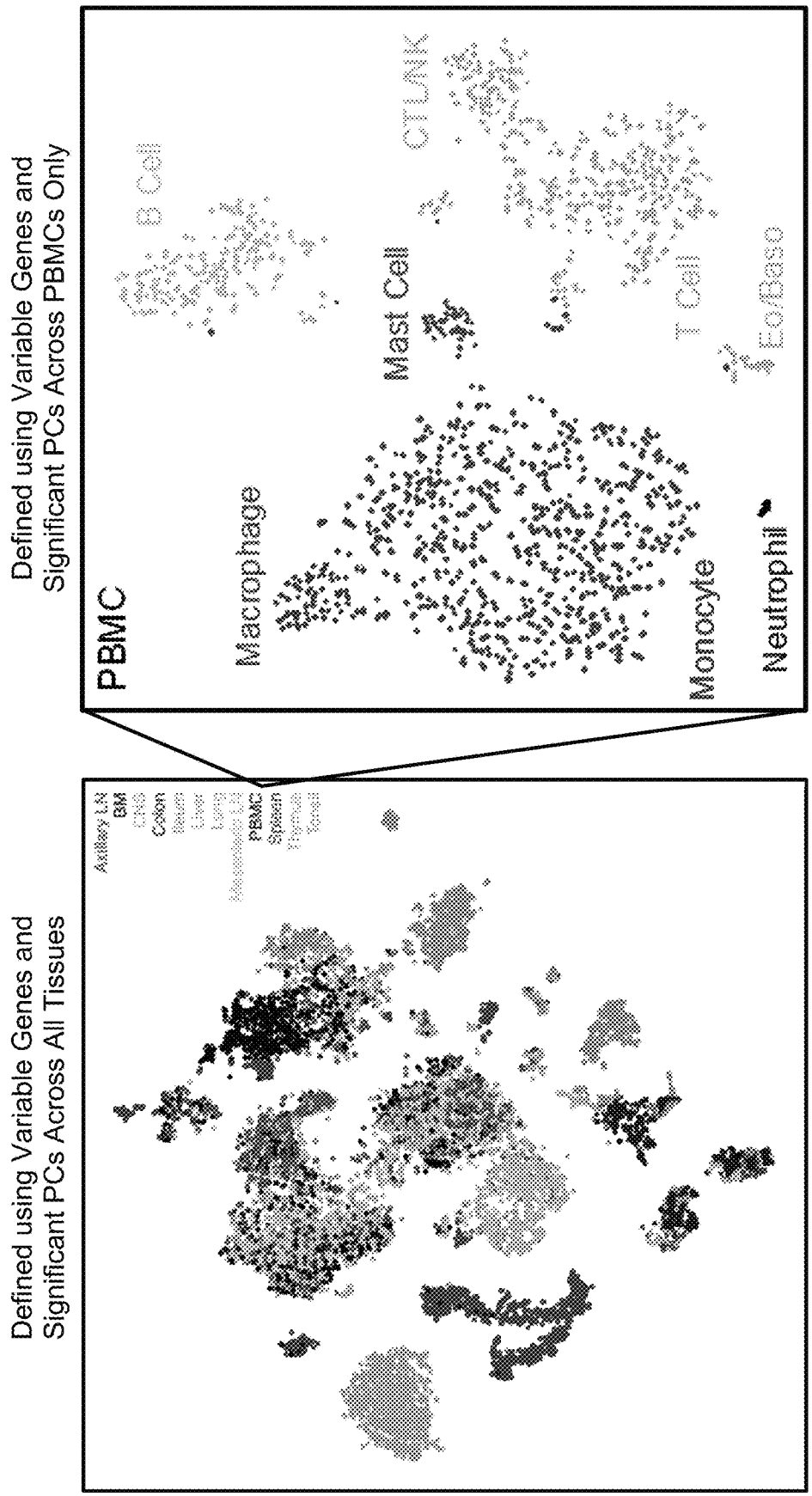
FIG. 15—Cell resolution looking at individual tissues.
Figure 16:
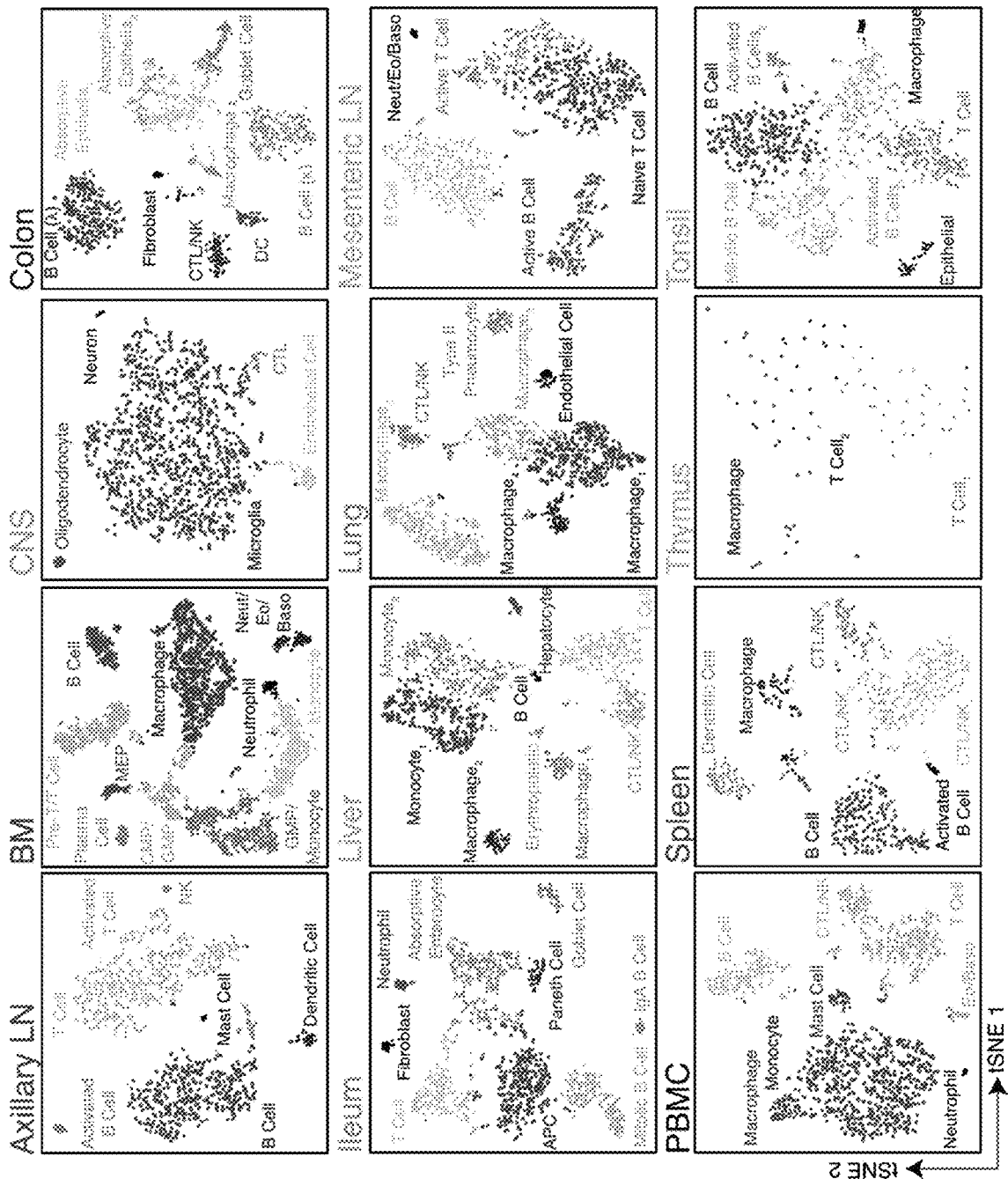
FIG. 16—includes t-SNE plots of cell expression profiles by tissue.
Figure 17:
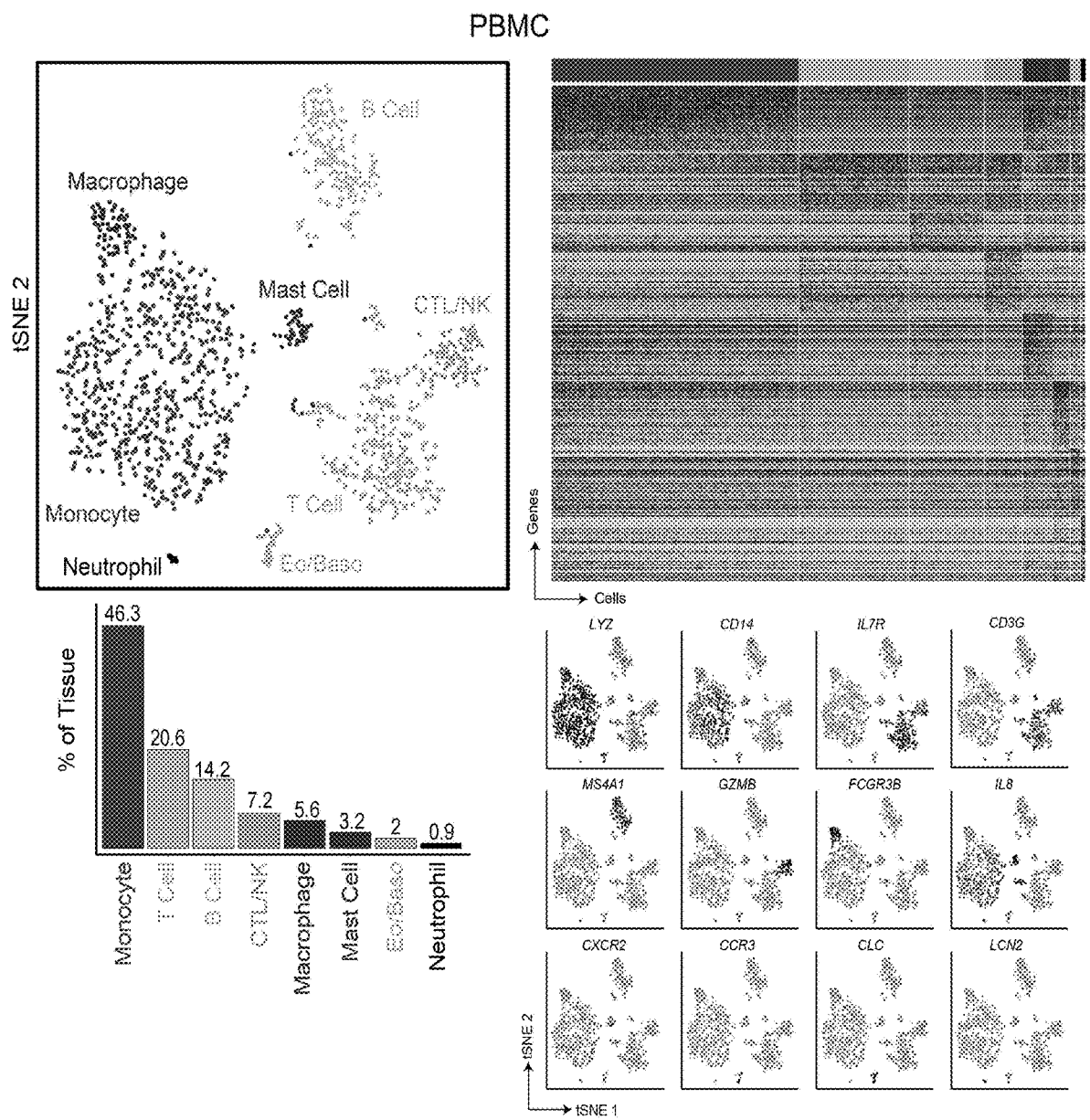
FIG. 17—Gene expression in PBMCs showing individual cell types and correlation with gene groups in t-SNE plots.
Figure 18:
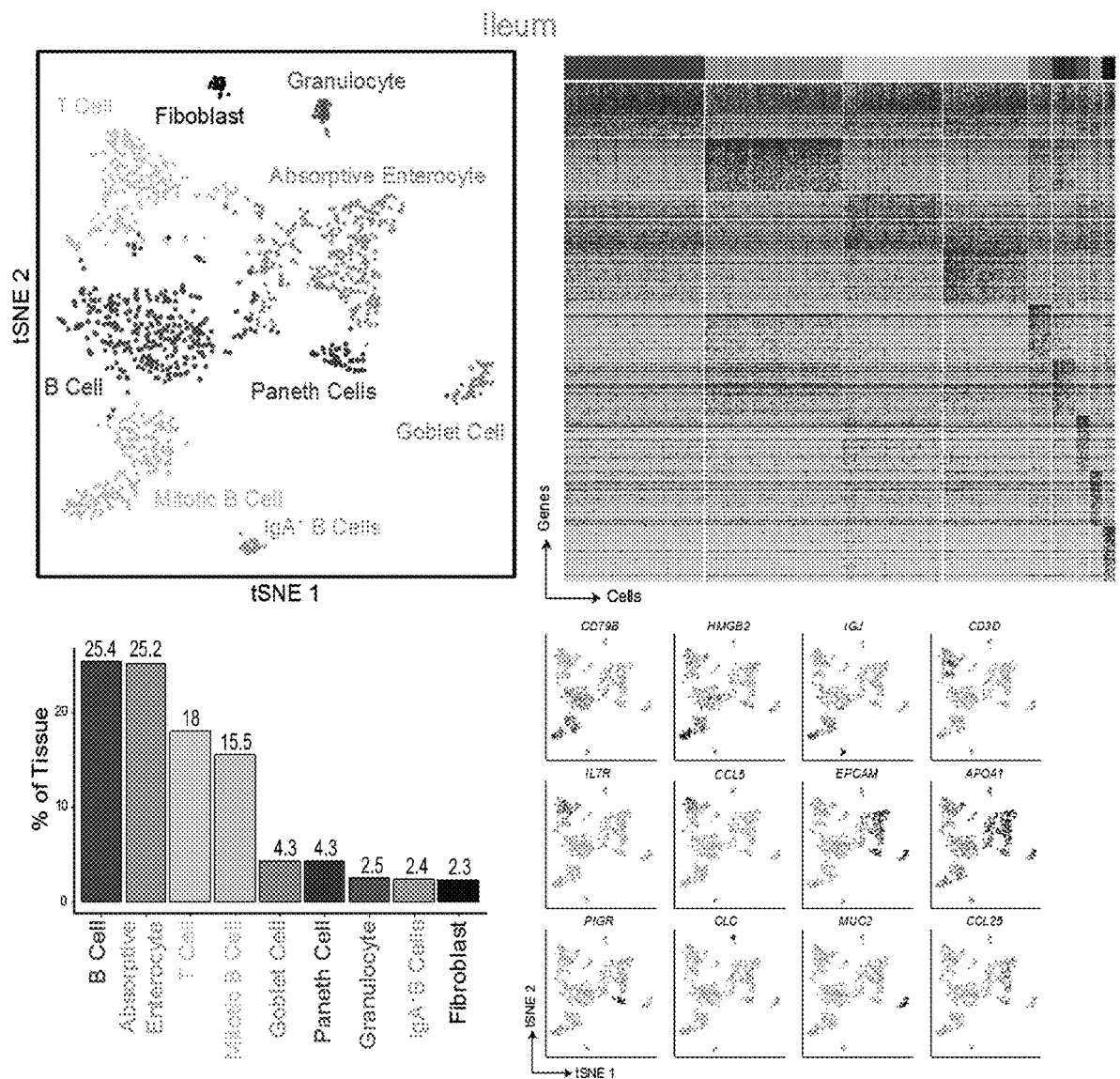
FIG. 18—Gene expression of cells in Ileum showing individual cell types and correlation with gene groups in t-SNE plots.

Based on single cell whole transcriptome amplification, genes whose expression are positively (Table 1) or negatively (Table 2) correlated with MTB infection have been identified. The correlated genes are clustered according to their function(s) (Tables 1 and 2). Further, genes and pathways that are correlated with low MOI (FIG. 2 E, top, FIGS. 3-4A-4B) and high MOI (FIG. 2E, bottom, Figures FIGS. 3-4A-4B) are also identified. Particularly, the TNFR2 pathway, NOS1 pathway, ETS pathway, NTHI pathway, IL1R pathway, NFkB pathway, MAL pathway, ALK pathway, RAC1 pathway, CCR3 pathway, GCR pathway, PPAR signaling pathway, PPARA activation of gene expression, PPARA pathway, amyotrophic lateral sclerosis pathway, activation of BH3 proteins, SNARE interaction for vesicular transport, Golgi associated vesicle biogenesis, TGF beta signaling pathway, TGF beta receptor signaling activates SMADS, signaling by TGF beta receptor complex, Hematopoietic cell lineage, leishmanial infection, glycosaminoglycan biosynthesis and chondroitin sulfate biosynthesis, metabolism of vitamins and cofactors, fatty Acyl CoA biosynthesis, synthesis, secretion, and inactivation of GLP1, incretin synthesis, secretion, and inactivation, fatty acid triacylglycerol and ketone body metabolism, glycosaminoglycan metabolism, triglyceride biosynthesis, cytokine receptor signaling, lamellipodium assembly, transcriptional repressors, negative regulation of receptor mediated endocytosis, and ubiquitin protein transfer activity, IFNB1, TREX1, CXCL10, IFNA17 in cytosolic DNA sensing pathway, HDAC9, CDKN2C, PPP2R2C, CCND1 in cyclins and cell cycle regulation appear to correlate with high MTB MOI. The PARRXR pathway, transcription, RNA Pol I/III Transcription, PI3k Events in ERBB2 signaling, signaling by ERBB2, signaling by EGFR in cancer, chromosome maintenance, telomere maintenance, Acyl chain remodeling, N glycan biosynthesis and protein transfer, respiratory electron transport, chemiosmotic coupling, glycine, serine, and threonine metabolism, TCA cycle, glycolysis and gluconeogenesis, phenylalanine metabolism, purine metabolism, stress and heat shock, transcriptional regulation, linoleic acid metabolism, REGIP, CD69, CD22, SFTPA1, CD72 involved in sugar binding, IFNA1, IFNA13, DHX58, TRADD in RIG-I-like receptor singling pathway, FCER1A, SDC1, CD69, CD276, PCSK9, CD22, TP53I13, GPC1 in cell surface recognition, BAG4 in SODD/TNFR1 signaling pathway, IFNA1 and IFNA13 interferon alpha/beta receptor binding; IL36 G, ARG2, IL1F10, MAP4K4 in 11-10 signaling in appear to correlate with low MTB MOI (FIGS. 8-10).

TABLE 1

Genes Positively Correlated with TB

| Term | Count | Genes |
| --- | --- | --- |
| Enrichment Score: 1.6292421548153069 | | |
| GO:0045806~negative regulation of endocytosis | 3 | RAC1, APOC1, NR1H3 |
| GO:0060627~regulation of vesicle-mediated transport | 4 | RAB3C, RAC1, APOC1, NR1H3 |
| GO:0045834~positive regulation of lipid metabolic process | 3 | RAC1, APOC1, NR1H3 |
| GO:0030100~regulation of endocytosis | 3 | RAC1, APOC1, NR1H3 |
| GO:0019216~regulation of lipid metabolic process | 3 | RAC1, APOC1, NR1H3 |

TABLE 1-continued

Genes Positively Correlated with TB

| Term | Count | Genes |
|---|---|---|
| GO:0051051~negative regulation of transport | 3 | RAC1, APOC1, NR1H3 |
| GO:0051129~negative regulation of cellular component organization | 3 | RAC1, APOC1, NR1H3 |
| Enrichment Score: 1.0362232095437491 | | |
| GO:0065003~macromolecular complex assembly | 8 | TARBP2, TSPYL2, MED27, RAC1, APOC1, H2AFY, NAP1L3, ZW10 |
| GO:0043933~macromolecular complex subunit organization | 8 | TARBP2, TSPYL2, MED27, RAC1, APOC1, H2AFY, NAP1L3, ZW10 |
| GO:0034622~cellular macromolecular complex assembly | 5 | TARBP2, TSPYL2, RAC1, H2AFY, NAP1L3 |
| GO:0006334~nucleosome assembly | 3 | TSPYL2, H2AFY, NAP1L3 |
| GO:0031497~chromatin assembly | 3 | TSPYL2, H2AFY, NAP1L3 |
| GO:0065004~protein-DNA complex assembly | 3 | TSPYL2, H2AFY, NAP1L3 |
| GO:0034728~nucleosome organization | 3 | TSPYL2, H2AFY, NAP1L3 |
| GO:0034621~cellular macromolecular complex subunit organization | 5 | TARBP2, TSPYL2, RAC1, H2AFY, NAP1L3 |
| GO:0006323~DNA packaging | 3 | TSPYL2, H2AFY, NAP1L3 |
| GO:0006333~chromatin assembly or disassembly | 3 | TSPYL2, H2AFY, NAP1L3 |
| GO:0051276~chromosome organization | 5 | TSPYL2, H2AFY, NAP1L3, RNF20, ZW10 |
| chromatin regulator | 3 | TSPYL2, H2AFY, RNF20 |
| GO:0006325~chromatin organization | 4 | TSPYL2, H2AFY, NAP1L3, RNF20 |
| GO:0016568~chromatin modification | 3 | TSPYL2, H2AFY, RNF20 |
| GO:0006461~protein complex assembly | 3 | MED27, RAC1, ZW10 |
| GO:0070271~protein complex biogenesis | 3 | MED27, RAC1, ZW10 |
| Enrichment Score: 0.9651359055052946 | | |
| ubl conjugation pathway | 6 | HERC6, UCHL5, KLHL12, TRIM63, KLHL3, RNF20 |
| GO:0006508~proteolysis | 9 | CAPN11, HERC6, UCHL5, KLHL12, MMP16, TRIM63, KLHL3, RNF20, DHCR24 |
| GO:0043632~modification-dependent macromolecule catabolic process | 6 | HERC6, UCHL5, KLHL12, TRIM63, KLHL3, RNF20 |
| GO:0019941~modification-dependent protein catabolic process | 6 | HERC6, UCHL5, KLHL12, TRIM63, KLHL3, RNF20 |
| GO:0051603~proteolysis involved in cellular protein catabolic process | 6 | HERC6, UCHL5, KLHL12, TRIM63, KLHL3, RNF20 |
| GO:0009057~macromolecule catabolic process | 7 | HERC6, UCHL5, KLHL12, TRIM63, KLHL3, RNF20, DHCR24 |
| ligase | 4 | HERC6, ACSL4, TRIM63, RNF20 |
| GO:0044257~cellular protein catabolic process | 6 | HERC6, UCHL5, KLHL12, TRIM63, KLHL3, RNF20 |
| GO:0030163~protein catabolic process | 6 | HERC6, UCHL5, KLHL12, TRIM63, KLHL3, RNF20 |
| GO:0044265~cellular macromolecule catabolic process | 6 | HERC6, UCHL5, KLHL12, TRIM63, KLHL3, RNF20 |
| GO:0016881~acid-amino acid ligase activity | 3 | HERC6, TRIM63, RNF20 |
| GO:0016879~ligase activity, forming carbon-nitrogen bonds | 3 | HERC6, TRIM63, RNF20 |
| GO:0006511~ubiquitin-dependent protein catabolic process | 3 | UCHL5, TRIM63, RNF20 |
| Enrichment Score: 0.8195579938188856 | | |
| hsa04010:MAPK signaling pathway | 4 | DUSP1, RAC1, PPP3R1, IL1A |
| GO:0006915~apoptosis | 6 | RAC1, PPP3R1, LGALS12, IL1A, DHCR24, FGD4 |
| GO:0043065~positive regulation of apoptosis | 5 | DUSP1, RAC1, PPP3R1, LGALS12, FGD4 |
| GO:0043068~positive regulation of programmed cell death | 5 | DUSP1, RAC1, PPP3R1, LGALS12, FGD4 |
| GO:0010942~positive regulation of cell death | 5 | DUSP1, RAC1, PPP3R1, LGALS12, FGD4 |
| GO:0012501~programmed cell death | 6 | RAC1, PPP3R1, LGALS12, IL1A, DHCR24, FGD4 |

TABLE 1-continued

Genes Positively Correlated with TB

| Term | Count | Genes |
| --- | --- | --- |
| GO:0042981~regulation of apoptosis | 7 | DUSP1, RAC1, PPP3R1, LGALS12, IL1A, DHCR24, FGD4 |
| GO:0043067~regulation of programmed cell death | 7 | DUSP1, RAC1, PPP3R1, LGALS12, IL1A, DHCR24, FGD4 |
| GO:0010941~regulation of cell death | 7 | DUSP1, RAC1, PPP3R1, LGALS12, IL1A, DHCR24, FGD4 |
| GO:0008219~cell death | 6 | RAC1, PPP3R1, LGALS12, IL1A, DHCR24, FGD4 |
| GO:0016265~death | 6 | RAC1, PPP3R1, LGALS12, IL1A, DHCR24, FGD4 |
| GO:0019899~enzyme binding | 4 | RAC1, RNF20, DHCR24, FGD4 |
| GO:0006917~induction of apoptosis | 3 | RAC1, LGALS12, FGD4 |
| GO:0012502~induction of programmed cell death | 3 | RAC1, LGALS12, FGD4 |
| GO:0005829~cytosol | 6 | RAB3C, APLF, HERC6, RAC1, PPP3R1, FGD4 |
| Enrichment Score: 0.7891679915209755 | | |
| lipoprotein | 7 | RAB3C, RAPSN, RAC1, APOC1, PPP3R1, RHOD, IL1A |
| GO:0009898~internal side of plasma membrane | 5 | VEPH1, RAB3C, RAPSN, RAC1, RHOD |
| short sequence motif:Effector region | 3 | RAB3C, RAC1, RHOD |
| lipid moiety-binding region:S-geranylgeranyl cysteine | 3 | RAB3C, RAC1, RHOD |
| methylation | 4 | RAB3C, RAC1, H2AFY, RHOD |
| IPR013753:Ras | 3 | RAB3C, RAC1, RHOD |
| nucleotide phosphate-binding region:GTP | 4 | RAB3C, RAC1, RHOD, RRAGD |
| IPR001806:Ras GTPase | 3 | RAB3C, RAC1, RHOD |
| prenylation | 3 | RAB3C, RAC1, RHOD |
| gtp-binding | 4 | RAB3C, RAC1, RHOD, RRAGD |
| GO:0007264~small GTPase mediated signal transduction | 4 | RAB3C, RAC1, RHOD, DHCR24 |
| IPR005225:Small GTP-binding protein | 3 | RAB3C, RAC1, RHOD |
| GO:0005525~GTP binding | 4 | RAB3C, RAC1, RHOD, RRAGD |
| GO:0019001~guanyl nucleotide binding | 4 | RAB3C, RAC1, RHOD, RRAGD |
| GO:0032561~guanyl ribonucleotide binding | 4 | RAB3C, RAC1, RHOD, RRAGD |
| GO:0007242~intracellular signaling cascade | 7 | RAB3C, DUSP1, RAC1, RHOD, DHCR24, MTNR1A, FGD4 |
| nucleotide-binding | 6 | RAB3C, APLF, RAC1, RHOD, ACSL4, RRAGD |
| GO:0017076~purine nucleotide binding | 7 | RAB3C, RAC1, ZNF12, RHOD, ACSL4, RRAGD, DHCR24 |
| GO:0000166~nucleotide binding | 8 | RAB3C, APLF, RAC1, ZNF12, RHOD, ACSL4, RRAGD, DHCR24 |
| GO:0032553~ribonucleotide binding | 6 | RAB3C, RAC1, ZNF12, RHOD, ACSL4, RRAGD |
| GO:0032555~purine ribonucleotide binding | 6 | RAB3C, RAC1, ZNF12, RHOD, ACSL4, RRAGD |
| Enrichment Score: 0.7538123661108601 | | |
| GO:0034622~cellular macromolecular complex assembly | 5 | TARBP2, TSPYL2, RAC1, H2AFY, NAP1L3 |
| GO:0034621~cellular macromolecular complex subunit organization | 5 | TARBP2, TSPYL2, RAC1, H2AFY, NAP1L3 |
| GO:0043549~regulation of kinase activity | 4 | TARBP2, TSPYL2, RAC1, FGD4 |
| GO:0051338~regulation of transferase activity | 4 | TARBP2, TSPYL2, RAC1, FGD4 |
| GO:0042325~regulation of phosphorylation | 4 | TARBP2, TSPYL2, RAC1, FGD4 |
| GO:0019220~regulation of phosphate metabolic process | 4 | TARBP2, TSPYL2, RAC1, FGD4 |
| GO:0051174~regulation of phosphorus metabolic process | 4 | TARBP2, TSPYL2, RAC1, FGD4 |
| GO:0045859~regulation of protein kinase activity | 3 | TARBP2, TSPYL2, FGD4 |

TABLE 1-continued

Genes Positively Correlated with TB

| Term | Count | Genes |
|---|---|---|
| Enrichment Score: 0.7376548894910318 | | |
| zinc-finger | 14 | PRDM8, ASXL3, SNAI3, APLF, RAPSN, ZDHHC7, GLIS1, ZNF24, ZNF12, HNF4G, TRIM63, RNF20, FGD4, NR1H3 |
| zinc | 15 | PRDM8, ASXL3, SNAI3, APLF, RAPSN, ZDHHC7, GLIS1, ZNF24, ZNF12, MMP16, HNF4G, TRIM63, RNF20, FGD4, NR1H3 |
| GO:0008270~zinc ion binding | 15 | PRDM8, ASXL3, SNAI3, APLF, RAPSN, ZDHHC7, GLIS1, ZNF24, ZNF12, MMP16, HNF4G, TRIM63, RNF20, FGD4, NR1H3 |
| repressor | 5 | ASXL3, SNAI3, GLIS1, ZNF24, MSC |
| nucleus | 22 | ASXL3, APLF, GLIS1, LGALS12, ZNF24, ZNF12, NAP1L3, HNF4G, TRIM63, RRAGD, MSC, NOP10, PRDM8, TARBP2, SNAI3, MEIS2, TSPYL2, DUSP26, MED27, H2AFY, RNF20, NR1H3 |
| GO:0043169~cation binding | 22 | ASXL3, PCDHGA10, APLF, CRTAC1, TRPV2, ZDHHC7, GLIS1, APOC1, PPP3R1, ZNF24, ZNF12, MMP16, HNF4G, TRIM63, PRDM8, SNAI3, CAPN11, RAPSN, ACSL4, RNF20, NR1H3, FGD4 |
| GO:0043167~ion binding | 22 | ASXL3, PCDHGA10, APLF, CRTAC1, TRPV2, ZDHHC7, GLIS1, APOC1, PPP3R1, ZNF24, ZNF12, MMP16, HNF4G, TRIM63, PRDM8, SNAI3, CAPN11, RAPSN, ACSL4, RNF20, NR1H3, FGD4 |
| metal-binding | 15 | PRDM8, ASXL3, SNAI3, APLF, RAPSN, ZDHHC7, GLIS1, ZNF24, ZNF12, MMP16, HNF4G, TRIM63, RNF20, FGD4, NR1H3 |
| transcription regulation | 11 | PRDM8, ASXL3, SNAI3, TSPYL2, GLIS1, MED27, ZNF24, ZNF12, HNF4G, MSC, NR1H3 |
| zinc finger region:C2H2-type 3 | 5 | PRDM8, SNAI3, GLIS1, ZNF24, ZNF12 |
| GO:0046872~metal ion binding | 21 | ASXL3, PCDHGA10, APLF, CRTAC1, TRPV2, ZDHHC7, GLIS1, PPP3R1, ZNF24, ZNF12, MMP16, HNF4G, TRIM63, PRDM8, SNAI3, CAPN11, RAPSN, ACSL4, RNF20, NR1H3, FGD4 |
| Transcription | 11 | PRDM8, ASXL3, SNAI3, TSPYL2, GLIS1, MED27, ZNF24, ZNF12, HNF4G, MSC, NR1H3 |
| IPR007087:Zinc finger, C2H2-type | 6 | PRDM8, SNAI3, GLIS1, ZNF24, ZNF12, NR1H3 |
| GO:0046914~transition metal ion binding | 15 | PRDM8, ASXL3, SNAI3, APLF, RAPSN, ZDHHC7, GLIS1, ZNF24, ZNF12, MMP16, HNF4G, TRIM63, RNF20, FGD4, NR1H3 |
| dna-binding | 10 | PRDM8, SNAI3, MEIS2, GLIS1, ZNF24, H2AFY, ZNF12, HNF4G, MSC, NR1H3 |
| GO:0045449~regulation of transcription | 14 | ASXL3, GLIS1, ZNF24, ZNF12, HNF4G, MSC, PRDM8, TARBP2, SNAI3, MEIS2, TSPYL2, MED27, RNF20, NR1H3 |
| GO:0030528~transcription regulator activity | 9 | SNAG, MEIS2, GLIS1, MED27, ZNF24, HNF4G, MSC, RNF20, NR1H3 |
| GO:0006355~regulation of transcription, DNA-dependent | 10 | TARBP2, SNAI3, MEIS2, GLIS1, MED27, ZNF24, ZNF12, HNF4G, RNF20, NR1H3 |
| zinc finger region:C2H2-type 1 | 4 | SNAI3, GLIS1, ZNF24, ZNF12 |
| GO:0051252~regulation of RNA metabolic process | 10 | TARBP2, SNAI3, MEIS2, GLIS1, MED27, ZNF24, ZNF12, HNF4G, RNF20, NR1H3 |
| GO:0003677~DNA binding | 12 | PRDM8, SNAI3, MEIS2, TSPYL2, GLIS1, ZNF24, H2AFY, ZNF12, HNF4G, MSC, ZW10, NR1H3 |

TABLE 1-continued

Genes Positively Correlated with TB

| Term | Count | Genes |
|---|---|---|
| zinc finger region:C2H2-type 4 | 4 | SNAI3, GLIS1, ZNF24, ZNF12 |
| GO:0006350~transcription | 11 | PRDM8, ASXL3, SNAI3, TSPYL2, GLIS1, MED27, ZNF24, ZNF12, HNF4G, MSC, NR1H3 |
| GO:0003700~transcription factor activity | 6 | SNAI3, MEIS2, ZNF24, HNF4G, MSC, NR1H3 |
| zinc finger region:C2H2-type 2 | 4 | PRDM8, SNAI3, ZNF24, NF12 |
| IPR015880:Zinc finger, C2H2-like | 5 | PRDM8, SNAI3, GLIS1, ZNF24, ZNF12 |
| IPR013087:Zinc finger, C2H2-type/integrase, DNA-binding | 4 | SNAI3, GLIS1, ZNF24, ZNF12 |
| SM00355:ZnF C2H2 | 5 | PRDM8, SNAI3, GLIS1, ZNF24, ZNF12 |
| Enrichment Score: 0.695896167722095 | | |
| GO:0007610~behavior | 6 | CCL3, SLC1A3, CCL3L3, RAC1, ACSL4, MTNR1A |
| hsa04062:Chemokine signaling pathway | 3 | CCL3, CCL3L3, RAC1 |
| cytokine | 3 | CCL3, CCL3L3, IL1A |
| GO:0006935~chemotaxis | 3 | CCL3, CCL3L3, RAC1 |
| GO:0042330~taxis | 3 | CCL3, CCL3L3, RAC1 |
| GO:0006954~inflammatory response | 4 | CCL3, CCL3L3, RAC1, IL1A |
| GO:0009611~response to wounding | 5 | CCL3, SLC1A3, CCL3L3, RAC1, IL1A |
| GO:0005125~cytokine activity | 3 | CCL3, CCL3L3, IL1A |
| hsa04060: Cytokine-cytokine receptor interaction | 3 | CCL3, CCL3L3, IL1A |
| GO:0006952~defense response | 5 | CCL3, IL27RA, CCL3L3, RAC1, IL1A |
| GO:0007626~locomotory behavior | 3 | CCL3, CCL3L3, RAC1 |
| GO:0005615~extracellular space | 4 | CCL3, CCL3L3, APOC1, IL1A |
| GO:0006955~immune response | 4 | CCL3, IL27RA, CCL3L3, IL1A |
| GO:0042592~homeostatic process | 3 | CCL3, RAC1, IL1A |
| Enrichment Score: 0.6357971532121958 | | |
| GO:0044421~extracellular region part | 9 | CCL3, SLC1A3, HAPLN3, CRTAC1, CCL3L3, APOC1, MMP16, COL11A1, IL1A |
| GO:0005578~proteinaceous extracellular matrix | 5 | SLC1A3, HAPLN3, CRTAC1, MMP16, COL11A1 |
| GO:0031012~extracellular matrix | 5 | SLC1A3, HAPLN3, CRTAC1, MMP16, COL11A1 |
| extracellular matrix | 4 | HAPLN3, CRTAC1, MMP16, COL11A1 |
| Secreted | 9 | CCL3, HAPLN3, CRTAC1, CCL3L3, APOC1, MMP16, SERPINI1, COL11A1, IL1A |
| GO:0005576~extracellular region | 10 | CCL3, SLC1A3, HAPLN3, CRTAC1, CCL3L3, APOC1, MMP16, SERPINI1, COL11A1, IL1A |
| signal | 12 | PCDHGA10, CCL3, HAPLN3, IL27RA, CRTAC1, CCL3L3, APOC1, MMP16, SERPINI1, COL11A1, SDC2, DHCR24 |
| signal peptide | 12 | PCDHGA10, CCL3, HAPLN3, IL27RA, CRTAC1, CCL3L3, APOC1, MMP16, SERPINI1, COL11A1, SDC2, DHCR24 |
| GO:0007186~G-protein coupled receptor protein signaling pathway | 3 | CCL3, OR5K3, MTNR1A |
| disulfide bond | 7 | CCL3, HAPLN3, OR5K3, CRTAC1, CCL3L3, MMP16, MTNR1A |
| disulfide bond | 7 | CCL3, HAPLN3, OR5K3, CRTAC1, CCL3L3, MMP16, MTNR1A |
| Enrichment Score: 0.5695523811903586 | | |
| GO:0005730~nucleolus | 6 | MEIS2, TSPYL2, GLIS1, HNF4G, NOP10, RNF20 |
| GO:0051172~negative regulation of nitrogen compound metabolic process | 5 | MEIS2, TSPYL2, GLIS1, ZNF24, APOC1 |
| GO:0031327~negative regulation of cellular biosynthetic process | 5 | MEIS2, TSPYL2, GLIS1, ZNF24, APOC1 |
| GO:0009890~negative regulation of biosynthetic process | 5 | MEIS2, TSPYL2, GLIS1, ZNF24, APOC1 |
| GO:0010629~negative regulation of gene expression | 4 | TARBP2, MEIS2, GLIS1, ZNF24 |

TABLE 1-continued

Genes Positively Correlated with TB

| Term | Count | Genes |
| --- | --- | --- |
| GO:0045934~negative regulation of nucleobase, nucleoside, nucleotide and nucleic acid metabolic process | 4 | MEIS2, TSPYL2, GLIS1, ZNF24 |
| GO:0010605~negative regulation of macromolecule metabolic process | 5 | TARBP2, MEIS2, TSPYL2, GLIS1, ZNF24 |
| GO:0010558~negative regulation of macromolecule biosynthetic of process | 4 | MEIS2, TSPYL2, GLIS1, ZNF24 |
| GO:0016481~negative regulation of transcription | 3 | MEIS2, GLIS1, ZNF24 |
| Enrichment Score: 0.5511302619302495 | | |
| zinc finger region:RING-type | 3 | RAPSN, TRIM63, RNF20 |
| IPR018957:Zinc finger, C3HC4 RING-type | 3 | RAPSN, TRIM63, RNF20 |
| IPR017907:Zinc finger, RING-type, conserved site | 3 | RAPSN, TRIM63, RNF20 |
| IPR001841:Zinc finger, RING-type | 3 | RAPSN, TRIM63, RNF20 |
| SM00184:RING | 3 | RAPSN, TRIM63, RNF20 |
| Enrichment Score: 0.5214545487219902 | | |
| GO:0009628~response to abiotic stimulus | 5 | SLC1A3, DUSP1, TRPV2, RAC1, COL11A1 |
| GO:0050890~cognition | 6 | CNNM4, SLC1A3, OR5K3, TRPV2, ACSL4, COL11A1 |
| GO:0050877~neurological system process | 7 | CNNM4, SLC1A3, OR5K3, RAPSN, TRPV2, ACSL4, COL11A1 |
| GO:0007600~sensory perception | 5 | CNNM4, SLC1A3, OR5K3, TRPV2, COL11A1 |
| GO:0006811~ion transport | 3 | CNNM4, SLC1A3, TRPV2 |
| Enrichment Score: 0.5182365429181518 | | |
| GO:0006366~transcription from RNA polymerase II promoter | 3 | MED27, HNF4G, MSC |
| GO:0006351~transcription, DNA-dependent | 3 | MED27, HNF4G, MSC |
| GO:0032774~RNA biosynthetic process | 3 | MED27, HNF4G, MSC |
| Enrichment Score: 0.5017372401227738 | | |
| GO:0016337~cell-cell adhesion | 3 | PCDHGA10, CLDN6, COL11A1 |
| GO:0007155~cell adhesion | 5 | PCDHGA10, HAPLN3, CLDN6, RAC1, COL11A1 |
| GO:0022610~biological adhesion | 5 | PCDHGA10, HAPLN3, CLDN6, RAC1, COL11A1 |
| Enrichment Score: 0.474737606246611 | | |
| GO:0003712~transcription cofactor activity | 5 | MEIS2, MED27, MSC, RNF20, NR1H3 |
| GO:0005730~nucleolus | 6 | MEIS2, TSPYL2, GLIS1, HNF4G, NOP10, RNF20 |
| GO:0008134~transcription factor binding | 5 | MEIS2, MED27, MSC, RNF20, NR1H3 |
| GO:0006357~regulation of transcription from RNA polymerase II promoter | 6 | TARBP2, MEIS2, GLIS1, MED27, HNF4G, NR1H3 |
| GO:0003713~transcription coactivator activity | 3 | MED27, RNF20, NR1H3 |
| GO:0016563~transcription activator activity | 4 | MED27, HNF4G, RNF20, NR1H3 |
| GO:0045449~regulation of transcription | 14 | ASXL3, GLIS1, ZNF24, ZNF12, HNF4G, MSC, PRDM8, TARBP2, SNAI3, MEIS2, TSPYL2, MED27, RNF20, NR1H3 |
| GO:0030528~transcription regulator activity | 9 | SNAI3, MEIS2, GLIS1, MED27, ZNF24, HNF4G, MSC, RNF20, NR1H3 |
| GO:0010557~positive regulation of macromolecule biosynthetic process | 5 | MEIS2, GLIS1, RNF20, IL1A, NR1H3 |
| GO:0006355~regulation of transcription, DNA-dependent | 10 | TARBP2, SNAI3, MEIS2, GLIS1, MED27, ZNF24, ZNF12, HNF4G, RNF20, NR1H3 |
| GO:0031328~positive regulation of cellular biosynthetic process | 5 | MEIS2, GLIS1, RNF20, IL1A, NR1H3 |
| GO:0009891~positive regulation of biosynthetic process | 5 | MEIS2, GLIS1, RNF20, IL1A, NR1H3 |

TABLE 1-continued

Genes Positively Correlated with TB

| Term | Count | Genes |
| --- | --- | --- |
| GO:0051252~regulation of RNA metabolic process | 10 | TARBP2, SNAI3, MEIS2, GLIS1, MED27, ZNF24, ZNF12, HNF4G, RNF20, NR1H3 |
| GO:0045941~positive regulation of transcription | 4 | MEIS2, GLIS1, RNF20, NR1H3 |
| GO:0010628~positive regulation of gene expression | 4 | MEIS2, GLIS1, RNF20, NR1H3 |
| GO:0043228~non-membrane-bounded organelle | 12 | MEIS2, TSPYL2, RAPSN, GLIS1, H2AFY, HNF4G, TRIM63, NOP10, KLHL3, RNF20, ZW10, FGD4 |
| GO:0043232~intracellular non-membrane-bounded organelle | 12 | MEIS2, TSPYL2, RAPSN, GLIS1, H2AFY, HNF4G, TRIM63, NOP10, KLHL3, RNF20, ZW10, FGD4 |
| GO:0045944~positive regulation of transcription from RNA polymerase II promoter | 3 | MEIS2, GLIS1, NR1H3 |
| GO:0010604~positive regulation of macromolecule metabolic process | 5 | MEIS2, GLIS1, RNF20, IL1A, NR1H3 |
| GO:0045935~positive regulation of nucleobase, nucleoside, nucleotide and nucleic acid metabolic process | 4 | MEIS2, GLIS1, RNF20, NR1H3 |
| GO:0051173~positive regulation of nitrogen compound metabolic process | 4 | MEIS2, GLIS1, RNF20, NR1H3 |
| GO:0031981~nuclear lumen | 7 | SNAI3, MEIS2, TSPYL2, GLIS1, HNF4G, NOP10, RNF20 |
| GO:0045893~positive regulation of transcription, DNA-dependent | 3 | MEIS2, GLIS1, NR1H3 |
| GO:0051254~positive regulation of RNA metabolic process | 3 | MEIS2, GLIS1, NR1H3 |
| GO:0070013~intracellular organelle lumen | 7 | SNAI3, MEIS2, TSPYL2, GLIS1, HNF4G, NOP10, RNF20 |
| GO:0043233~organelle lumen | 7 | SNAI3, MEIS2, TSPYL2, GLIS1, HNF4G, NOP10, RNF20 |
| GO:0031974~membrane-enclosed lumen | 7 | SNAI3, MEIS2, TSPYL2, GLIS1, HNF4G, NOP10, RNF20 |
| Enrichment Score: 0.465581027382082 | | |
| IPR001849:Pleckstrin homology | 3 | VEPH1, OSBPL9, FGD4 |
| IPR011993:Pleckstrin homology-type | 3 | VEPH1, OSBPL9, FGD4 |
| SM00233:PH | 3 | VEPH1, OSBPL9, FGD4 |
| Enrichment Score: 0.4066995149813719 | | |
| GO:0007610~behavior | 6 | CCL3, SLC1A3, CCL3L3, RAC1, ACSL4, MTNR1A |
| GO:0000267~cell fraction | 4 | CCL3, SLC1A3, RAC1, ACSL4 |
| GO:0005624~membrane fraction | 3 | SLC1A3, RAC1, ACSL4 |
| GO:0005626~insoluble fraction | 3 | SLC1A3, RAC1, ACSL4 |
| Enrichment Score: 0.3739835083948733 | | |
| GO:0016023~cytoplasmic membrane-bounded vesicle | 4 | RAB3C, CAPN11, TRPV2, RAC1 |
| GO:0031988~membrane-bounded vesicle | 4 | RAB3C, CAPN11, TRPV2, RAC1 |
| GO:0031410~cytoplasmic vesicle | 4 | RAB3C, CAPN11, TRPV2, RAC1 |
| GO:0031982~vesicle | 4 | RAB3C, CAPN11, TRPV2, RAC1 |
| Enrichment Score: 0.20190763005512594 | | |
| cell membrane | 12 | VEPH1, PCDHGA10, CNNM4, RAB3C, OR5K3, RAPSN, CLDN6, TRPV2, RAC1, MMP16, RHOD, MTNR1A |
| GO:0044459~plasma membrane part | 12 | VEPH1, SLC1A3, RAB3C, IL27RA, RAPSN, CLDN6, TRPV2, RAC1, MMP16, RHOD, SDC2, MTNR1A |
| GO:0005886~plasma membrane | 16 | PCDHGA10, CNNM4, RAB3C, IL27RA, OR5K3, CLDN6, TRPV2, MMP16, SDC2, VEPH1, SLC1A3, RAPSN, RAC1, RHOD, ACSL4, MTNR1A |
| topological domain:Extracellular | 10 | PCDHGA10, SLC1A3, IL27RA, OR5K3, CLDN6, TRPV2, GGT2, MMP16, SDC2, MTNR1A |
| membrane | 22 | PCDHGA10, CNNM4, RAB3C, IL27RA, OR5K3, CLDN6, TRPV2, ZDHHC7, GGT2, MMP16, SDC2, SVOPL, VEPH1, SLC1A3, RAPSN, RAC1, FAM162A, RHOD, ACSL4, MTNR1A, ZW10, DHCR24 |

TABLE 1-continued

Genes Positively Correlated with TB

| Term | Count | Genes |
| --- | --- | --- |
| GO:0005887~integral to plasma membrane | 5 | IL27RA, TRPV2, MMP16, SDC2, MTNR1A |
| glycoprotein | 15 | PCDHGA10, CNNM4, HAPLN3, IL27RA, OR5K3, CRTAC1, TRPV2, GGT2, MMP16, SERPINI1, SDC2, SLC1A3, COL11A1, IL1A, MTNR1A |
| GO:0031226~intrinsic to plasma membrane | 5 | IL27RA, TRPV2, MMP16, SDC2, MTNR1A |
| topological domaiCytoplasmic | 11 | PCDHGA10, SLC1A3, IL27RA, OR5K3, CLDN6, TRPV2, GGT2, MMP16, ACSL4, SDC2, MTNR1A |
| transmembrane region | 16 | PCDHGA10, CNNM4, IL27RA, OR5K3, CLDN6, TRPV2, ZDHHC7, GGT2, MMP16, SDC2, SVOPL, SLC1A3, FAM162A, ACSL4, DHCR24, MTNR1A |
| transmembrane | 16 | PCDHGA10, CNNM4, IL27RA, OR5K3, CLDN6, TRPV2, ZDHHC7, GGT2, MMP16, SDC2, SVOPL, SLC1A3, FAM162A, ACSL4, DHCR24, MTNR1A |
| glycosylation site:N-linked (GlcNAc . . .) | 11 | PCDHGA10, CNNM4, IL27RA, OR5K3, TRPV2, GGT2, MMP16, SERPINI1, COL11A1, IL1A, MTNR1A |
| GO:0016021~integral to membrane | 16 | PCDHGA10, CNNM4, IL27RA, OR5K3, CLDN6, TRPV2, ZDHHC7, GGT2, MMP16, SDC2, SVOPL, SLC1A3, FAM162A, ACSL4, DHCR24, MTNR1A |
| GO:0031224~intrinsic to membrane | 16 | PCDHGA10, CNNM4, IL27RA, OR5K3, CLDN6, TRPV2, ZDHHC7, GGT2, MMP16, SDC2, SVOPL, SLC1A3, FAM162A, ACSL4, DHCR24, MTNR1A |
| Enrichment Score: 0.1812991043816715 | | |
| Protease | 3 | CAPN11, UCHL5, MMP16 |
| GO:0070011~peptidase activity, acting on L-amino acid peptides | 3 | CAPN11, UCHL5, MMP16 |
| GO:0008233~peptidase activity | 3 | CAPN11, UCHL5, MMP16 |
| hydrolase | 5 | DUSP26, DUSP1, CAPN11, UCHL5, MMP16 |
| Enrichment Score: 0.03908551349344777 | | |
| GO:0017076~purine nucleotide binding | 7 | RAB3C, RAC1, ZNF12, RHOD, ACSL4, RRAGD, DHCR24 |
| GO:0000166~nucleotide binding | 8 | RAB3C, APLF, RAC1, ZNF12, RHOD, ACSL4, RRAGD, DHCR24 |
| GO:0030554~adenyl nucleotide binding | 3 | ZNF12, ACSL4, DHCR24 |
| GO:0001883~purine nucleoside binding | 3 | ZNF12, ACSL4, DHCR24 |
| GO:0001882~nucleoside binding | 3 | ZNF12, ACSL4, DHCR24 |

TABLE 2

Genes Negatively Correlated with TB

| Term | Count | Genes |
| --- | --- | --- |
| Enrichment Score: 1.2865881937081116 | | |
| golgi apparatus | 7 | PGAP3, DPY30, PNPLA8, ARHGEF2, SCYL1, SVIP, RTN3 |
| endoplasmic reticulum | 7 | PGAP3, PNPLA8, ELOVL3, UBE2V1P2, LMF1, SVIP, RTN3 |
| GO:0005794~Golgi apparatus | 7 | PGAP3, PNPLA8, ARHGEF2, SCYL1, SNX17, SVIP, RTN3 |
| GO:0005783~endoplasmic reticulum | 7 | PGAP3, PNPLA8, ELOVL3, UBE2V1P2, LMF1, SVIP, RTN3 |
| Enrichment Score: 1.193461933188953 | | |
| cytoskeleton | 7 | ARHGEF2, SCYL1, DLGAP5, PPL, DMD, AKAP12, CDC42SE1 |
| GO:0043228~non-membrane-bounded organelle | 14 | TUBBP5, ARHGEF2, SCYL1, DLGAP5, PPL, DMD, AKAP12, CDC42SE1, TUBB8, MRPL45, CYB561, RPA4, TOP3B, RTN3 |

TABLE 2-continued

| Genes Negatively Correlated with TB | | |
|---|---|---|
| Term | Count | Genes |
| GO:0043232~intracellular non-membrane-bounded organelle | 14 | TUBBP5, ARHGEF2, SCYL1, DLGAP5, PPL, DMD, AKAP12, CDC42SE1, TUBB8, MRPL45, CYB561, RPA4, TOP3B, RTN3 |
| GO:0005856~cytoskeleton | 9 | TUBBP5, ARHGEF2, SCYL1, DLGAP5, PPL, DMD, AKAP12, CDC42SE1, TUBB8 |
| Enrichment Score: 1.1139583061715095 | | |
| GO:0065003~macromolecular complex assembly | 7 | SNAPC5, TUBBP5, BCS1L, TUBB8, GTF2B, NAP1L4, GCHFR |
| GO:0006461~protein complex assembly | 6 | SNAPC5, TUBBP5, BCS1L, TUBB8, GTF2B, GCHFR |
| GO:0070271~protein complex biogenesis | 6 | SNAPC5, TUBBP5, BCS1L, TUBB8, GTF2B, GCHFR |
| GO:0043933~macromolecular complex subunit organization | 7 | SNAPC5, TUBBP5, BCS1L, TUBB8, GTF2B, NAP1L4, GCHFR |
| GO:0034622~cellular macromolecular complex assembly | 4 | TUBBP5, BCS1L, TUBB8, NAP1L4 |
| GO:0043623~cellular protein complex assembly | 3 | TUBBP5, BCS1L, TUBB8 |
| GO:0034621~cellular macromolecular complex subunit organization | 4 | TUBBP5, BCS1L, TUBB8, NAP1L4 |
| Enrichment Score: 0.9686068589505084 | | |
| GO:0006886~intracellular protein transport | 5 | ARHGEF2, SNX17, MGEA5, AKAP12, MRPL45 |
| GO:0034613~cellular protein localization | 5 | ARHGEF2, SNX17, MGEA5, AKAP12, MRPL45 |
| GO:0070727~cellular macromolecule localization | 5 | ARHGEF2, SNX17, MGEA5, AKAP12, MRPL45 |
| GO:0046907~intracellular transport | 6 | ARHGEF2, SCYL1, SNX17, MGEA5, AKAP12, MRPL45 |
| GO:0008104~protein localization | 7 | ARHGEF2, SNX17, DMD, LMF1, MGEA5, AKAP12, MRPL45 |
| GO:0015031~protein transport | 6 | ARHGEF2, SNX17, LMF1, MGEA5, AKAP12, MRPL45 |
| GO:0045184~establishment of protein localization | 6 | ARHGEF2, SNX17, LMF1, MGEA5, AKAP12, MRPL45 |
| Enrichment Score: 0.7602205187662866 | | |
| GO:0005856~cytoskeleton | 9 | TUBBP5, ARHGEF2, SCYL1, DLGAP5, PPL, DMD, AKAP12, CDC42SE1, TUBB8 |
| GO:0015630~micro tubule cytoskeleton | 5 | TUBBP5, ARHGEF2, SCYL1, DLGAP5, TUBB8 |
| GO:0005874~microtubule | 3 | TUBBP5, ARHGEF2, TUBB8 |
| GO:0044430~cytoskeletal part | 5 | TUBBP5, ARHGEF2, SCYL1, DLGAP5, TUBB8 |
| Enrichment Score: 0.6295977322358206 | | |
| GO:0005525~GTP binding | 5 | TUBBP5, RABL3, RAB28, TUBB8, PCK2 |
| GO:0032561~guanyl ribonucleotide binding | 5 | TUBBP5, RABL3, RAB28, TUBB8, PCK2 |
| GO:0019001~guanyl nucleotide binding | 5 | TUBBP5, RABL3, RAB28, TUBB8, PCK2 |
| nucleotide phosphate-binding region:GTP | 4 | RABL3, RAB28, TUBB8, PCK2 |
| gtp-binding | 4 | RABL3, RAB28, TUBB8, PCK2 |
| GO:0032553~ribonucleotide binding | 11 | TUBBP5, PNPLA8, RABL3, SCYL1, RAB28, HSPA14, BCS1L, TUBB8, PCK2, CDKL2, TOP3B |
| GO:0032555~purine ribonucleotide binding | 11 | TUBBP5, PNPLA8, RABL3, SCYL1, RAB28, HSPA14, BCS1L, TUBB8, PCK2, CDKL2, TOP3B |
| GO:0017076~purine nucleotide binding | 11 | TUBBP5, PNPLA8, RABL3, SCYL1, RAB28, HSPA14, BCS1L, TUBB8, PCK2, CDKL2, TOP3B |
| GO:0003924~GTPase activity | 3 | TUBBP5, RAB28, TUBB8 |
| GO:0000166~nucleotide binding | 12 | HNRNPL, TUBBP5, PNPLA8, RABL3, SCYL1, RAB28, HSPA14, BCS1L, TUBB8, PCK2, CDKL2, TOP3B |
| nucleotide-binding | 8 | RABL3, RAB28, HSPA14, BCS1L, TUBB8, PCK2, CDKL2, TOP3B |
| GO:0005524~ATP binding | 6 | PNPLA8, SCYL1, HSPA14, BCS1L, CDKL2, TOP3B |

TABLE 2-continued

Genes Negatively Correlated with TB

| Term | Count | Genes |
|---|---|---|
| GO:0032559~adenyl ribonucleotide binding | 6 | PNPLA8, SCYL1, HSPA14, BCS1L, CDKL2, TOP3B |
| GO:0030554~adenyl nucleotide binding | 6 | PNPLA8, SCYL1, HSPA14, BCS1L, CDKL2, TOP3B |
| GO:0001883~purine nucleoside binding | 6 | PNPLA8, SCYL1, HSPA14, BCS1L, CDKL2, TOP3B |
| GO:0001882~nucleoside binding | 6 | PNPLA8, SCYL1, HSPA14, BCS1L, CDKL2, TOP3B |
| atp-binding | 4 | HSPA14, BCS1L, CDKL2, TOP3B |
| Enrichment Score: 0.4766169112180347 | | |
| GO:0031090~organelle membrane | 7 | IMMP1L, PGAP3, PNPLA8, SCYL1, BCS1L, MRPL45, GCHFR |
| GO:0005743~mitochondrial inner membrane | 3 | IMMP1L, BCS1L, MRPL45 |
| GO:0005739~mitochondrion | 6 | IMMP1L, SIVA1, PPL, BCS1L, PCK2, MRPL45 |
| GO:0019866~organelle inner membrane | 3 | IMMP1L, BCS1L, MRPL45 |
| GO:0031967~organelle envelope | 4 | IMMP1L, BCS1L, MRPL45, GCHFR |
| GO:0031975~envelope | 4 | IMMP1L, BCS1L, MRPL45, GCHFR |
| mitochondrion | 5 | IMMP1L, PPL, BCS1L, PCK2, MRPL45 |
| GO:0031966~mitochondrial membrane | 3 | IMMP1L, BCS1L, MRPL45 |
| GO:0005740~mitochondrial envelope | 3 | IMMP1L, BCS1L, MRPL45 |
| GO:0044429~mitochondrial part | 3 | IMMP1L, BCS1L, MRPL45 |
| Enrichment Score: 0.4269912862695477 | | |
| GO:0008219~cell death | 5 | SIVA1, ARHGEF2, PDCD10, MGEA5, RTN3 |
| GO:0016265~death | 5 | SIVA1, ARHGEF2, PDCD10, MGEA5, RTN3 |
| Apoptosis | 3 | SIVA1, PDCD10, RTN3 |
| GO:0006915~apoptosis | 4 | SIVA1, ARHGEF2, PDCD10, RTN3 |
| GO:0012501~programmed cell death | 4 | SIVA1, ARHGEF2, PDCD10, RTN3 |
| Enrichment Score: 0.3835607614553488 | | |
| GO:0043065~positive regulation of apoptosis | 4 | SIVA1, ARHGEF2, SSTR3, RARB |
| GO:0043068~positive regulation of programmed cell death | 4 | SIVA1, ARHGEF2, SSTR3, RARB |
| GO:0010942~positive regulation of cell death | 4 | SIVA1, ARHGEF2, SSTR3, RARB |
| GO:0006917~induction of apoptosis | 3 | SIVA1, ARHGEF2, SSTR3 |
| GO:0012502~induction of programmed cell death | 3 | SIVA1, ARHGEF2, SSTR3 |
| GO:0042981~regulation of apoptosis | 4 | SIVA1, ARHGEF2, SSTR3, RARB |
| GO:0043067~regulation of programmed cell death | 4 | SIVA1, ARHGEF2, SSTR3, RARB |
| GO:0010941~regulation of cell death | 4 | SIVA1, ARHGEF2, SSTR3, RARB |
| GO:0042127~regulation of cell proliferation | 3 | ARHGEF2, SSTR3, RARB |
| Enrichment Score: 0.2971377682178453 | | |
| GO:0046914~transition metal ion binding | 14 | SIVA1, ZNF831, ARHGEF2, ZNF92, PCK2, RNF181, CYB561, GTF2B, FAM90A24P, APOBEC3A, DMD, ZNF426, RARB, CP |
| GO:0008270~zinc ion binding | 11 | SIVA1, ZNF831, APOBEC3A, ARHGEF2, ZNF92, DMD, ZNF426, RARB, RNF181, GTF2B, FAM90A24P |
| metal-binding | 13 | SIVA1, ZNF831, ARHGEF2, ZNF92, PCK2, RNF181, CYB561, GTF2B, APOBEC3A, DMD, ZNF426, RARB, CP |
| zinc | 10 | SIVA1, ZNF831, APOBEC3A, ARHGEF2, ZNF92, DMD, ZNF426, RARB, RNF181, GTF2B |
| zinc-finger | 8 | ZNF831, ARHGEF2, ZNF92, DMD, ZNF426, RARB, RNF181, GTF2B |

TABLE 2-continued

Genes Negatively Correlated with TB

| Term | Count | Genes |
|---|---|---|
| GO:0046872~metal ion binding | 14 | SIVA1, ZNF831, ARHGEF2, ZNF92, PCK2, RNF181, CYB561, GTF2B, FAM90A24P, APOBEC3A, DMD, ZNF426, RARB, CP |
| GO:0043169~cation binding | 14 | SIVA1, ZNF831, ARHGEF2, ZNF92, PCK2, RNF181, CYB561, GTF2B, FAM90A24P, APOBEC3A, DMD, ZNF426, RARB, CP |
| GO:0043167~ion binding | 14 | SIVA1, ZNF831, ARHGEF2, ZNF92, PCK2, RNF181, CYB561, GTF2B, FAM90A24P, APOBEC3A, DMD, ZNF426, RARB, CP |
| Enrichment Score: 0.2186893313759546 | | |
| G protein-coupled receptor | 3 | MCHR2, SSTR3, OPN1LW |
| PIRSF800006:rhodopsin-like G protein-coupled receptors | 4 | MCHR2, OR51I2, SSTR3, OPN1LW |
| GO:0007186~G-protein coupled receptor protein signaling pathway | 6 | MCHR2, OR51I2, SSTR3, OR2B3, OPN1LW, AKAP12 |
| IPR017452:GPCR, rhodopsin-like superfamily | 4 | MCHR2, OR51I2, SSTR3, OPN1LW |
| IPR000276:7TM GPCR, rhodopsin-like | 4 | MCHR2, OR51I2, SSTR3, OPN1LW |
| GO:0050877~neurological system process | 6 | OR51I2, OR2B3, OPN1LW, DMD, IL1RAPL1, GCHFR |
| receptor | 7 | MCHR2, OR51I2, SSTR3, OPN1LW, PLXNB2, RARB, IL1RAPL1 |
| g-protein coupled receptor | 4 | MCHR2, OR51I2, SSTR3, OPN1LW |
| GO:0031224~intrinsic to membrane | 19 | PGAP3, MCHR2, OR2B3, OPN1LW, PLXNB2, LMF1, CDC42SE1, BCS1L, CYB561, RTN3, PNPLA8, SSTR3, OR51I2, SLC26A7, ELOVL3, UBE2V1P2, DNAJC4, CP, IL1RAPL1 |
| transducer | 4 | MCHR2, OR51I2, SSTR3, OPN1LW |
| membrane | 23 | PGAP3, MCHR2, OPN1LW, PLXNB2, LMF1, CDC42SE1, BCS1L, CYB561, RTN3, IMMP1L, PNPLA8, SSTR3, OR51I2, RAB28, SLC26A7, PPL, ELOVL3, DMD, UBE2V1P2, SVIP, DNAJC4, IL1RAPL1, GCHFR |
| transmembrane protein | 3 | MCHR2, SSTR3, OPN1LW |
| GO:0050890~cognition | 4 | OR51I2, OR2B3, OPN1LW, IL1RAPL1 |
| GO:0016021~integral to membrane | 17 | PGAP3, MCHR2, OR2B3, OPN1LW, PLXNB2, LMF1, BCS1L, CYB561, RTN3, PNPLA8, SSTR3, OR51I2, SLC26A7, ELOVL3, UBE2V1P2, DNAJC4, IL1RAPL1 |
| GO:0007600~sensory perception | 3 | OR51I2, OR2B3, OPN1LW |
| transmembrane region | 16 | PGAP3, MCHR2, OPN1LW, PLXNB2, LMF1, BCS1L, CYB561, RTN3, PNPLA8, SSTR3, OR51I2, SLC26A7, ELOVL3, UBE2V1P2, DNAJC4, IL1RAPL1 |
| transmembrane | 16 | PGAP3, MCHR2, OPN1LW, PLXNB2, LMF1, BCS1L, CYB561, RTN3, PNPLA8, SSTR3, OR51I2, SLC26A7, ELOVL3, UBE2V1P2, DNAJC4, IL1RAPL1 |
| GO:0007166~cell surface receptor linked signal transduction | 6 | MCHR2, OR51I2, SSTR3, OR2B3, OPN1LW, AKAP12 |
| topological domain:Cytoplasmic | 9 | PGAP3, MCHR2, OR51I2, SSTR3, OPN1LW, SLC26A7, PLXNB2, CYB561, IL1RAPL1 |
| topological domain:Extracellular | 7 | MCHR2, OR51I2, SSTR3, OPN1LW, SLC26A7, PLXNB2, IL1RAPL1 |
| glycosylation site:N-linked (GlcNAc . . .) | 9 | PGAP3, PNPLA8, MCHR2, OR51I2, SSTR3, OPN1LW, PLXNB2, CP, IL1RAPL1 |
| glycoprotein | 9 | PGAP3, PNPLA8, MCHR2, OR51I2, SSTR3, OPN1LW, PLXNB2, CP, IL1RAPL1 |
| Enrichment Score: 0.1710474073325014 | | |
| zinc-finger | 8 | ZNF831, ARHGEF2, ZNF92, DMD, ZNF426, RARB, RNF181, GTF2B |
| IPR013087:Zinc finger, C2H2-type/integrase, DNA-binding | 3 | ZNF831, ZNF92, ZNF426 |

TABLE 2-continued

Genes Negatively Correlated with TB

| Term | Count | Genes |
|---|---|---|
| SM00355:ZnF C2H2 | 3 | ZNF831, ZNF92, ZNF426 |
| IPR007087:Zinc finger, C2H2-type | 3 | ZNF831, ZNF92, ZNF426 |
| IPR015880:Zinc finger, C2H2-like | 3 | ZNF831, ZNF92, ZNF426 |
| Enrichment Score: 0.16076605592743434 | | |
| SM00349:KRAB | 3 | ZNF92, SSX6, ZNF426 |
| IPR001909:Krueppel-associated box | 3 | ZNF92, SSX6, ZNF426 |
| transcription regulation | 8 | SNAPC5, DPY30, SCYL1, ZNF92, SSX6, ZNF426, RARB, GTF2B |
| Transcription | 8 | SNAPC5, DPY30, SCYL1, ZNF92, SSX6, ZNF426, RARB, GTF2B |
| GO:0045449~regulation of transcription | 10 | SIVA1, SNAPC5, SCYL1, ZNF92, DMD, UBE2V1P2, SSX6, ZNF426, RARB, GTF2B |
| GO:0003677~DNA binding | 8 | SNAPC5, SCYL1, ZNF92, ZNF426, RARB, GTF2B, RPA4, TOP3B |
| GO:0030528~transcription regulator activity | 5 | SNAPC5, ZNF92, UBE2V1P2, RARB, GTF2B |
| GO:0006355~regulation of transcription, DNA-dependent | 6 | ZNF92, UBE2V1P2, SSX6, ZNF426, RARB, GTF2B |
| GO:0006350~transcription | 7 | SNAPC5, SCYL1, ZNF92, SSX6, ZNF426, RARB, GTF2B |
| GO:0051252~regulation of RNA metabolic process | 6 | ZNF92, UBE2V1P2, SSX6, ZNF426, RARB, GTF2B |
| GO:0003700~transcription factor activity | 3 | SNAPC5, ZNF92, RARB |
| dna-binding | 5 | SCYL1, ZNF92, ZNF426, RARB, TOP3B |
| Enrichment Score: 0.1572294185208537 | | |
| host-virus interaction | 3 | SIVA1, GTF2B, RTN3 |
| GO:0031981~nuclear lumen | 5 | HNRNPL, SIVA1, GTF2B, CYB561, RTN3 |
| GO:0005654~nucleoplasm | 3 | HNRNPL, SIVA1, GTF2B |
| GO:0070013~intracellular organelle lumen | 5 | HNRNPL, SIVA1, GTF2B, CYB561, RTN3 |
| GO:0043233~organelle lumen | 5 | HNRNPL, SIVA1, GTF2B, CYB561, RTN3 |
| GO:0031974~membrane-enclosed lumen | 5 | HNRNPL, SIVA1, GTF2B, CYB561, RTN3 |
| Enrichment Score: 0.12193299079639833 | | |
| GO:0000267~cell fraction | 4 | PNPLA8, DMD, DNAJC4, GCHFR |
| GO:0005624~membrane fraction | 3 | PNPLA8, DMD, DNAJC4 |
| GO:0005626~insoluble fraction | 3 | PNPLA8, DMD, DNAJC4 |
| Enrichment Score: 0.031540863257107116 | | |
| disulfide bond | 9 | AADACL2, OR51I2, RNASE11, SSTR3, OPN1LW, MGEA5, CP, IGKC, IL1RAPL1 |
| disulfide bond | 9 | AADACL2, OR51I2, RNASE11, SSTR3, OPN1LW, MGEA5, CP, IGKC, IL1RAPL1 |
| GO:0005576~extracellular region | 5 | AADACL2, RNASE11, CP, IGKC, RTN3 |
| signal | 7 | AADACL2, PGAP3, RNASE11, PLXNB2, CP, IGKC, IL1RAPL1 |
| signal peptide | 7 | AADACL2, PGAP3, RNASE11, PLXNB2, CP, IGKC, IL1RAPL1 |
| Secreted | 3 | AADACL2, RNASE11, CP |

Example 2. A Comprehensive Single Cell Atlas of Non-Human Primate Cell During Homeostasis and Pathogenic Infection Immune systems play an essential role in ensuring our health. From decades of laboratory and clinical work, there has been a basic understanding of immune balance and its importance for a healthy immune system. For example, hyperactivity can lead to allergy, inflammation, tissue damage, autoimmune disease and excessive cellular death. On the other hand, immunodeficiency can lead to outgrowth of cancers and the inability to kill or suppress external invaders. The immune system has evolved multiple modalities and redundancies that balance the system, including but not limited to memory, exhaustion, anergy, and senescence.

As the gene-expression program of a given cell closely reflects both its identity and function (Heinz et al., 2015), a systematic atlas of single-cell RNA profiles can help address many questions about immune regulations, their networks and molecular processes, and the response to pathogenic stimuli. Given the importance of the immune system, a systematic understanding of immune regulations on cell, tissue, and organism levels is crucial for clinicians and researchers to efficiently diagnose and develop treatments for immune system related disease.

Here, using scRNA-seq, this study identified gene signatures involved in SHIV-infection and immune responses, characterized cellular heterogeneity within specific cell-types, and demonstrated how these cell types and states change dynamically at different states of infection. More importantly, this study provides a resourceful pan-tissue database of expression profiles of healthy non-human primate that serves as a detailed reference data set for follow up studies regarding HIV as well as more disease and pathogenic states. Given the resemblance between HIV and SHIV, and the kinship between human and non-human primates, the atlas disclosed by this study also allows for parallel comparison and identifications of specific sub cell types as well as differentially regulated genes involved in human HIV infection.

Four Rhesus Macaques were sacrificed with full necropsy. Single cells from 12 distinct tissues were collected and single cell RNA-Sequencing was performed on these cells. Three Rhesus Macaques were infected with SHIV for 6 months, initiated anti-retroviral therapy for 6 months, and then sacrificed with full necropsy. Eight distinct tissue per SHIV+ animal was collected for single cell RNA-Sequencing. Tissues were collected as population controls in multiple forms, including RNALater, paraffin embedded, live cells frozen, lysed post dissociation and saved for control experiments and validations.

Figure 6:
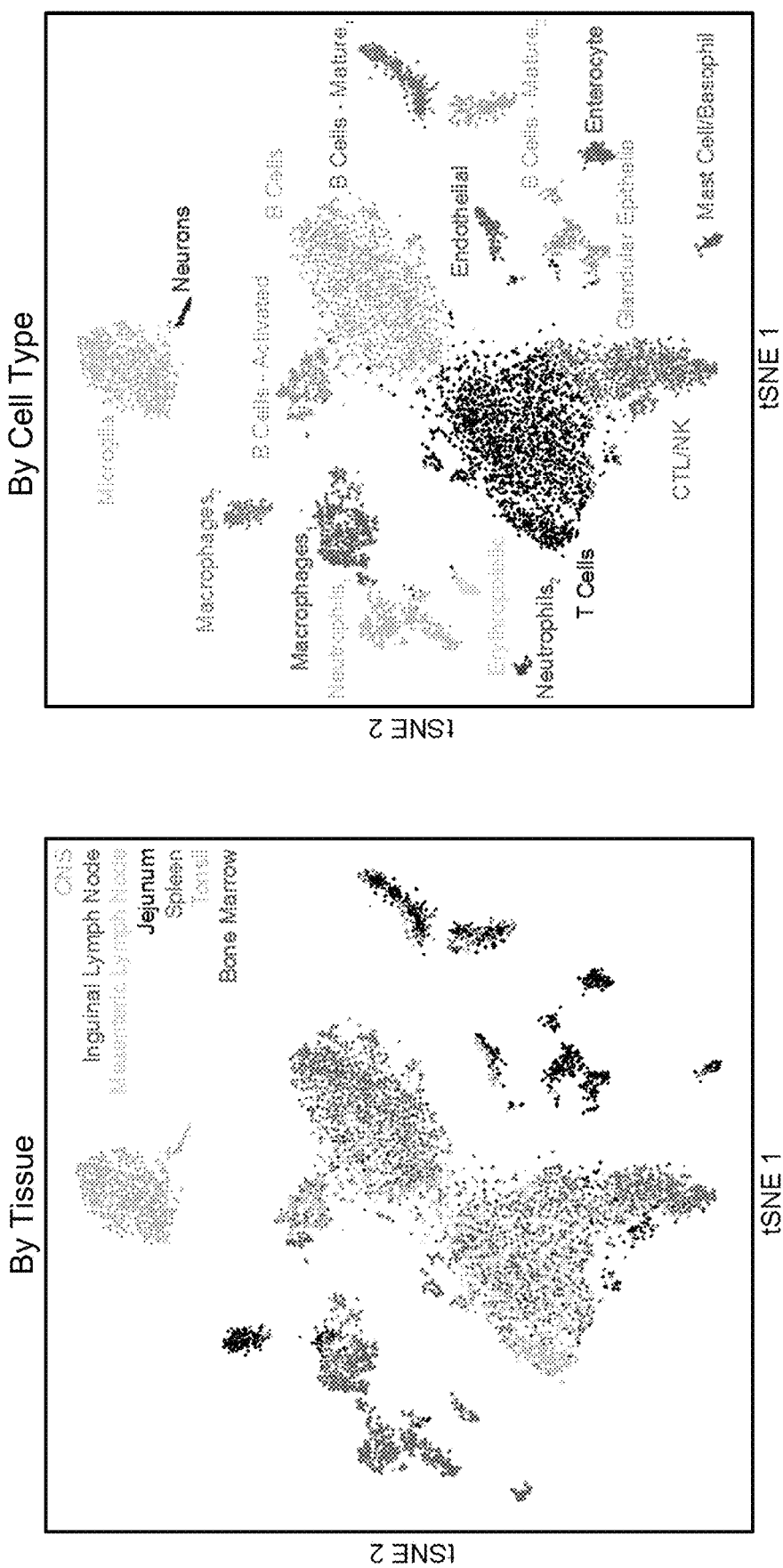
FIG. 6—includes t-distributed stochastic neighbor embedding (t-SNE) plots of single cell profiles defining cells by tissue (left) and cell type (right).
Figure 7:
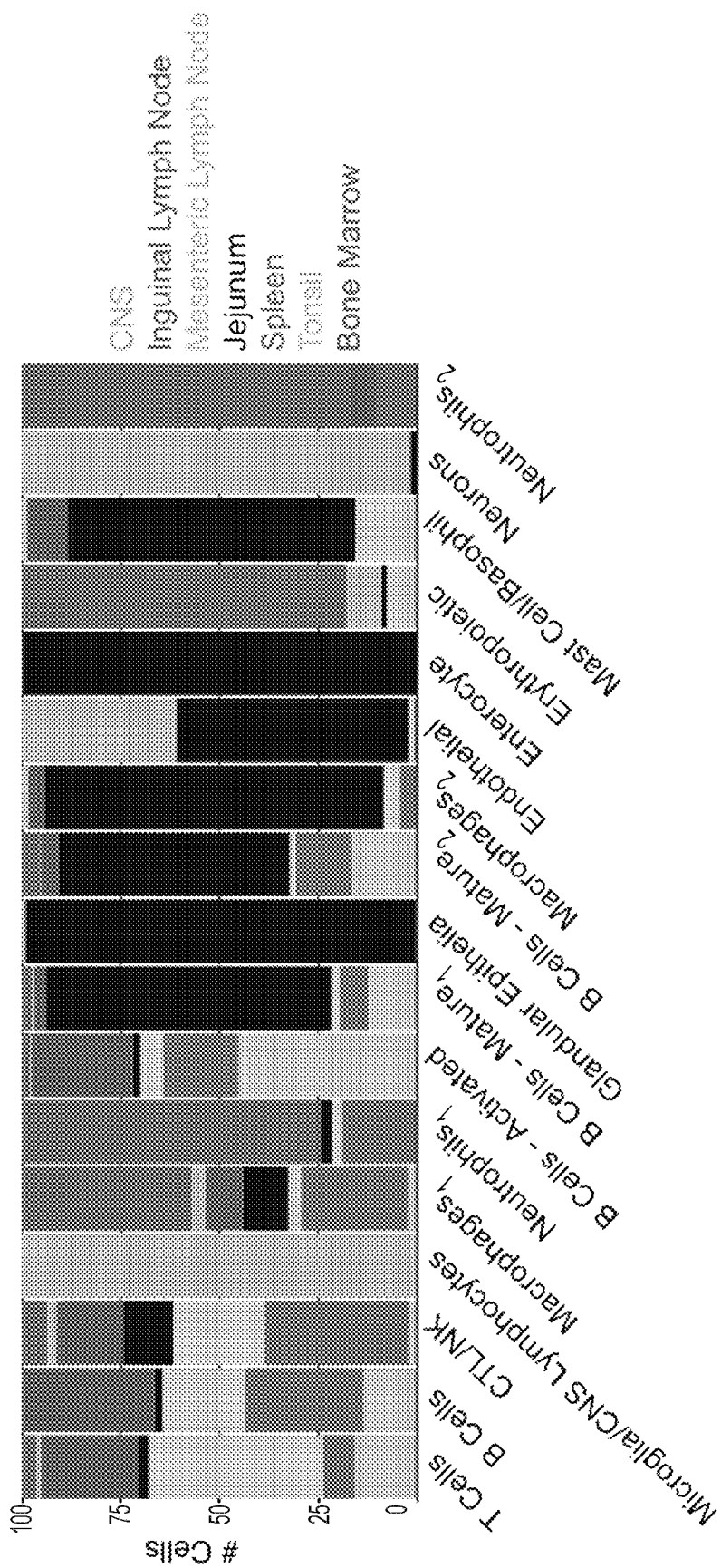
FIG. 7—Single cell transcriptome expression profiles cluster by cell type.

Single cell sequencing data was partitioned and annotated with supervised clustering, the results of which were visualized using tSNE (Amir el et al., 2013; Shekhar et al., 2016; van der Maaten and Hinton, 2008a). Based on expression profiles, individual cells are clustered and defined by tissues and cell types (FIG. 6-7). Particularly, this study identifies tissue specific phenotypes and behaviors of T cells (CD3E+, CD3D+, and CD3G+ cells), neutrophils, microglia, B cells, glandular epithelia, enterocytes, fibroblasts, megakaryocytes, erythroid precursor, DC, NK, macrophages, pneumocytes, eosinophil, and basophil cells are differentiated by expression profiles in axillary lymph nodes, central nerve system, colon, ileum, liver, lung, mesenteric lymph nodes, blood, spleen, thymus, and tonsil tissues, as illustrated in FIGS. 8-18. Specifically, in macrophages from different tissues, gene expression (S100A8, HBB, MNP1A, CAMP, LOC710097, gene 24745, gene 18845, LOC703853, LOC706282, RTD1B, LOC106994075, PLACE, CLEC9A, GZMB, IRF8, FCER1A, KNG1, IGFBP6, CCDC50, NCOA7, C1QB, SEPP1, FABP4, C1QC, GPNMB, APOE, ACP5, YMRM176B, ADAMDEC1, CCDC 152, S100A6, FCGR3, VCAN, FGR, LILRB1, FCN1, AHNAK, FN1, C5AR1, TIMP1) distinguishes individual cells by their tissue of origins (FIG. 10).

Figure 19A:
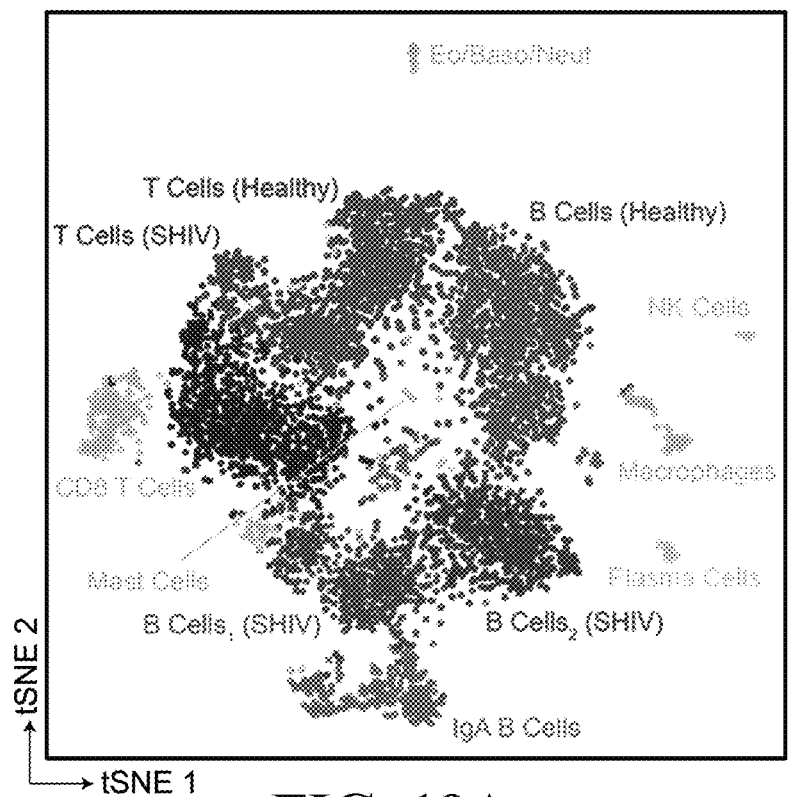
FIG. 19A-19C—Single cell genomics FIG. 19A Single cell genomics of cells from lymphoid tissue from healthy and SHIV-infected Rhesus macaques defines specific cell subsets in t-SNE plots.
Figure 19B:
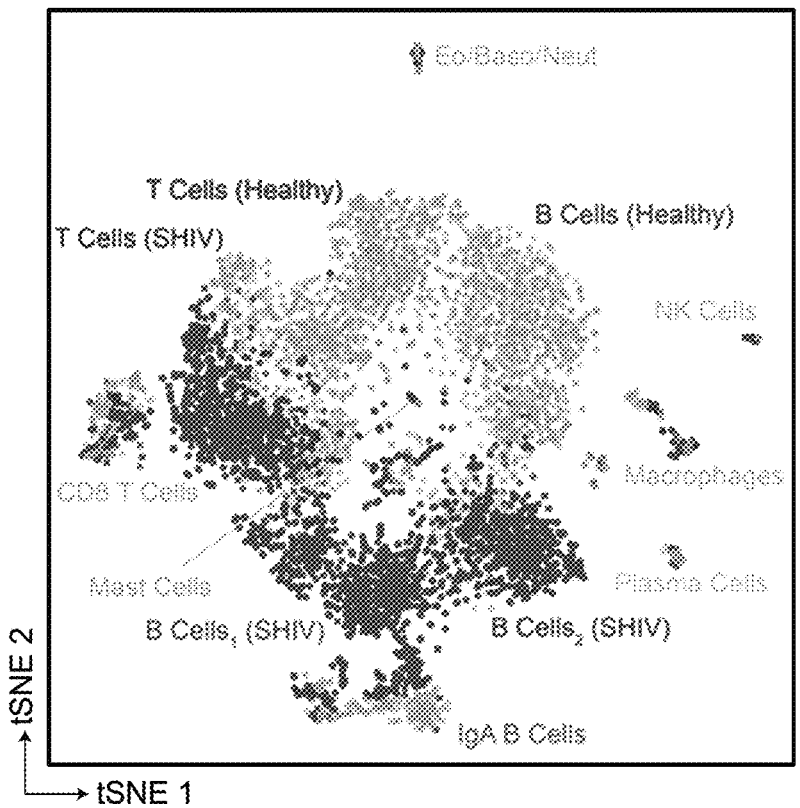
Figure 19C:
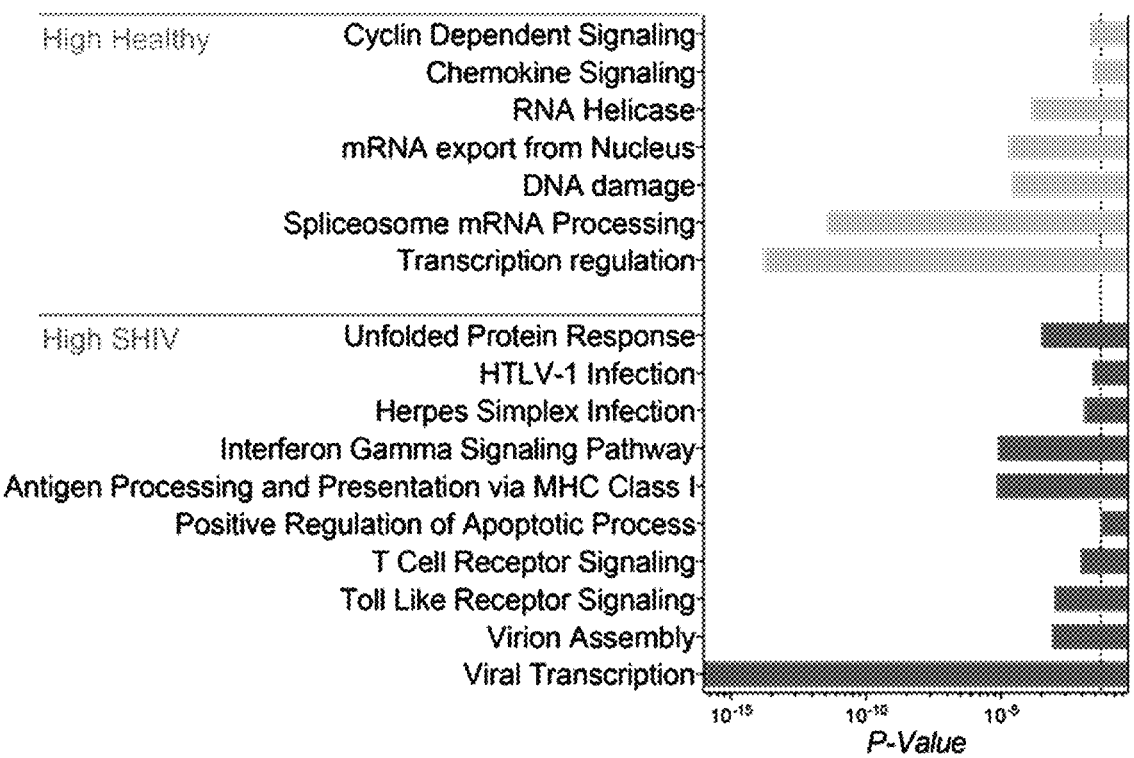
Figure 20:
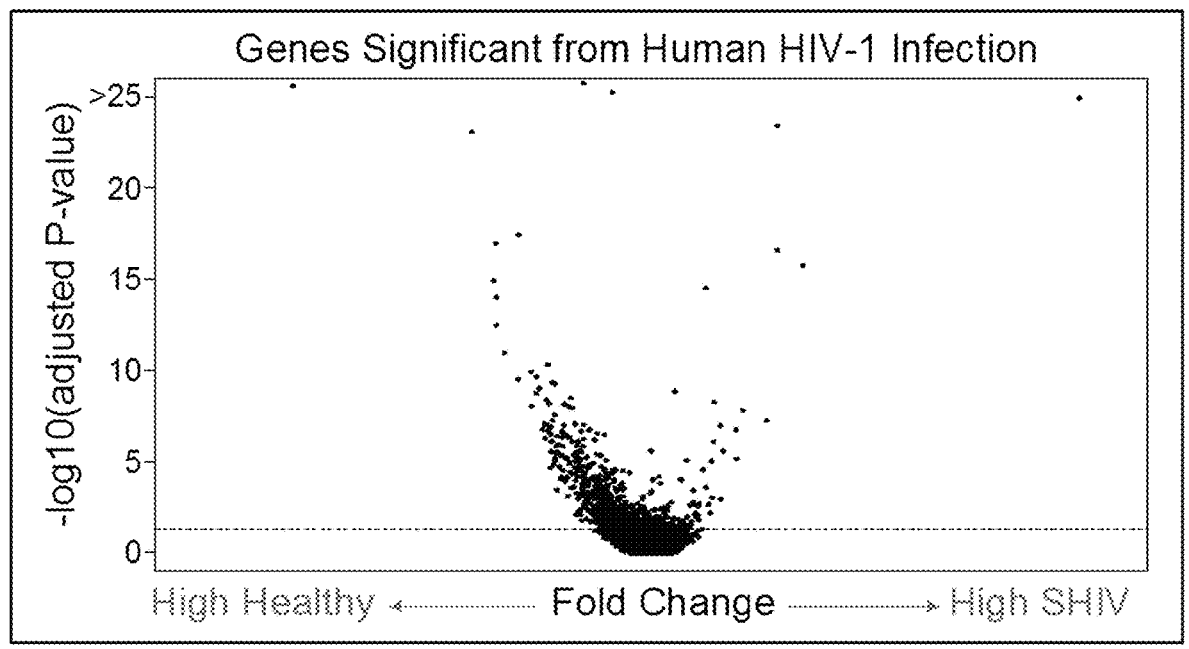
FIG. 20—Comparison of differentially expressed genes between HIV$^+$ and HIV$^-$ T cells in human lymph nodes with SHIV$^+$ and SHIV$^-$ T cells in non-human primates shows significant overlap.
Figure 21A:
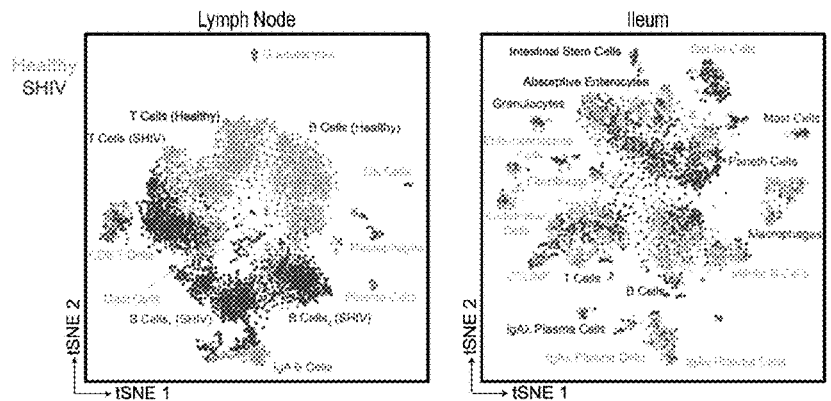
FIG. 21A-21D Impact of chronic SHIV infection on different tissue niches visualized in t-SNE plots.
Figure 21B:
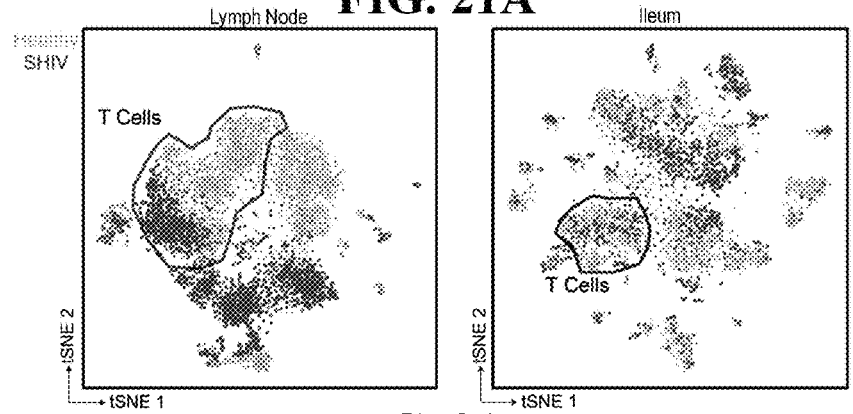
Figure 21C:
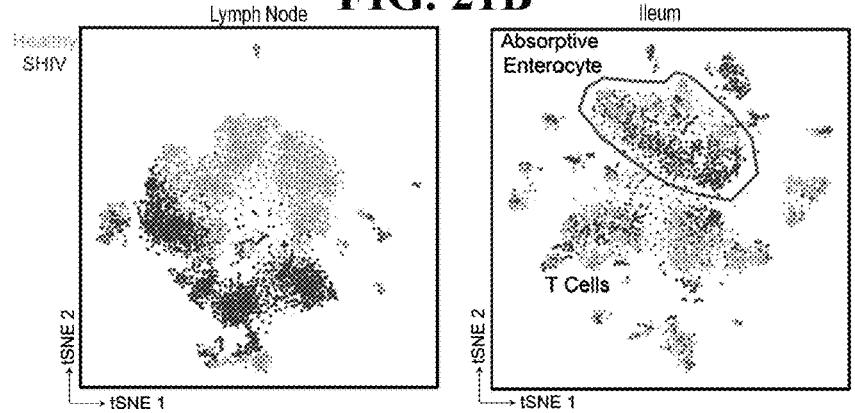
Figure 21D:
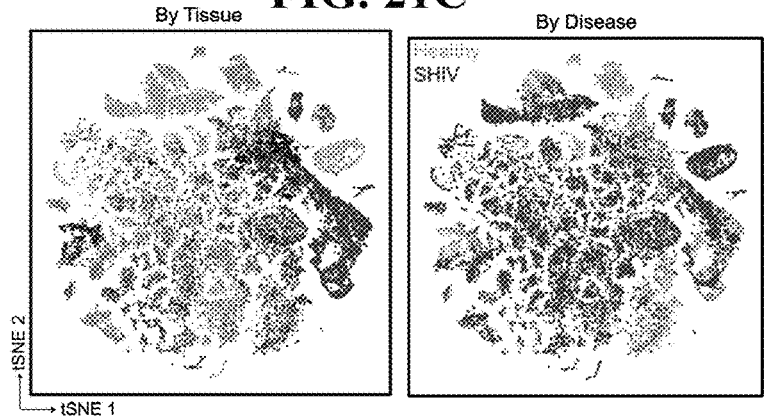

By comparing single cell profiles of healthy subjects with SHIV infected ones, this study identified subsets of cells in specific tissues differentially respond to SHIV infection (FIGS. 19A and 19B). In lymphoid tissue, certain immune cells such as CD8 T cells and macrophages appear to be equally represented in both healthy and SHIV infected cells, while other cells such as CD4 T cells and B cells show marked difference between the two states. The comparison further identifies pathways and genes that are differentially expressed in healthy and SHIV infected cells. In CD4 T cells, genes involved in cyclin dependent signaling, chemokine signaling, RNA helicase, mRNA export from nucleus, DNA damage, spliceosome mRNA processing, and transcription regulation are identified as correlated with healthy cells, and genes involved in unfolded protein response, HTLV-1 infection, herpes simplex infection, interferon gamma signaling pathway, antigen processing and presentation via MHC class I, positive regulation of apoptotic process, T cell receptor signaling, virion assembly, and vial transcription are associated with HIV infection (FIGS. 19C and 19D). More comprehensively, this study identified gene markers that are differentially expressed in SHIV infected cells. This study also validated the close relationship between SHIV and HIV infection in non-human primate and human cells, by comparing differentially expressed genes between HIV infected and healthy human lymph node cells with SHIV infected and healthy T cells in non-human primates. The significant overlap of the two sets of differentially expressed genes (FIG. 20) confirm that biomarkers identified in this study can further be used in diagnosis, monitoring, and treatment of human HIV related disease.

Example 3. Amplified Inflammatory Transcriptional Response to Infection by *Mycobacterium tuberculosis* Aggregates

*Mycobacterium tuberculosis* (Mtb) infection has the ability to tip from latency to active replication and cause pulmonary damage. The factors that cause the latency to active replication to occur is investigated here. While growth of MTB in live macrophages is generally well controlled, phagocytosis of clumps or aggregates of MTB results in the death of the macrophage. The dead macrophage acts as bait for the next macrophage, resulting in the serial killing of host cells. The differential regulation of macrophage genes as a function of the number and aggregation state of MTB using RNA-Seq is investigated.

CD14+ macrophages were isolated from healthy donor blood and differentiated into monocyte derived macrophages (MDMs) for 1 week using GM-CSF. MTB strain H37Rv, constitutively expressing mCherry, was cultured in parallel in a tween positive and tween negative culture for 1 week so that the bacteria were mid log phase when used to infect the MDMs.

Figure 22:
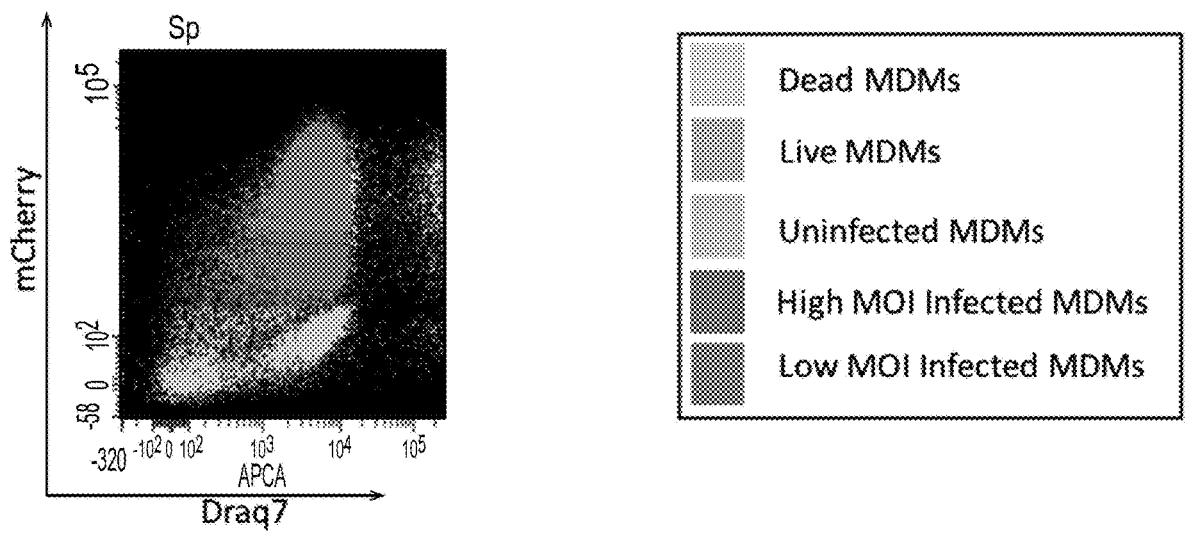
FIG. 22 Sorting of infected macrophages based on mCherry fluorescence (y-axis) allowed partitioning of MDMs into uninfected (cyan), low MOI (magenta) and high MOI (orange) of Mtb. Staining of MDMs with Draq7 (x-axis) allowed for separation of live cells (olive green) from any dead cells (lime green), enhancing cell viability for downstream RNA sequencing.

Macrophages were infected with MTB in the form of single bacilli or aggregated bacteria at an MOI decided by the OD600 of the tween positive bacteria. Infection lasted for 3 hours followed by a 3 hour incubation, to allow for the accumulation of transcripts Following incubation, MDMs were lifted from culture and stained with a live/dead stain. Live MDMs were sorted into Trizol, as shown by the gating strategy in FIG. 22, into uninfected, singles low (SL), singles high (SH), and aggregates (A). Population RNA was extracted and the cells were sequenced using the Smart-seq 2 protocol.

Figure 23A:
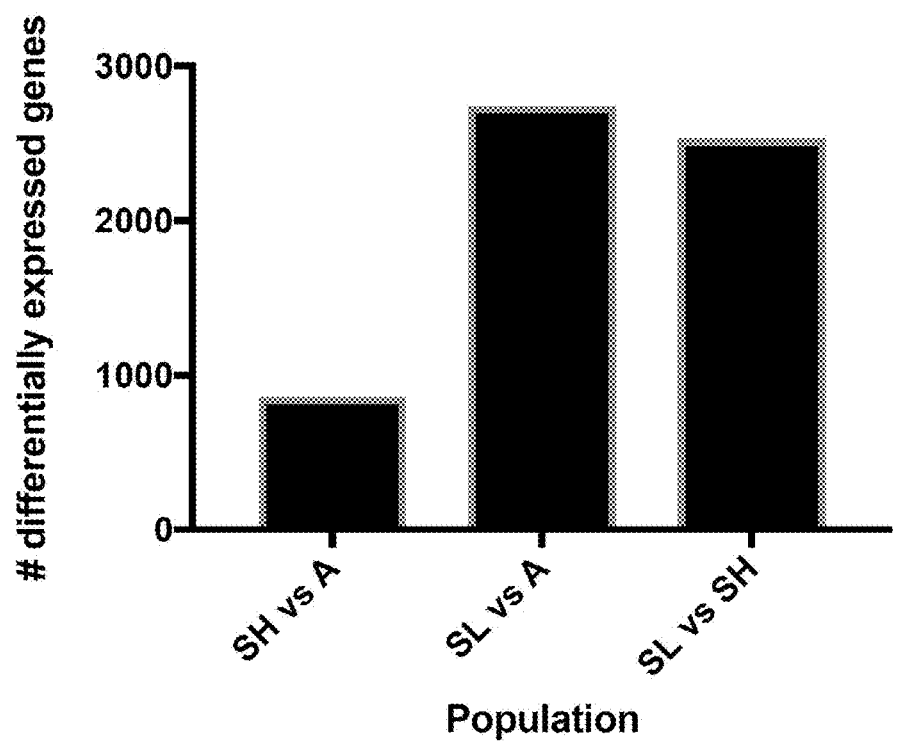
FIG. 23A-23C A subset of macrophage genes are upregulated early in MTB infection, FIG. 23A charts the number of differentially expressed genes between each infection condition.
Figure 23B:
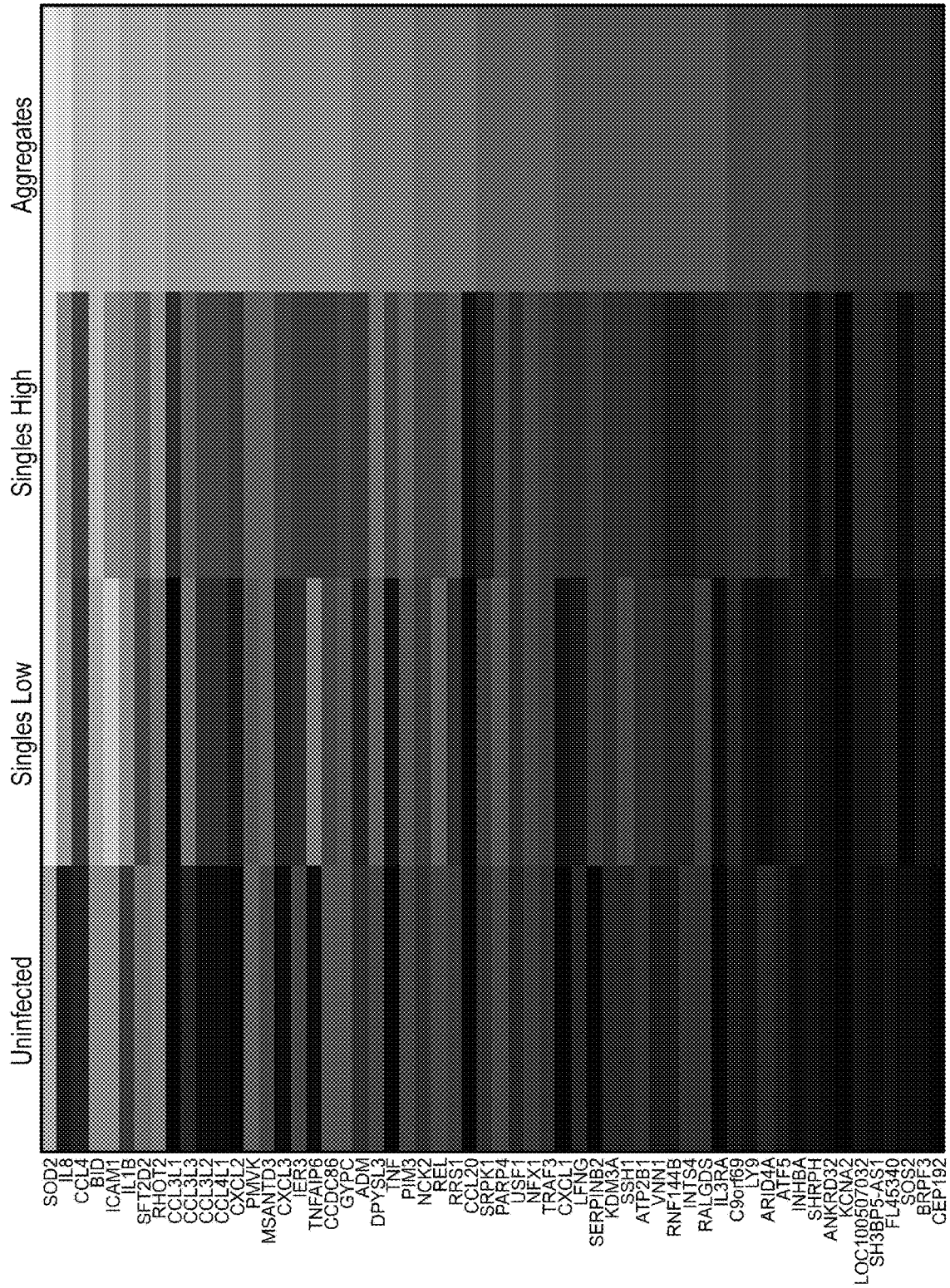
Figure 23C:
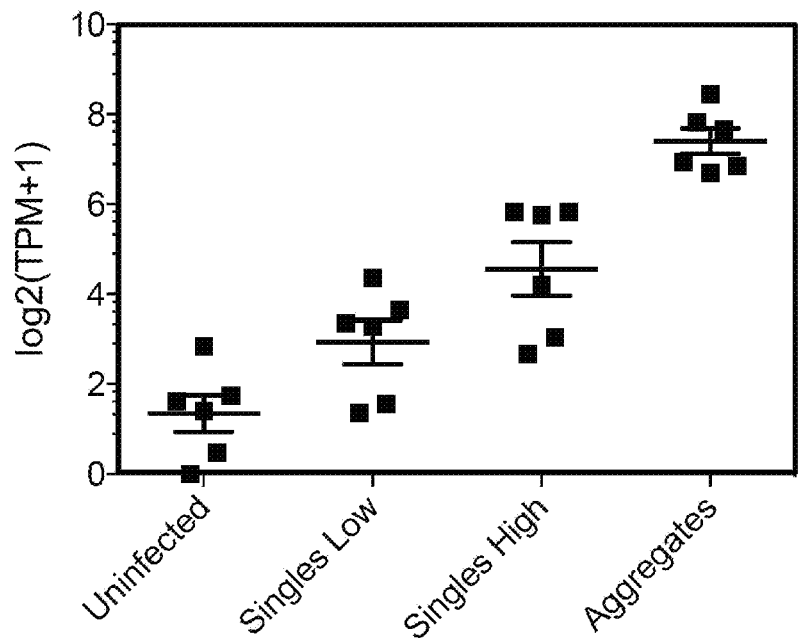
Figure 23C:
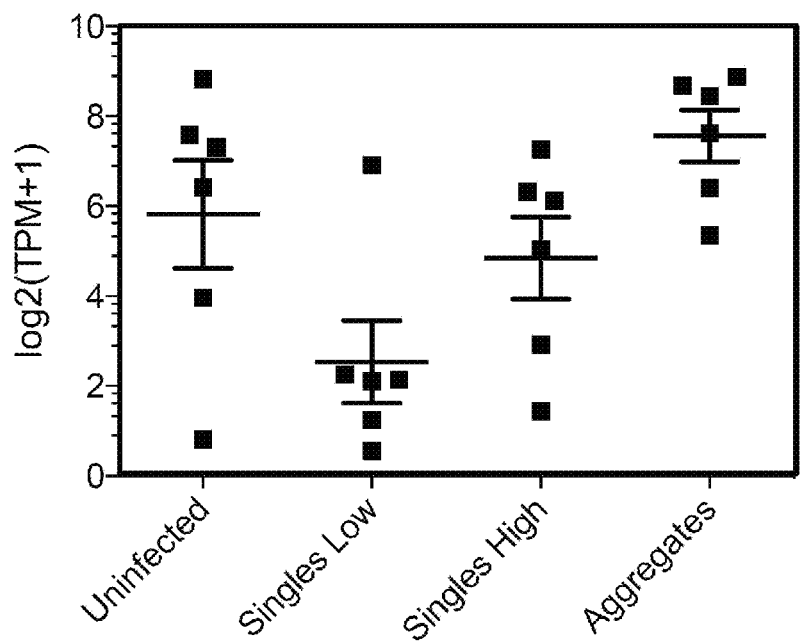

MDMs infected with aggregates upregulate unique gene expression programs in comparison to MDMs infected with a single *bacillus* and many single bacilli, shown in FIG. 23A-23C.

Two patterns are observed in differential gene expression: gradual increase in gene expression from uninfected, to singles low infected, to singles high infected, to aggregate infected MDMs, and gene expression that was only upregulated in aggregate infected MDMs in comparison to uninfected, singles low infected, and singles high infected. FIG. 24A-24C.

Figure 25A:
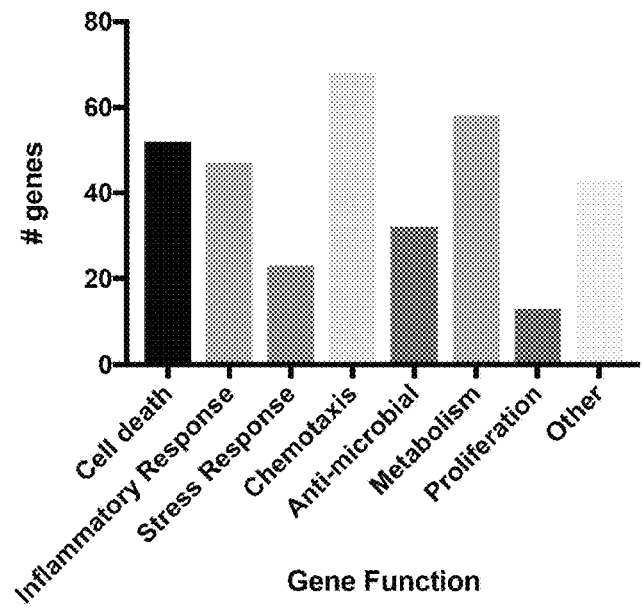
Figure 25B:
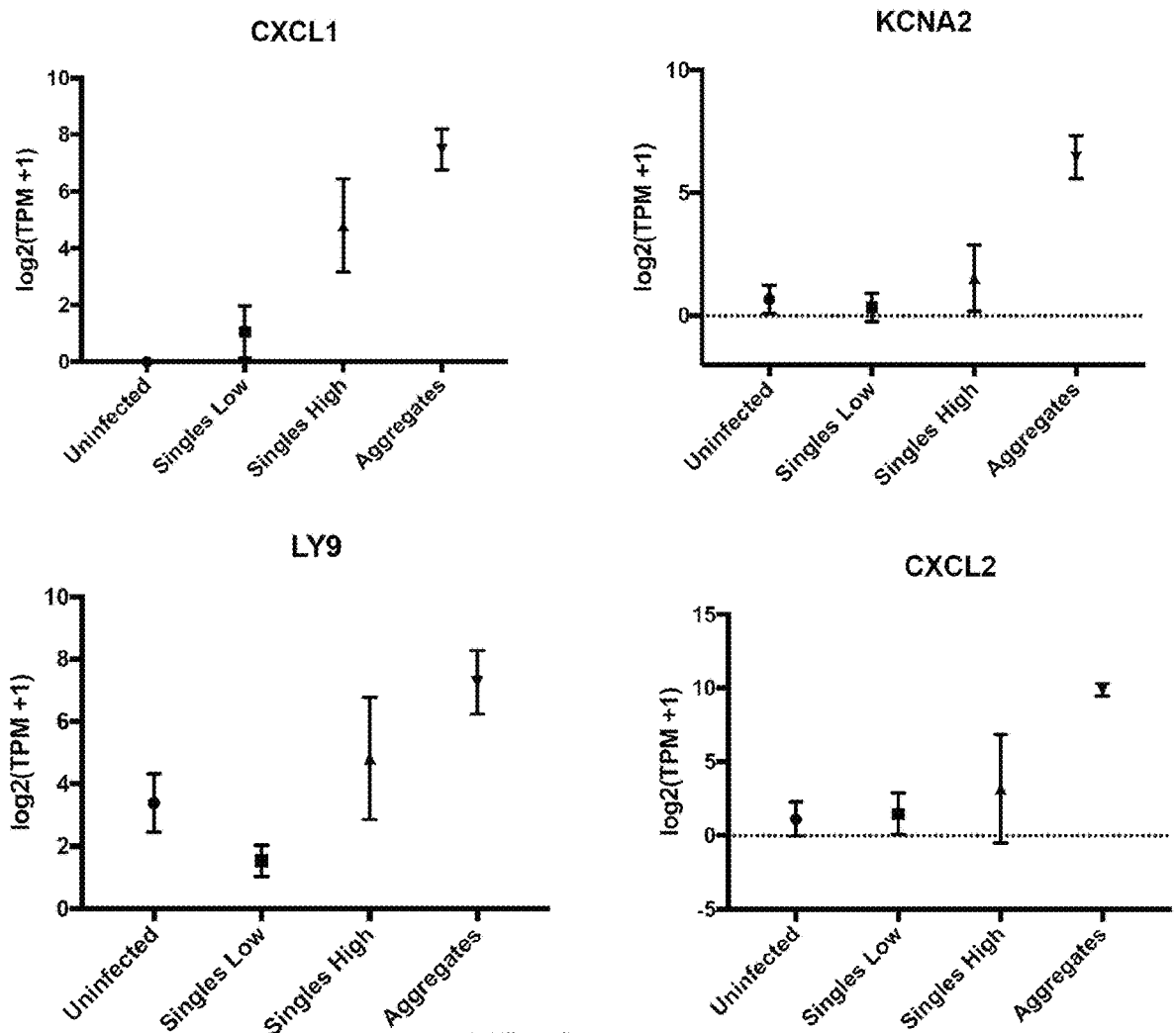
FIG. 25B singles high vs. singles low.

Genetic programs involved in inflammation, regulation of cell death, chemotaxis, and anti-microbial function are differentially induced as a function of bacilli aggregation or isolation (singles). FIG. 25A-25B. The results indicate that by controlling for intracellular abundance of Mtb, it is possible to untangle the cellular response to MOI vs. bacilli aggregation state.

Various modifications and variations of the described methods, pharmaceutical compositions, and kits of the invention will be apparent to those skilled in the art without departing from the scope and spirit of the invention. Although the invention has been described in connection with specific embodiments, it will be understood that it is capable of further modifications and that the invention as claimed should not be unduly limited to such specific embodiments. Indeed, various modifications of the described modes for carrying out the invention that are obvious to those skilled in the art are intended to be within the scope of the invention. This application is intended to cover any variations, uses, or adaptations of the invention following, in general, the principles of the invention and including such departures from the present disclosure come within known customary practice within the art to which the invention pertains and may be applied to the essential features herein before set forth.

The invention claimed is:

1. A method of modulating one or more host genes or product of one or more host genes in a cell or tissue infected with *Mycobacterium tuberculosis*, the method comprising contacting the cell or tissue with a modulating agent in an amount sufficient to decrease expression of genes whose expression is increased in a cell infected with *Mycobacterium tuberculosis* or increase expression of genes whose expression is decreased in a cell infected with *Mycobacterium tuberculosis* to modify the *Mycobacterium tuberculosis* infection of the cell or tissue as compared to the infection in the absence of the modulating agent,
wherein the modulating agent is a programmable DNA-binding protein, wherein said DNA-binding protein is a CRISPR system, and wherein (a) the host genes whose expression is increased in a cell infected with *Mycobacterium tuberculosis* comprises:
(i) one or more of RAC1, RAB3C, TARBP2, TSPYL2, MED27, H2AFY, NAP1L3, ZW10, RNF20, HERC6, UCHL5, KLHL12, TRIM63, KLHL3, CAPN11, MMP16, ACSL4, DUSP1, PPP3R1, LGALS12, IL1A, DHCR24, APLF, RAPSN, RHOD, VEPH1, MTNR1A, ZNF12, RRAGD, PRDM8, ASXL3, SNA13, ZDHHC7, GLIS1, ZNF24, HNF4G, FGD4, MSC, NOP10, MEIS2, DUSP26, PCDHGA10, CRTAC1, TRPV2, NR1H3, CCL3, SLC1A3, CCL3L3, IL27RA, HAPLN3, COL11A1, SERPINI1, SDC2, OR5K3, CNNM4, CLDN6, OSBPL9, GGT2, SVOPL, and FAM162A, in combination with APOC1;
(ii) one or more of IFNB1, TREX1, CXCL10, IFNA17, IL1A, BMP6, IL20, TRAF2, HDAC9, CDKN2C, PPP2R2C, and CCND1; and
(iii) one or more of KCNA2, CXCL2, CCL4, and IL8; or
(b) the host genes whose expression is decreased in a cell infected with *Mycobacterium tuberculosis* comprises:
(i) one or more of PGAP3, DPY30, PNPLA8, ARHGEF2, SCYL1, SVIP, ELOVL3, UBE2V1P2, LMF1, SNX17, DLGAP5, PPL, DMD, AKAP12, TUBBP5, CDC42SE1, TUBB8, MRPL45, CYB561, RPA4, TOP3B, SNAPC5, BCSIL, GTF2B, NAPIL4, GCHFR, MGEA5, RABL3, RAB28, HSPA14, PCK2, CDKL2, HNRNPL, IMMP1L, SIVA1, PDCD10, SSTR3, RARB, ZNF831, ZNF92, RNF181, FAM90A24P, APOBEC3A, ZNF426, MCHR2, OR51I2, OR2B3, OPNILW, IL1RAPL1, PLXNB2, RTN3, SLC26A7, DNAJC4, CP, SSX6, AADACL2, RNASE11, and IGKC; and
(ii) one or more of REGIP, CD69, CD22, SFTAP1, CD72, IFNA1, IFNA13, DHX58, TRADD, FCER1A, SDC1, CD276, TP53I13, GPC1, BAG4, IL36G, ARG2, IL1F10 and MAP4K4, in combination with PCSK9.

2. The method of claim 1, wherein the modulating of the cell or tissue infected with *Mycobacterium tuberculosis* comprises modulating a host gene or product of one or more host genes whose expression is increased in a cell infected with *Mycobacterium tuberculosis*.

3. The method of claim 2, wherein the one or more host genes encodes a component of apoptosis, vesicle transport, an immune response or a metabolic pathway.

4. The method of claim 1, wherein the modulating of the cell or tissue infected with *Mycobacterium tuberculosis* comprises modulating a host gene or product of one or more host genes whose expression is decreased in a cell infected with *Mycobacterium tuberculosis*.

5. The method of claim 4, wherein the one or more host genes encodes a transcription factor, a growth factor, a telomere maintenance factor, or a component of a metabolic pathway.

6. The method of claim 2, wherein the host gene whose expression is increased is correlated with the copy number of *Mycobacterium tuberculosis* in the cell.

7. The method of claim 1, wherein the one or more host genes comprise host gene functions comprising one or more of sugar binding, RIG-I-like receptor signaling pathway, cell surface protein, SODD/TNFR1 signaling pathway, interferon-alpha/beta receptor binding, IL-10 signaling, cytosolic DNA-sensing pathway, cytokines, or cyclins and cell cycle regulators.

8. The method of claim 1, wherein the host gene is associated with endocytosis or intracellular transport and is selected from the group consisting of RAB3C, RAC1, and NR1H3, in combination with APOC1.

9. The method of claim 1, wherein the host gene is associated with macromolecular complex assembly and is selected from the group consisting of TARBP2, TSPYL2, MED27, RAC1, H2AFY, NAP1L3, ZW10, and RNF20, in combination with APOC1.

10. The method of claim 1, wherein the host gene comprises CCL4, and/or IL8.

11. The method of claim 1, wherein the host gene is associated with chemotaxis, inflammatory response, metabolism, or cell death.

12. The method of claim 1, wherein the host gene is KCNA2 or CXCL2.

13. The method of claim 1, wherein the RNA targeting inhibitory nucleic acid molecule is selected from the group consisting of antisense oligonucleotide (ASO), siRNA, microRNA, dsRNA, and ribozyme.

* * * * *

UNITED STATES PATENT AND TRADEMARK OFFICE
CERTIFICATE OF CORRECTION

PATENT NO. : 11,680,296 B2
APPLICATION NO. : 16/756655
DATED : June 20, 2023
INVENTOR(S) : Alexander K. Shalek et al.

It is certified that error appears in the above-identified patent and that said Letters Patent is hereby corrected as shown below:

In the Specification

In Column 7, Line 13, delete "+1-10%" and insert -- +/−10% --.

In Column 12, Line 48, delete "lgM" and insert -- IgM --.

In Column 18, Lines 33-34, delete "(epigallocatechin" and insert -- (epigallocatechin-3S- --.

In Column 18, Line 48, delete "KDMS-C70," and insert -- KDM5-C70, --.

In Column 18, Line 53, delete "UNCO224." and insert -- UNC0224. --.

In Column 23, Line 26, delete "bi sulfate," and insert -- bisulfate, --.

In Column 26, Line 38, delete "1-1000" and insert -- 1-1000 µg, --.

In Column 59, Line 38, delete "(MA)," and insert -- (RIA), --.

In Columns 71-72 (Table 1-continued), Line 64, delete "SNAG," and insert -- SNAI3, --.

In Columns 73-74 (Table 1-continued), Line 9, delete "NF12" and insert -- ZNF12 --.

In Columns 73-74 (Table 1-continued), Line 51, delete "ILIA" and insert -- IL1A --.

In Columns 75-76 (Table 1-continued), Line 9, delete "biosynthetic of process" and insert -- biosynthetic process --.

In Columns 79-80 (Table 1-continued), Line 11, delete "domaiCytoplasmic" and insert -- domain:Cytoplasmic --.

Signed and Sealed this
Eighteenth Day of March, 2025

Coke Morgan Stewart
*Acting Director of the United States Patent and Trademark Office*

CERTIFICATE OF CORRECTION (continued)
U.S. Pat. No. 11,680,296 B2

In Columns 81-82 (Table 2-continued), Line 43, delete "micro tubule" and insert -- microtubule --.

In Column 89, Line 42, delete "PLACE," and insert -- PLAC8, --.

In the Claims

In Column 99, Line 41, in Claim 1, delete "ILIA," and insert -- IL1A, --.

In Column 99, Line 50, in Claim 1, delete "BCSIL," and insert -- BCS1L, --.

In Column 99, Line 50, in Claim 1, delete "NAPIL4, GCHFR" and insert -- NAPIL4, GCHFR, --.

In Column 99, Line 55, in Claim 1, delete "OPNILW," and insert -- OPN1LW, --.